(12) United States Patent
Godowski et al.

(10) Patent No.: US 6,994,856 B1
(45) Date of Patent: Feb. 7, 2006

(54) ERBB4 RECEPTOR-SPECIFIC NEUREGULIN RELATED LIGANDS AND USES THEREFOR

(75) Inventors: Paul J. Godowski, Burlingame, CA (US); Melanie Rose Mark, Burlingame, CA (US); Dong-Xiao Zhang, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/107,979

(22) Filed: Jun. 30, 1998

Related U.S. Application Data

(60) Provisional application No. 60/053,641, filed on Jul. 24, 1997.

(51) Int. Cl.
  A61K 39/395  (2006.01)
  C07K 14/00  (2006.01)
  C07K 16/00  (2006.01)
(52) U.S. Cl. ............... 424/178.1; 530/350; 530/391.1
(58) Field of Classification Search ............. 424/178.1; 435/7.8, 69.7; 530/387.1, 387.3, 827, 350, 530/391.1
See application file for complete search history.

(56) References Cited

U.S. PATENT DOCUMENTS

| 4,892,538 A | 1/1990 | Aebischer et al. ........ 604/891.1 |
| 5,011,472 A | 4/1991 | Aebischer et al. ............ 604/50 |
| 5,714,147 A * | 2/1998 | Capon et al. ............ 424/178.1 |
| 6,727,077 B1 | 4/2004 | Young et al. |
| 2004/0048295 A1 | 3/2004 | Young et al. |

FOREIGN PATENT DOCUMENTS

| WO | WO 92/19195 | 11/1992 |
| WO | WO 93/25673 | 12/1993 |
| WO | WO 95/05452 | 2/1995 |
| WO | WO 96/15244 | 5/1996 |
| WO | WO 96/36720 | 11/1996 |
| WO | WO 97/09425 | 3/1997 |

OTHER PUBLICATIONS

Rudinger et al. in "Peptide Hormones", edited by Parsons University Park Press, p. 6, Jun. 1976.*
Burgess et al. J Cell Biol, 111:2129-2138, 1990.*
Aebischer et al., "Intrathecal delivery of CNTF using encapsulated genetically modified xenogeneic cells in amyotrophic lateral sclerosis patients" *Nature Medicine* (published erratum appears in Nat Med Sep. 1996; 2(9) : 1041) 2(6) :696-699 (Jun. 1996).
Barbacci et al., "The structural basis for the specificity of epidermal growth factor and heregulin binding" *Journal of Biological Chemistry* (published erratum appears in J Biol Chem Nov. 24, 1995;270(47) : 28494) 270(16):9585-9589 (Apr. 21, 1995).
Beerli et al., "Epidermal growth factor-related peptides activate distinct subsets of ErbB receptors and differ in their biological activities" *Journal of Biological Chemistry* 271 (11):6071-6076 (Mar. 15, 1996).
Blobel, G., "Intracellular protein topogenesis" *Proc. Natl. Acad. Sci. USA* 77(3):1496-1500 (Mar. 1980).
Carraway et al., "The erbB3 gene product is a receptor for heregulin" *Journal of Biological Chemistry* 269(19):14303-14306 (1994).
Carraway et al., "A Neu Acquaintance for ErbB3 and ErbB4: A Role for Receptor Heterodimerization in Growth Signaling" *Cell* 78:5-8 (Jul. 15, 1994).
Carraway, et al., "Neuregulin-2, a new ligand of ErbB3/ErbB4-receptor tyrosine kinases" *Nature* 387:512-516 (1997).
Chang, et al., "Ligands for ErbB-family receptors encoded by a neuregulin-like gene" *Nature* 387:509-512 (1997).
Derynck et al., "Human transforming growth factor-α: Precursor structure and expression in *E. coli*" *Cell* 38:287-297 (1984).
Falls et al., "ARIA, a protein that stimulates acetylcholine receptor synthesis, is a member of the Neu ligand family" *Cell* 72:801-815 (1993).
Godowski et al., "Characterization of the human growth hormone receptor gene and demonstration of a partial gene deletion in two patients with Laron-type dwarfism" *Proc. Natl. Acad. Sci. USA* 86:8083-8087 (1989).
Higashiyama et al., "A Heparin-Binding Growth Factor Secreted by Macrophage-Like Cells That is Related to EGF" *Science* 251:936-939 (1991).
Hillier et al. (Genbank Database Accession No. H49100) (1995).
Ho, W., et al., "Sensory and Motor Neuron-derived Factor" *Journal of Biological Chemistry* 270(24):14523-14532 (Jun. 16, 1995).
Holmes et al., "Identification of heregulin, a specific activator of p185$^{erbB2}$" *Science* 256:1205-1210 (1992).
Karunagaran et al., "ErbB-2 is a Common Auxiliary Subunit of NDF and EGF Receptors: Implications for Breast Cancer" *EMBO Journal* 15(2):254-264 (1996).

(Continued)

*Primary Examiner*—Karen A. Canella
(74) *Attorney, Agent, or Firm*—Genentech, Inc.

(57) ABSTRACT

The invention concerns a novel neuregulin related ligand (NRG3) including fragments and variants thereof, as new members of the neuregulin family of compounds. The invention also concerns methods and means for producing NRG3. The native polypeptides of the invention are characterized by containing an extracellular domain including an EGF-like domain, a transmembrane domain and a cytoplasmic domain. Isolated nucleotide sequences encoding such polypeptides, expression vectors containing the nucleotide sequences, recombinant host cells transformed with the vectors, and methods for the recombinant production for the novel NRG3s are also within the scope of the invention.

2 Claims, 11 Drawing Sheets

OTHER PUBLICATIONS

Kita et al., "NDF/heregulin stimulates the phosphorylation of Her3/erb3B3" *FEBS letters* 349(1):139-143 (Jul. 25, 1994).

Nagai et al., "Molecular cloning of cDNA cloning for human preprourokinase" *Gene* 36(1-2):183-188 (1985).

Plowman et al., "The Amphiregulin Gene Encodes a Novel Epidermal Growth Factor-Related Protein with Tumor-Inhibitory Activity" *Molecular & Cellular Biology* 10:1969-1981 (1990).

Plowman et al., "Heregulin induces tyrosine phosphorylation of HER4/p180$^{erbB4}$" *Nature* (Letters to Nature) 366:473-475 (Dec. 2, 1993).

Riese et al., "The cellular response to neuregulins is governed by complex interactions of the erbB receptor family" *Molecular & Cellular Biology* (published erratum appears in Mol Cell Biol Feb. 1996; 16(2):735) 15(10):5770-5776 (Oct. 1995).

Sabatini et al., "Mechanisms for the incorporation of proteins in membranes and organelles" *Journal of Cell Biology* 92(1):1-22 (Jan. 1982).

Sasada et al., "Cloning and expression of cDNA encoding human betacellulin, a new member of the EGF family" *Biochemical & Biophysical Research Communications* 190(3):1173-1179 (Feb. 15, 1993).

Sliwkowski et al., "Coexpression of erbB2 and erbB3 proteins reconstitutes a high affinity receptor for heregulin" *Journal of Biological Chemistry* 269(20):14661-14665 (1994).

Toyoda et al., "Molecular cloning of mouse epiregulin, a novel epidermal growth factor-related protein, expressed in the early stage of development" *FEBS Letters* 377(3):403-407 (Dec. 27, 1995).

Tzahar et al., "ErbB-3 and ErbB-4 Function as the Respective Low and High Affinity Receptors of All Neu Differentiation Factor/Heregulin Isoforms" *Journal of Biological Chemistry* 269(40):25226-25233 (1994).

Wickner et al., "Multiple mechanisms of protein insertion into and across membranes" *Science* 230(4724):400-407 (Oct. 25, 1985).

Zhang et al., "Neuregulin-3 (NRG3): A novel neural tissue-enriched protein that binds and activates ErbB4" *Proc. Natl. Acad. Sci. USA* 94:9562-9567 (Sep. 22, 1997).

* cited by examiner

CCTGACCGGCCGGCGGCGCCCGGGCCGGTCTCGCCCCTCTACCGAGCGCCTCGCCGCC
CCCTCCCCGGCCCGCGTCCCCTCCCCCGTCCTCTCCTCCCCGCCCGCCGCCCGCCTCTC
GGGGGGAGGGGCGTGGGGGCAGGGAGCCGATTTGCATGCGGCCGCCGCGGCCGCTG
CCTGAGCCGGAGCCCGCCGCCGCCGGAGCCCGCGCCCGCGCCCGCGCCCGGCCCGCG
CGGCCCCATGCCTCTGGCGCGGCCCTCGGGGGGGCGAAGGTGAAGATCGGCTCCTAG
GATGAGTGAAGGGGCGGCCGGTGCCTCGCCACCTGGTGCCGCTTCGGCAGCCGCCGC
CTCAGCCGAGGAGGGCACCGCGGCGGCTGCGGCGGCGGCGGCGGCGGGCGGGGGCC
CGGACGGCGGCGGAGAAGGGGCGGCCGAACCCCCCGGGAGTTACGCTGTAGCGACT
GCATCGTGTGGAACCGGCAGCAGACGTGGTTGTGCGTGGTGCCTCTGTTCATCGGCTT
CATCGGCCTGGGGCTCAGCCTCATGCTGCTTAAATGGATCGTGGTAGGCTCCGTCAAG
GAGTACGTGCCCACGGACCTGGTGGACTCCAAGGGAATGGGCCAGGACCCCTTCTTCC
TCTCCAAGCCCAGCTCTTTCCCCAAGGCTATGGAAACCACCACAACAACCACTTCTACC
ACGTCCCCCGCCACCCCTCTGCCGGCGGCGCCGCTTCTTCCAGGACGCCTAACCGGA
TTAGCACCCGCTTGACCACCATCACACGGGCACCCACCCGCTTCCCTGGGCACCGGGT
TCCCATCCGGGCTAGCCCGCGCTCTACCACAGCACGGAACACTGCTGCCCCTCCGACG
GTCCTGTCCACCACGGCCCCTTTCTTCAGTAGCAGCACGCCCGGCTCCCGACCCCCGAT
GCCAGGAGCCCCCAGTACGCAGGCGATGCCTTCCTGGCCCACTGCGGCGTATGCTACC
TCCTCCTACCTCCACGATTCCACTCCCTCCTGGACCCTGTCACCCTTTCAGGATGCTGC
TGCCGCCTCTTCCTCCTCACCCTCTTCCACCTCCTCCACTACCACCACCCCAGAAACTA
GCACCAGCCCCAAATTTCATACTACAACATACTCCACTGAACGATCTGAGCACTTCAA
ACCCTGTCGAGACAAGGACCTGGCGTATTGTCTCAATGATGGTGAATGCTTTGTGATT
GAGACCCTGACAGGATCCCATAAGCACTGTCGGTGCAAGGAAGGCTACCAAGGAGTC
CGTTGTGATCAATTTCTGCCGAAAACAGACTCCATCTTATCGGATCCAACAGACCACTT
GGGGATTGAATTCATGGAGAGTGAAGACGTTTATCAAAGGCAGGTGCTGTCAATTTCA
TGTATCATCTTTGGAATTGTCATCGTGGGCATGTTCTGTGCAGCATTCTACTTCAAAAG
CAAGAAACAAGCTAAACAAATTCAGGAGCACCTGAAAGAGTCACAGAATGGGAAGAA
CTACAGCCTCAAGGCATCCAGCACAAAGTCTGAGAGCTTGATGAAGAGCCATGTCCAT
CTACAAAATTATTCAAAGGCGGATAGGCATCCTGTGACTGCGCTGGAGAAAATAATGG
AGTCAAGTTTTTCAGCTCCCCAGTCGTTCCCAGAAGTCACTTCTCCTGACCGAGGAAG
CCAGCCTATCAAGCACCACAGCCCAGGACAAAGGAGTGGGATGTTGCATAGGAATAC
TTTCAGAAGGGCACCACCCTCACCCCGAAGTCGACTGGGTGGTATTGTAGGACCAGCA
TATCAACAACTTGAAGAATCAAGAATTCCAGACCAGGATACGATACCTTGCCAAGGGA
TAGAGGTCAGGAAGACTATATCCCACCTGCCTATACAGCTGTGGTGTGTTGAAAGACC
CCTGGACTTAAAGTATGTGTCCAATGGCTTAAGAACCCAACAAAATGCATCAATAAAT
ATGCAACTGCCTTCAAGAGAGACAAACCCCTATTTTAATAGCTTGGATCAAAAGGACC
TGGTGGGTTATTTATCCCCAAGGGCCAATTCTGTGCCCATCATCCCGTCGATGGGTCTA
GAAGAAACCTGCATGCAAATGCCAGGGATTTCTGACGTCAAAAGCATTAAATGGTGCA
AAAACTCCTACTCCGCTGACATTGTCAACGCGAGTATGCCAGTCAGTGATTGTCTTCTA
GAAGAACAACAGGAAGTGAAAATATTACTAGAGACTGTGCAGGAACAGATCCGGATT
CTGACTGATGCCAGACGGTCAGAAGACTTCGAACTGGCCAGCATGGAAACTGAGGAC
AGTGCGAGCGAAAACACAGCCTTTCTCCCCCTGAGTCCCACGGCCAAATCAGAACGAG
AGGCACAATTTGTCTTAAGAAATGAAATACAAAGAGACTCTGTGCTAACCAAGTGACT
GGAAATGTAGGAATCTGTGCATTATATGCTTTGCTAAACAGGAAGGAGAGGAAATTA
AATACAAATTATTTATATGCATTAATTTAAGAGCATCTACTTAGAAGCC

FIG. 1

```
TCACCGACCTAGTGGACTCCACTAGGTCGGTGGGCACGTACTCCTTGACGGAGCCCAC
CACGATCCATTTGAGAAGCATGAGGCGCGGCCCCATGCCTCTGCCGCGGCCCTCGGGG
GGGCGAAGGTGAANACCGGCTCCTAGGATGAGTGAAGGGGCGGCCGCTGCCTCGCCA
CCTGGTGCCGCTTCGGCAGCCGCCGCCTCGGCCGAGGAGGGCACCGCGGCGGCTGCG
GCGGCGGCAGCGGCGGGCGGGGCCCGGACGGCGGCGGCGAAGGGGCGGCCGAGCC
CCCCCGGGAGTTACGCTGTAGCGACTGCATCGTGTGGAACCGGCAGCAGACGTGGCT
GTGCGTGGTACCTCTGTTCATCGGCTTCATCGGCCTGGGGCTCAGCCTCATGCTTCTCA
AATGGATCGTGGTGGGCTCCGTCAAGGAGTACGTGCCCACCGACCTAGTGGACTCCAA
GGGGATGGGCCAGGACCCCTTCTTCCTCTCCAAGCCCAGCTCTTTCCCCAAGGCCATG
GAGACCACCACCACTACCACTTCCACCACGTCCCCCGCCACCCCTCCGCCGGGGGTG
CCGCCTCCTCCAGGACGCCCAACCGGATTAGCACTCGCCTGACCACCATCACGCGGGC
GCCCACTCGCTTCCCCGGGCACCGGGTGCCCATCCGGGCCAGCCCGCGCTCCACCACA
GCACGGAACACTGCGGCCCTGCGACGGTCCCGTCCACCACGGCCCCGTTCTTCAGTA
GCAGCACGCTGGGCTCCCGACCCCCGGTGCCAGGAACTCCAAGTACCCAGGCAATGCC
CTCCTGGCCTACTGCGGCATACGCTACCTCCTCCTACCTTCACGATTCTACTCCCTCCT
GGACCCTGTCTCCCTTTCAGGATGCTGCCTCCTCTTCTTCCTCTTCTTCCTCCTCCGCTA
CCACCACCACACCAGAAACTAGCACCAGCCCCAAATTTCATACGACGACATATTCCAC
AGAGCGATCCGAGCACTTCAAACCCTGCCGAGACAAGGACCTTGCATACTGTCTCAAT
GATGGCGAGTGCTTTGTGATCGAAACCCTGACCGGATCCCATAAACACTGTCGGTGCA
AAGAAGGCTACCAAGGAGTCCGTTGTGATCAATTTCTGCCGAAAACTGATTCCATCTT
ATCGGATCCAACAGACCACTTGGGGATTGAATTCATGGAGAGTGAAGAAGTTTATCAA
AGGCAGGTGCTGTCAATTTCATGTATCATCTTTGGAATTGTCATCGTGGGCATGTTCTG
TGCAGCATTCTACTTCAAAAGCAAGAAACAAGCTAAACAAATCCAAGAGCAGCTGAA
AGTGCCACAAAATGGTAAAAGCTACAGTCTCAAAGCATCCAGCACAATGGCAAAGTC
AGAGAACTTGGTGAAGAGCCATGTCCAGCTGCAAAATTATTCAAAGGTGGAAAGGCA
TCCTGTGACTGCATTGGAGAAAATGATGGAGTCAAGTTTTGTCGGCCCCAGTCATTC
CCTGAGGTCCCTTCTCCTGACAGAGGAAGCCAGTCTGTCAAACACCACAGGAGTCTAT
CCTCTTGCTGCAGCCCAGGGCAAAGAAGTGGCATGCTCCATAGGAATGCCTTCAGAAG
GACACCCCCGTCACCCCGAAGTAGGCTAGGTGGAATTGTGGGACCAGCATATCAGCA
ACTCGAAGAATCAAGGATCCCAGACCAGGATACGATACCTTGCCAAGGGATAGAGGT
CAGGAAGACTATATCCCACCTGCCTATACAGCTGTGGTGTGTTGAAAGACCCCTGGAC
TTAAAGTATTCATCCAGTGGTTTAAAAACCCAACGAAATACATCAATAAATATGCAAC
TGCCTTCAAGAGAGACAAACCCCTATTTTAATAGCTTGGAGCAAAAGGACCTGGTGGG
CTATTCATCCACAAGGGCCAGTTCTGTGCCCATCATCCCTTCAGTGGGTTTAGAGGAA
ACCTGCCTGCAAATGCCAGGGATTTCTGAAGTCAAAAGCATCAAATGGTGCAAAAACT
CCTATTCAGCTGACGTTGTCAATGTGAGTATTCCAGTCAGCGATTGTCTTATAGCAGA
ACAACAAGAAGTGAAAATATTGCTAGAAACTGTCCAGGAGCAGATCCGAATTCTGACT
GATGCCAGACGGTCAGAAGACTACGAACTGGCCAGCGTAGAAACCGAGGACAGTGCA
AGCGAAAACACAGCCTTTCTCCCCCTGAGTCCCACAGCCAAATCAGAACGAGAGGCGC
AATTTGTCTTAAGAAATGAAATACAAAGAGACTCTGCATTGACCAAGTGACTTGAGAT
GTAGGAATCTGTGCATTCTATGCTTTGCTCAACAGGAAAGAGAGGAAATCAAATACAA
ATTATTTATATGCATTAATTTAAGAGCATCTACTTAGAAGAAACCAAATAGTCTATCGC
CCTCATATCATAGTGTTTTTAACAAAATATTTTTTAAGGGAAAGAAATGTTTCAGGA
GGGATAAAGCTT
```

FIG. 2

ATGAGTGAAGGGGCGGCCGCTGCCTCGCCACCTGGTGCCGCTTCGGCAGCCGCCGCTCGGCGAGG
AGGGCACCGCGGGCGGCTGCGGCGGGCAGCGGGCGGGCGGGCCGACGGGCCGGGCGACGAAGGGG
CGGCCGAGCCCCCCGGGAGTTACGGTCATGCTGTGTGGACTGTGTGGAACCGGCAGAGACGTGCT
GTGCGTGGTACCTCGTTCATCGGCCTGGGGCTCAGCCTACTGTCTCTCAAATGATGT
GGTGGGCTCCGTCAAGGAGTACGTGCCCACCGACTAGTGGACTCCAAGGGATGGCCAGGACCCC
TTCTTCCTCTCCAAGCTCTTTCCCGGGGTGCGCCTCTCCAAGGCCATGGAGACCACCACTTCCACCACG
TCCCCGCCACCCCCTCGGGGGTGCGCCTCTCCCCGGACGCCAACCGGATTAGCACTCGCCT
GACCACCATCACGCGGGCGCCCCACTCGCTCCCCGGCACCGGGTGCCCATCCGGGCCAGCCGCGCT
CCACCACAGCACGAACACTGCGGGCCCCTGCGACGTCCCGTCCACCACGGCCCCGTTCTTCAGTAGC
AGCACGCTGGGCTCCGACCCCGGTGCCAGGAACTCACTTCCAAGTACCCAGCAATGCCCTCCTGGCCTAC
TGCCGGCATACGCTACCTCCTCCTCACGATTCTACTCCCTCCTGACCCTGTCTCCCTTTCAGGA
TGCTGCCTCCTCTCTCTTCTTCTCCGCTACCACCACCACCAGAAACTAGCACCAGCC
CAAATTTCATACGTGACACATATTCCACAGAGCGATCCGAGCACTTCAAACCCTGCGAGACAAGGAC
CTTGCATACTGTCTCAATGATGGCGAGTGCTTTGTGATCGAAACCCTGACGGATCCCATAAACACTG
TCGGTGCAAGAAGGCTACCAGGAGTCCGTTGATCAATTTCTGCCGAAAACTGATTCCATCTTAT
CGGATCCAACAGACCACTTGGGGATTGAATTCATGGAGAGTGAAGAAGTTATCAAAGGCAGGTGCT
GTCAAATTTCATGTATCATCTTTGGAATTGTCATCGTGGGCATGTTCTGTGCAGCATTCTACTTCAAAAG
CAAGAAACAAGCTAAACAAATCCAAGACAGCAGTGAAAGTGCCACAAATGTAAAGTACAGTCTC
AAAGCATCCAGCAAAGGCACACTGTGACTCGTAGGCAAAGTCAGAGAGCATTCATTGGAGAAGCCAGTCTCAAAATTATT
CAAAGGTGGCAAAGGCATCCTGTGACTCGTGTCTCCTGACAGAGAAGCCAGTCTGTCAAACACCACAGAGTCTATCCT
GTCATTCCCTGAGTCCCCTTCCTGCAGGAAGTGGCATGCTCCATAGGAAGTGCTCCATAGGAATGCCTTCAGAAGGACCACCCCGTC
CTTGCTGCAGCCCAGGCAAAGAAGTGGCATGCTCCATAGGAAGTGCTCCATAGGAATGCCAACTCGAAGAATCAAGGATCCA
ACCCCGAAGTAGGCGTAGGTGAATTGGGACCCAGCATATCCAGTGGTTTAAAACCCAACGAAATACATCAAT
GACCAGGATACGATACCTTGCCAAGGTATTCATCCAGTGGTTTAAAACCTGGAGCAAAGGACCTGGTG
AAATATGCAACTGCCTTCAAGAGAGACAAACCCCTATTTAATAGCTTGGAGCAAAGGACCTGGTG
GGCTATTCATCATCCACAAGGGCCTTCAAGGGCCAGTTCTGTGCCATCATCCCTTCAGTGGTTTAGAGGAAACCTGCT
GCAAATGCCAGGATTTCTGAAGTCAAAGCATCAAATGGTCAAAACTCCTATTCAGCTGACGTTG
TCAATGTGAGTATTCCAGTCAGCAGATCCGAATTCTGACTGATGCCAGACGGTCAGAAGACTACGAACTGGCAGCG
ACTGTCCAGGAGCAGATCCGAATTCTGACTGATGCCAGACGGTCAGAAGACTACGAACTGGCAGCG
TAGAAACCGAGGACAGTGCAAGTGAAAACACAGCCTTTCCCCTGAGTCCCACAGCCAAATCAGA
ACGAGAGGGCAATTTGTCTTAAGAAATGAAATACAAGAGAGACTCTGCATTGACCAAGTGA

FIG. 3

```
hNRG3B1   1 MSEGAAA ASPPGAASAAAASAEEGTAAAAAAAAGGGPDGGGEGAAEPPR
mNRG3     1 MSEGAAG ASPPGAASAAAASAEEGTAAAAAAAAGGGPDGGGEGAAEPPR

Hϕ
hNRG3B1  51 ELRCSDCIVWNRQQTWLCVVPLFIGFIGLGLSLMLLKWIVVGSVKEYVPT
mNRG3    51 ELRCSDCIVWNRQQTWLCVVPLFIGFIGLGLSLMLLKWIVVGSVKEYVPT

S/T rich
hNRG3B1 101 DLVDSKGMGQDPFFLSKPSSFPKAMETTTTTTSTTSPATPSAGGAASSRT
mNRG3   101 DLVDSKGMGQDPFFLSKPSSFPKAMETTTTTTTSTTSPATPSAGGAASSRT hNRG3B1 151 PNRISTRLTTTITRAPTRFPGHRVPIRASPRSTTARNTAAPATVPSTTAPF
mNRG3   151 PNRISTRLTTTITRAPTRFPGHRVPIRASPRSTTARNTAAPPTVLSTTAPF hNRG3B1 201 FSSSTLGSRPPVPGTPSTQAMPSWPTAAYATSSYLHDSTPSWTLSPFQD-
mNRG3   201 FSSSTPGSRPPMPGAPSTQAMPSWPTAAYATSSYLHDSTPSWTLSPFQDA EGF-like
hNRG3B1 250 -AASSSSISSATTTTPETSTSPKFHTTTYSTERSEHFKPCRDKDLAYC
mNRG3   251 AAASSSSPSSTTTTTPETSTSPKFHTTTYSTERSEHFKPCRDKDLAYC hNRG3B1 299 LNDGECFVIETLTGSHKHCRCKEGYQGVRCDQFLPKTDSILSDPTDHLGI
mNRG3   301 LNDGECFVIETLTGSHKHCRCKEGYQGVRCDQFLPKTDSILSDPTDHLGI
```

FIG. 4A-1

```
                                         TM
hNRG3B1 349 EFMESEE VYQRQVLSISCIIFGIVIVGMFCAAFYFKSKKQAKQIEQ LKV
mNRG3    351 EFMESED VYQRQVLSISCIIFGIVIVGMFCAAFYFKSKKQAKQIEH LKE hNRG3B1 399 PQNGKS YSLKASSTMAKSEN LVKSHV QLQNYSKVE RHPVTALEK MMESSF
mNRG3    401 SQNGKN YSLKASST-- KSES LMKSHV HLQNYSKAD RHPVTALEK IMESSF hNRG3B1 449 VG PQSFPEVP SPDRGSQSV KHHRSLSSCC SPGQRSGMLHRNA FRRT PPSP
mNRG3    449 SA PQSFPEVT SPDRGSQP IKHH------ SPGQRSGMLHRNT FRRA PPSP hNRG3B1 499 RSRLGGIVGPAYQQLEESRIPDQDTIPCQGIEVRKTISHLPIQLWCVERP
mNRG3    492 RSRLGGIVGPAYQQLEESRIPDQDTIPCQGIEVRKTISHLPIQLWCVERP hNRG3B1 549 LDLKYS SS GLK TQRNT SINMQLPSRETNPYFNSLE QKDLVGYS TRAS SV
mNRG3    542 LDLKYV SN GLR TQQNA SINMQLPSRETNPYFNSLD QKDLVGYL SPRAN SV hNRG3B1 599 PIIPSV GLEETCL QMPGISE VKSIKWCKNSYSAD VNVS IPVSDCL IAEQ
mNRG3    592 PIIPSM GLEETCM QMPGISD VKSIKWCKNSYSAD IVNAS MPVSDCV IEEQ hNRG3B1 649 QEVKILLETVQEQIRILTDARRSEDY ELAS VETEDSASENTAFLPLSPTA
mNRG3    642 QEVKILLETVQEQIRILTDARRSED FELAS METEDSASENTAFLPLSPTA hNRG3B1 699 KSEREAQFVLRNEIQRDSA LTK
mNRG3    692 KSEREAQFVLRNEIQRDSV LTK
```

FIG. 4A-2

```
hNRG3B1    1  M S E G A A A A S P P G A A A S A A A A S A E E G T A A A A A A A A A G G G P D G G G E G A A E P P R
hNRG3B2    1  M S E G A A A A S P P G A A A S A A A A S A E E G T A A A A A A A A A G G G P D G G G E G A A E P P R

H φ
hNRG3B1   51  E L R C S D C I V W N R Q Q T W L C V V P L F I G L G L S L M L L K W I V V G S V K E Y V P T
hNRG3B2   51  E L R C S D C I V W N R Q Q T W L C V V P L F I G L G L S L M L L K W I V V G S V K E Y V P T

↱ S/T rich
hNRG3B1  101  D L V D S K G M G Q D P F F L S K P S S F P K A M E T T T T T T T S T T S P A T P S A G G A A S S R T
hNRG3B2  101  D L V D S K G M G Q D P F F L S K P S S F P K A M E T T T T T T T S T T S P A T P S A G G A A S S R T hNRG3B1  151  P N R I S T R L T T T I T R A P T R F P G H R V P I R A S P R S T T A R N T A A P A T V P S T T A P F
hNRG3B2  151  P N R I S T R L T T T I T R A P T R F P G H R V P I R A S P R S T T A R N T A A P A T V P S T T A P F hNRG3B1  201  F S S S T L G S R P P V P G T P S T Q A M P S W P T A A Y A T S S Y L H D S T P S W T L S P F Q D A
hNRG3B2  201  F S S S T L G S R P P V P G T P S T Q A M P S W P T A A Y A T S S Y L H D S T P S W T L S P F Q D A ↱ EGF-like
hNRG3B1  251  A S S S S S S S S A T T T T T P E T S T S P K F H T T T Y S T E R S E H F K P C R D K D L A Y C L N
hNRG3B2  251  A S S S S S S S S A T T T T T P E T S T S P K F H T T T Y S T E R S E H F K P C R D K D L A Y C L N hNRG3B1  301  D G E C F V I E T L T G S H K H C R C K E G Y Q G V R C D Q F L P K T D S I L S D P T D H L G I E F
hNRG3B2  301  D G E C F V I E T L T G S H K H C R C K E G Y Q G V R C D Q F L P K T D S I L S D P T D H L G I E F
```

FIG. 4B-1

|  |  | TM |  |
|---|---|---|---|
| hNRG3B1 | 351 | MESEEVYQRQVLSISCIIFGIVIVGMFCAAFYFKSKKQAKQIQEQLKVPQ |
| hNRG3B2 | 351 | MESEEVYQRQVLSISCIIFGIVIVGMFCAAFYFKSKKQAKQIQEQLKVPQ |
| hNRG3B1 | 401 | NGKSYSLKASSTMAKSENLVKSHVQLQNYSKVERHPVTALEKMMESSFVG |
| hNRG3B2 | 401 | NGKSYSLKASSTMAKSENLVKSHVQLQNYSKVERHPVTALEKMMESSFVG |
| hNRG3B1 | 451 | PQSFPEVPSPDRGSQSVKHHRSLSSCCCSPGQRSGMLHRNAFRRTPPSPRS |
| hNRG3B2 | 451 | PQSFPEVPSPDRGSQSVKHHRSLSSCCCSPGQRSGMLHRNAFRRTPPSPRS |
| hNRG3B1 | 501 | RLGGIVGPAYQQLEESRIPDQDTIPCQGIEVRKTISHLPIQLWCVERPLD |
| hNRG3B2 | 501 | RLGGIVGPAYQQLEESRIPDQDTIPCQG.................... |
| hNRG3B1 | 551 | LKYSSSGLKTQRNTSINMQLPSRETNPYFNSLEQKDLVGYSSTRASSVPI |
| hNRG3B2 | 529 | ..YSSSGLKTQRNTSINMQLPSRETNPYFNSLEQKDLVGYSSTRASSVPI |
| hNRG3B1 | 601 | IPSVGLEETCLQMPGISEVKSIKWCKNSYSADVVNVSIPVSDCLIAEQQE |
| hNRG3B2 | 577 | IPSVGLEETCLQMPGISEVKSIKWCKNSYSADVVNVSIPVSDCLIAEQQE |
| hNRG3B1 | 651 | VKILLETVQEQIRILTDARRSEDYELASVETEDSASENTAFLPLSPTAKS |
| hNRG3B2 | 627 | VKILLETVQEQIRILTDARRSEDYELASVETEDSASENTAFLPLSPTAKS |
| hNRG3B1 | 701 | EREAQFVLRNEIQRDSALTK |
| hNRG3B2 | 677 | EREAQFVLRNEIQRDSALTK |

ERBB4 RECEPTOR-SPECIFIC NEUREGULIN RELATED LIGANDS AND USES THEREFOR

RELATED APPLICATION

This application is a non-provisional application filed under 37 CFR 1.53(b)(1), claiming priority under 35 USC 119(e) to provisional application No. 60/053,641 filed Jul. 24, 1997, the contents of which are incorporated herein by reference.

FIELD OF THE INVENTION

The present invention concerns novel neuregulin related ligands. More particularly, the invention relates to a new member of the neuregulin family and functional derivatives of the novel polypeptide.

BACKGROUND OF THE INVENTION

Signal transduction affecting cell growth and differentiation is regulated in part by phosphorylation of various cellular proteins. Protein tyrosine kinases are enzymes that catalyze this process. Receptor protein tyrosine kinases are believed to direct cellular growth via ligand-stimulated tyrosine phosphorylation of intracellular substrates. Growth factor receptor protein tyrosine kinases of the class I subfamily include the 170 kDa epidermal growth factor receptor (EGFR) encoded by the erbB1 gene. erbB1 has been causally implicated in human malignancy. In particular, increased expression of this gene has been observed in more aggressive carcinomas of the breast, bladder, lung and stomach. The second member of the class I subfamily, p185$^{neu}$, was originally identified as the product of the transforming gene from neuroblastomas of chemically treated rats. The neu gene (also called erbB2 and HER2) encodes a 185 kDa receptor protein tyrosine kinase. Amplification and/or overexpression of the human HER2 gene correlates with a poor prognosis in breast and ovarian cancers (Slamon et al., (1987) Science 235:177–182; and Slamon et al., (1989) Science 244:707–712). Overexpression of HER2 has been correlated with other carcinomas including carcinomas of the stomach, endometrium, salivary gland, lung, kidney, colon and bladder. A further related gene, called erbB3 or HER3, has also been described (Kraus et al., (1989) Proc. Natl. Acad. Sci. USA 86:9193–9197). Kraus et al. (1989) discovered that markedly elevated levels of erbB3 mRNA were present in certain human mammary tumor cell lines indicating that erbB3, like erbB1 and erbB2, may play a role in human malignancies. The erbB3 gene has been found to be overexpressed in breast (Lemoine et al. (1992) Br. J. Cancer 66:1116–1121), gastrointestinal (Poller et al. (1992) J. Pathol. 168:275–280, Rajkumer et al. (1993) J. Pathol. 170:271–278, and Sanidas et al. (1993) Int. J. Cancer 54:935–940, and pancreatic cancers (Lemoine et al. (1992) J. Pathol. 168:269–273, and Friess et al. (1995) Clinical Cancer Research 1:1413–1420).

The class I subfamily of growth factor receptor protein tyrosine kinases has been further extended to include the HER4/Erb4 receptor (EP Pat Appln No 599,274; Plowman et al. (1993) Proc. Natl. Acad. Sci. USA 90:1746–1750; and Plowman et al. (1993) Nature 366:473–475. Plowman et al. found that increased HER4 expression closely correlated with certain carcinomas of epithelial origin, including breast adenocarcinomas. Diagnostic methods for detection of human neoplastic conditions (especially breast cancers) which evaluate HER4 expression are described in EP Pat Appln No. 599,274.

The quest for the activator of the HER2 oncogene has lead to the discovery of a family of polypeptides, collectively called neuregulins (NRG1). These proteins appear to result from alternate splicing of a single gene which was mapped to the short arm of human chromosome 8 by Orr-Urtreger et al. (1993) Proc. Natl. Acad. Sci. USA 90:1867–1871.

Holmes et al. isolated and cloned a family of polypeptide activators for the HER2 receptor which they called heregulin-α (HRG-α), heregulin-β1 (HRG-β1), heregulin-β2 (HRG-β2), heregulin-β2-like (HRG-β2-like), and heregulin-β3 (HRG-β3). See Holmes et al.(1992) Science 256:1205–1210; WO 92/20798; and U.S. Pat. No. 5,367,060. The 45 kDa polypeptide, HRG-α, was purified from the conditioned medium of the MDA-MB-231 human breast cancer cell line. These researchers demonstrated the ability of the purified heregulin polypeptides to activate tyrosine phosphorylation of the HER2 receptor in MCF7 breast tumor cells. Furthermore, the mitogenic activity of the heregulin polypeptides on SK-BR-3 cells (which express high levels of the HER2 receptor) was illustrated. Like other growth factors which belong to the EGF family, soluble HRG polypeptides appear to be derived from a membrane bound precursor (called pro-HRG) which is proteolytically processed to release the 45 kDa soluble form. These pro-HRGs lack a N-terminal signal peptide.

While heregulins are substantially identical in the first 213 amino acid residues, they are classified into two major types, α and β, based on two variant EGF-like domains which differ in their C-terminal portions. Nevertheless, these EGF-like domains are identical in the spacing of six cysteine residues contained therein. Based on an amino acid sequence comparison, Holmes et al. found that between the first and sixth cysteines in the EGF-like domain, HRGs were 45% similar to heparin-binding EGF-like growth factor (HB-EGF), 35% identical to amphiregulin (AR), 32% identical to TGF-α, and 27% identical to EGF.

The 44 kDa neu differentiation factor (NDF), which is the rat equivalent of human HRG, was first described by Peles et al. (1992) Cell 69:205–216; and Wen et al. (1992) Cell 69:559–572. Like the HRG polypeptides, NDF has an immunoglobulin (Ig) homology domain followed by an EGF-like domain and lacks a N-terminal signal peptide. Subsequently, Wen et al. (1994) Mol. Cell. Biol. 14(3): 1909–1919 carried out cloning experiments to extend the family of NDFs. This work revealed six distinct fibroblastic pro-NDFs. Adopting the nomenclature of Holmes et al., the NDFs are classified as either α or β polypeptides based on the sequences of the EGF-like domains. Isoforms 1 to 4 are characterized on the basis of the region between the EGF-like domain and transmembrane domain. Also, isoforms a, b and c are described which have variable length cytoplasmic domains. These researchers conclude that different NDF isoforms are generated by alternative splicing and perform distinct tissue-specific functions. See also EP 505 148; WO 93/22424; and WO 94/28133 concerning NDF.

Falls et al. (1993) Cell 72:801–815 describe another member of the heregulin family which they call acetylcholine receptor inducing activity (ARIA) polypeptide. The chicken-derived ARIA polypeptide stimulates synthesis of muscle acetylcholine receptors. See also WO 94/08007. ARIA is a β-type heregulin and lacks the entire spacer region rich in glycosylation sites between the Ig-like domain and EGF-like domain of HRGα, and HRGβ1–β3.

Marchionni et al. identified several bovine-derived proteins which they call glial growth factors (GGFs) (Marchionni et al. (1993) Nature 362:312–318). These GGFs share the Ig-like domain and EGF-like domain with the other heregulin proteins described above, but also have an amino-terminal kringle domain. GGFs generally do not have the complete glycosylated spacer region between the Ig-like domain and EGF-like domain. Only one of the GGFs, GGFII, possessed a N-terminal signal peptide. See also WO 92/18627; WO 94/00140; WO 94/04560; WO 94/26298; and WO 95/32724 which refer to GGFs and uses thereof.

Ho et al. in (1995) J. Biol. Chem. 270(4):14523–14532 describe another member of the heregulin family called sensory and motor neuron-derived factor (SMDF). This protein has an EGF-like domain characteristic of all other heregulin polypeptides but a distinct N-terminal domain. The major structural difference between SMDF and the other heregulin polypeptides is the lack in SMDF of the Ig-like domain and the "glyco" spacer characteristic of all the other heregulin polypeptides. Another feature of SMDF is the presence of two stretches of hydrophobic amino acids near the N-terminus.

While the heregulin polypeptides were first identified based on their ability to activate the HER2 receptor (see Holmes et al., supra), it was discovered that certain ovarian cells expressing neu and neu-transfected fibroblasts did not bind or crosslink to NDF, nor did they respond to NDF to undergo tyrosine phosphorylation (Peles et al. (1993) EMBO J. 12:961–971). This indicated that another cellular component was necessary for conferring full heregulin responsiveness. Carraway et al. subsequently demonstrated that $^{125}$I-rHRGβ1$_{177-244}$ bound to NIH-3T3 fibroblasts stably transfected with bovine erbB3 but not to non-transfected parental cells. Accordingly, they conclude that ErbB3 is a receptor for HRG and mediates phosphorylation of intrinsic tyrosine residues as well as phosphorylation of ErbB2 receptor in cells which express both receptors. Caraway et al. (1994) J. Biol. Chem. 269(19):14303–14306. Sliwkowski et al. (1994) J. Biol. Chem. 269(20):14661–14665 found that cells transfected with HER3 alone show low affinities for heregulin, whereas cells transfected with both HER2 and HER3 show higher affinities.

This observation correlates with the "receptor cross-talking" described previously by Kokai et al., Cell 58:287–292 (1989); Stern et al. (1988) EMBO J. 7:995–1001; and King et al., 4:13–18 (1989). These researchers found that binding of EGF to the EGFR resulted in activation of the EGFR kinase domain and cross-phosphorylation of p185$^{HER2}$. This is believed to be a result of ligand-induced receptor heterodimerization and the concomitant cross-phosphorylation of the receptors within the heterodimer (Wada et al. (1990) Cell 61:1339–1347).

Plowman and his colleagues have similarly studied p185$^{HER4}$/p185$^{HER2}$ activation. They expressed p185$^{HER2}$ alone, p185$^{HER4}$ alone, or the two receptors together in human T lymphocytes and demonstrated that heregulin is capable of stimulating tyrosine phosphorylation of p185$^{HER4}$, but could only stimulate p185$^{HER2}$ phosphorylation in cells expressing both receptors. Plowman et al., Nature 336:473–475 (1993). Thus, heregulin is the only known example of a member of the EGF growth factor family that can interact with several receptors. Carraway and Cantley (1994) Cell 78:5–8.

The biological role of heregulin has been investigated by several groups. For example, Falls et al., (discussed above) found that ARIA plays a role in myotube differentiation, namely affecting the synthesis and concentration of neurotransmitter receptors in the postsynaptic muscle cells of motor neurons. Corfas and Fischbach demonstrated that ARIA also increases the number of sodium channels in chick muscle. Corfas and Fischbach (1993) J. Neuroscience 13(5): 2118–2125. It has also been shown that GGFII is mitogenic for subconfluent quiescent human myoblasts and that differentiation of clonal human myoblasts in the continuous presence of GGFII results in greater numbers of myotubes after six days of differentiation (Sklar et al. (1994) J. Cell Biochem., Abst. W462, 18D, 540). See also WO 94/26298 published Nov. 24, 1994.

Holmes et al., supra, found that HRG exerted a mitogenic effect on mammary cell lines (such as SK-BR-3 and MCF-7). The mitogenic activity of GGFs on Schwann cells has also been reported. See, e.g., Brockes et al. (1980) J. Biol. Chem. 255(18):8374–8377; Lemke and Brockes (1984) J. Neurosci. 4:75–83; Brockes et al. (1984) J. Neuroscience 4(1):75–83; Brockes et al. (1986) Ann. Neurol. 20(3):317–322; Brockes, J. (1987) Methods in Enzym. 147:217–225 and Marchionni et al., supra. Schwann cells constitute important glial cells which provide myelin sheathing around the axons of neurons, thereby forming individual nerve fibers. Thus, it is apparent that Schwann cells play an important role in the development, function and regeneration of peripheral nerves. The implications of this from a therapeutic standpoint have been addressed by Levi et al. (1994) J. Neuroscience 14(3):1309–1319. Levi et al. discuss the potential for construction of a cellular prosthesis comprising human Schwann cells which could be transplanted into areas of damaged spinal cord. Methods for culturing Schwann cells ex vivo have been described. See WO 94/00140 and Li et al. (1996) J. Neuroscience 16(6):2012–2019.

Pinkas-Kramarski et al. found that NDF seems to be expressed in neurons and glial cells in embryonic and adult rat brain and primary cultures of rat brain cells, and suggested that it may act as a survival and maturation factor for astrocytes (Pinkas-Kramarski et al. (1994) PNAS, USA 91:9387–9391). Meyer and Birchmeier (1994) PNAS, USA 91:1064–1068 analyzed expression of heregulin during mouse embryogenesis and in the perinatal animal using in situ hybridization and RNase protection experiments. These authors conclude that, based on expression of this molecule, heregulin plays a role in vivo as a mesenchymal and neuronal factor. Also, their findings imply that heregulin functions in the development of epithelia. Similarly, Danilenko et al. (1994) Abstract 3101, FASEB 8(4–5):A535, found that the interaction of NDF and the HER2 receptor is important in directing epidermal migration and differentiation during wound repair.

Although NRG1 was initially proposed to be the ligand for the receptor tyrosine kinase ErbB2, further studies have demonstrated that activation of ErbB2 frequently occurred as a result of NRG1 binding to ErbB3 (Sliwkowski, M. X., et al. (1994) J. Biol. Chem. 269:14661–14665) or ErbB4 (Plowman, G. D. et al. (1993) Nature 366:473–475; and Carraway, K. L. and Cantley, L. C. (1994) Cell 78:5–8) receptors. Recent studies have begun to highlight the roles of NRG1, ErbB2 receptor and ErbB4 receptor in the development of the heart. Mice lacking ErbB4 receptor, ErbB2 receptor or NRG1 die during mid-embryogenesis (embryonic day 10.5) from the aborted development of myocardial trabeculae in the ventricle (Meyer & Birchmeier (1995) Nature 378:386–90; Gassmann et al. (1995) Nature 378: 390–4; and Lee et al. (1995) Nature 378:394–8). These results are consistent with the view that NRG1, expressed in the endocardium, is an important ligand required for the activation of ErbB2 and ErbB4 receptors in the myocardium.

These same studies suggest that NRG1 and ErbB2 receptor may play a different role than ErbB4 receptor in the development of the hind brain. NRG1 is expressed in the neuroepithelium and cells arising from rhombomeres 2, 4 and 6, while ErbB4 receptor is expressed in rhombomeres 3 and 5. NRG1 and ErbB2 receptor knockout mice exhibit a loss of cells and axons of the cranial sensory ganglia. In contrast, ErbB4 receptor deficient mice do not exhibit a loss of cellularity in the cranial ganglia. Rather, the organization, spacing and pattern of innervation of these ganglia to and from the central nervous system is disrupted (Gassmann et al., supra). One possible reason for this difference in hindbrain phenotypes of NRG1 and ErbB4 receptor knockout mice is that additional ligand(s) distinct from NRG1 may be recognized by ErbB4 in the CNS (Gassmann et al., supra).

SUMMARY OF THE INVENTION

The present invention is based on the identification, recombinant production and characterization of a novel member of the family of neuregulins (NRG1). More specifically, the invention concerns a novel polypeptide, NRG3, comprising an EGF-like domain distinct from EGF-like domains of NRG1 and NRG2. In addition, the NRG3 disclosed herein displays distinct receptor binding characteristics relative to other neuregulin-like polypeptides.

In analyzing the homologous sequence motif, homology to the EGF-like domain of NRG1 was observed in the subset of amino acids that are conserved in most neuregulins. Based upon this observation and the observed ErbB4 receptor binding characteristics, the novel protein, NRG3, has been identified as a new member of the family of neuregulins. The novel protein contains domains that are distantly related to, but distinct from, those found in the other members of the NRG1 family. In addition, it is expressed primarily in embryonic and adult tissues of the central nervous system. NRG3 represents a novel member of the neuregulin family of compounds, members of which are involved in cell proliferation and differentiation, epithelial development, cardiac development, neurological development, as well as acting as glial cell mitogens, and as mesenchymal and neuronal factors.

In one aspect, the present invention concerns a novel isolated mammalian NRG3 polypeptide having an EGF-like domain, and functional derivatives of the novel NRG3, which polypeptides bind the ErbB4 receptor. The native polypeptides within the scope of the present invention are characterized as containing an extracellular domain including an EGF-like domain, a transmembrane domain and a cytoplasmic domain. The present invention specifically includes the soluble forms of the novel NRG3 ligand molecules of the invention, which have a transmembrane domain that cannot associate with a cell membrane, and optionally devoid of all or part of the cytoplasmic domain. By "transmembrane domain" is meant a domain of the polypeptide that contains a sufficient number of hydrophobic amino acids to allow the polypeptide to insert and anchor in a cell membrane. By "transmembrane domain that cannot associate with a cell membrane" is meant a transmembrane domain that has been altered by mutation or deletion such that is insufficiently hydrophobic to allow insertion or other association with a cell membrane. Such a transmembrane domain does not preclude, for example, the fusion of the NRG3 of the invention, or fragment thereof, with a secretion signal sequence useful for secretion of the polypeptide from the cell, an insufficient number of hydrophobic amino acid side chains are present devoid of an active transmembrane domain does not insert into a cell membrane. Mutations or alterations of the amino acid sequence useful to achieve an inactive transmembrane domain include, but are not limited to, deletion or substitution of amino acids within the transmembrane domain.

In a particular embodiment, the invention concerns isolated polypeptides, preferably NRG3 ligands, having at least 75% amino acid identity to polypeptides selected from the group consisting of
  (1) a polypeptide comprising the amino acid sequence encoding the EGF-like domain shown in FIG. 3 (SEQ ID NO:4);
  (2) a polypeptide comprising the amino acid sequence encoding the extracellular domain of mouse or human NRG3 shown in FIG. 3 (SEQ ID NO: 3 or SEQ ID NO:7, respectively);
  (3) a polypeptide comprising the amino acid sequence of the native mouse or human NRG3 polypeptide shown in FIG. 3 (SEQ ID NO: 2 and SEQ ID NO:6, respectfully);
  (4) a further mammalian homologue of polypeptide (1)–(3);
  (5) a soluble form of any of the polypeptides (1)–(4) devoid of an active transmembrane domain; and
  (6) a derivative of any of the polypeptides (1)–(5), retaining the qualitative EGF-like domain and NRG3 receptor binding properties of a polypeptide (1)–(5).

While the native NRG3 polypeptides of the present invention are glycoproteins, the present invention also encompasses variant molecules unaccompanied by native glycosylation or having a variant glycosylation pattern. Preferably, the EGF-like domain of the NRG3 polypeptide is unglycosylated.

In a further embodiment, the invention includes an antagonist of a novel NRG3 of the present invention. The antagonist of the invention may be a peptide that binds an NRG3 such as an anti-NRG3 antibody or binding fragment thereof. Preferably, the NRG3 antagonist of the invention substantially reduces binding of a natural ErbB4 receptor ligand, such as an NRG3, to the ErbB4 receptor, thereby preventing or limiting activation of the receptor. In a preferred embodiment, the antagonist reduces NRG3 binding to its receptor to less than 50%, preferably less than 20%, most preferably less than 10% of the binding of an NRG3 under like conditions.

In yet another embodiment, the invention includes an agonist of a novel NRG3 of the present invention. The agonist of the invention may be a NRG3, or it may be an anti-NRG3 receptor antibody or receptor binding fragment. An agonist NRG3 of the invention may also be an polypeptide encoded by an alternatively spliced form of the native NRG3-encoding gene, preferably comprising the NRG3 EGF-like domain disclosed herein. In an embodiment of the agonist of the invention, the NRG3 agonist is an anti-ErbB4 receptor antibody, which antibody binds to and activates the ErbB4 receptor. Preferably, the binding affinity of the agonist is at least 25% of the affinity of the native ligand, more preferably at least 50%, and most preferably at least 90% of the affinity of the native ligand. Similarly, it is preferred that the agonist of the invention activate the ErbB4 receptor at the level of at least 25%, more preferably at least 50%, most preferably at least 90% of activation of the native NRG3.

The invention further concerns a nucleic acid molecule encoding a novel NRG3 of the present invention, vectors containing such nucleic acid, and host cells transformed with the vectors. The nucleic acid preferably encodes at least the EGF-like domain of a native or variant ErbB4 receptor-specific NRG3 of the present invention. The invention further includes nucleic acids hybridizing under stringent conditions to the complement of a nucleic acid encoding a native ErbB4 receptor-specific NRG3 of the present invention, and encoding a protein retaining the qualitative ErbB4 receptor-specific binding properties of a native NRG3 disclosed herein. In addition, the invention includes a nucleic acid deposited with the American Type Culture Collection as ATCC 209156 (pLXSN.mNRG3), which nucleic acid is an expression vector comprising nucleic acid encoding the mouse NRG3 open reading frame (SEQ ID NO:1). The invention also includes a nucleic acid deposited with the American Type Culture Collection as ATCC 209157 (pRK5.tk.neo.hNRG3B1), which nucleic acid is an expression vector comprising nucleic acid encoding a human NRG3 nucleic acid (SEQ ID NO:5). The invention also includes a nucleic acid deposited with the American Type Culture Collection as ATCC 209297 (pRK5.tk.neo.hNRG3B2), which nucleic acid is an expression vector comprising nucleic acid encoding an alternatively spliced form of human NRG3 nucleic acid (SEQ ID NO:22) lacking nucleic acids 1585 to 1656 of SEQ ID NO:5. The deduced amino acid sequence of the alternatively spliced human NRG3B2 is found in SEQ ID NO:23 which lacks amino acids 529 to 552 of SEQ ID NO:6. A comparison of the hNRG3B1 and hNRG3B2 amino acid sequences is shown in FIG. 4B. The invention further includes NRG3 amino acid sequences of mouse and human NRG3, alternatively spliced forms or fragments thereof, encoded by the deposited expression vectors.

In another aspect, the invention concerns a process for producing a NRG3 of the invention, which process comprises transforming a host cell with nucleic acid encoding the desired NRG3, culturing the transformed host cell and recovering the NRG3 produced from the host cell or host cell culture.

As an alternative to production of the NRG3 in a transformed host cell, the invention provides a method for producing NRG3 comprising: (a) transforming a cell containing an endogenous NRG3 gene with a homologous DNA comprising an amplifiable gene and a flanking sequence of at least about 150 base pairs that is homologous with a DNA sequence within or in proximity to the endogenous NRG3 gene, whereby the homologous DNA integrates into the cell genome by recombination; (b) culturing the cell under conditions that select for amplification of the amplifiable gene, whereby the NRG3 gene is also amplified; and thereafter (c) recovering NRG3 from the cell.

In a further aspect, the invention concerns an antibody that binds specifically to a NRG3 of the present invention, and to a hybridoma cell line producing such an antibody.

In a still further aspect, the invention concerns an immunoadhesin comprising a novel NRG3 sequence, as disclosed herein, fused to an immunoglobulin sequence. The NRG3 sequence is preferably a transmembrane-domain-deleted form of a native or variant polypeptide fused to an immunoglobulin constant domain sequence, and comprises at least the EGF-like domain of the extracellular domain of a native NRG3 of the present invention. In another preferred embodiment, the NRG3 sequence present in the immunoadhesin shows at least about 80% sequence homology with the extracellular domain of the sequence shown in SEQ ID NO:3 NRG3 or SEQ ID NO:7 for mouse or human NRG3, respectively. The immunoglobulin constant domain sequence preferably is that of an IgG-1, IgG-2 or IgG-3 molecule, but may also be an IgA or IgM molecule.

In a further aspect, the invention encompasses a transgenic animal comprising an altered NRG3 gene in which the polypeptide encoded by the altered gene is not biologically active (non-functional), deleted, or has no more than 70% wild type activity, preferably no more that 50% activity and more preferably no more than 25% activity of the native NRG3 polypeptide. In addition, a transgenic animal of the invention includes a transgenic animal comprising and expressing a native NRG3, alternatively spliced form of NRG3, or a fragment or variant thereof. Such transgenic animals are useful for the screening of potential NRG3 agonists and antagonists.

The invention further concerns pharmaceutical compositions comprising a NRG3 as hereinabove defined in admixture with a pharmaceutically acceptable carrier. Dosages and administration of NRG3 in a pharmaceutical composition may be determined by one of ordinary skill in the art of clinical pharmacology or pharmacokinetics (see, for example, Mordenti, J. and Rescigno, A. (1992) Pharmaceutical Research 9:17–25; Morenti, J. et al. (1991) Pharmaceutical Research 8:1351–1359; and Mordenti, J. and Chappell, W. (1989) "The use of interspecies scaling in toxicokinetics" in *Toxicokinetics and New Drug Development*, Yacobi et al. (eds), Pergamon Press, NY, pp. 42–96, each of which references are herein incorporated by reference in its entirety).

In an aspect of the invention, the isolated nucleic acid encoding the NRG3 of the invention, or fragment thereof, may also be used for in vivo or ex vivo gene therapy.

In an embodiment of the invention, a nucleic acid sequence encoding an NRG3, or fragment or variant thereof, is introduced into a cell of an animal as part of an expression cassette such that the NRG3-encoding nucleic acid sequence is expressed in the cell. Preferably, the NRG3 encoding nucleic acid sequence comprises sequences (such as a promotor sequence) for the control of NRG3 expression within the cell. Preferably, the expression cassette comprises a retroviral vector for delivery of the nucleic acid sequence to a cell of the animal.

In a further embodiment of the invention, a host cell expressing an NRG3 or NRG3 agonist is introduced into an animal, preferably a human, such that NRG3 or NRG3 agonist produced by the host cell is effective in treating a disorder responsive to increased local or systemic NRG3 administration. Cells genetically engineered to express an NRG3, fragment or variant thereof, can be implanted in the host to provide effective levels of factor or factors. The cells can be prepared, encapsulated, and implanted as provided in U.S. Pat. Nos. 4,892,538, and 5,011,472, WO 92/19195, WO 95/05452, or Aebischer et al. (1996) Nature Medicine 2:696–699, for example, which references are herein incorporated by reference in their entirety.

The present invention includes methods of enhancing survival, proliferation or differentiation of cells comprising the ErbB4 receptor in vivo and in vitro. Normally, the cells will be treated with the NRG3 polypeptide or fragment or variant thereof. However, gene therapy approaches have been described in the art and are encompassed by the present invention. These techniques include gene delivery to a cell using adenovirus, herpes simplex I virus or adeno-associated virus as well as lipid-based delivery systems (e.g. liposomes). Retroviruses are useful for ex vivo gene therapy approaches. Accordingly, it is possible to administer the nucleic acid encoding NRG3, resulting in expression of the NRG3 polypeptide, fragment or variant in the patient or in tissue culture. For exemplary gene therapy techniques see WO 93/25673 and the references cited therein.

An aspect of the invention is a method of treating a disorder by administering to a mammal a cell encoding an NRG3 or fragment thereof, or agonist or antagonist of the NRG3 as necessary to treat the disorder, which cell secretes the NRG3 of the invention. An embodiment of the invention is a method for preventing or treating damage to a nerve or damage to other NRG3-expressing or NRG3-responsive cells, e.g. brain, heart, or kidney cells, which method comprises implanting cells that secrete NRG3, or fragment or agonist thereof, or antagonist as may be required for the particular condition, into the body of patients in need thereof.

A further embodiment of the invention includes an implantation device, for preventing or treating nerve damage or damage to other cells as taught herein, containing a semipermeable membrane and a cell that secretes NRG3, or fragment or agonist thereof, (or antagonist as may be required for the particular condition) encapsulated within the membrane, the membrane being permeable to NRG3, or fragment agonist thereof, and impermeable to factors from the patient detrimental to the cells. The patient's own cells, transformed to produce NRG3 ex vivo, could be implanted directly into the patient, optionally without such encapsulation. The methodology for the membrane encapsulation of living cells is familiar to those of ordinary skill in the art, and the preparation of the encapsulated cells and their implantation in patients may be accomplished readily as is known in the art.

In accordance with the in vitro methods of the invention, cells comprising the ErbB4 receptor are placed in a cell culture medium. Examples of ErbB4-receptor-containing cells include neural cells, e.g., brain cells (such as neurons of the neocortex, cerebellum and hippocampus); cardiac cells; skeletal and smooth muscle cells; and cultured cells transformed with a recombinant NRG3.

Suitable tissue culture media are well known to persons skilled in the art and include, but are not limited to, Minimal Essential Medium (MEM), RPMI-1640, and Dulbecco's Modified Eagle's Medium (DMEM). These tissue culture medias are commercially available from Sigma Chemical Company (St. Louis, Mo.) and GIBCO (Grand Island, N.Y.). The cells are then cultured in the cell culture medium under conditions sufficient for the cells to remain viable and grow in the presence of an effective amount of NRG3. The cells can be cultured in a variety of ways, including culturing in a clot, agar, or liquid culture.

The cells are cultured at a physiologically acceptable temperature such as 37° C., for example, in the presence of an effective amount of NRG3, fragment or variant. The amount of NRG3 may vary, but preferably is in the range of about 0.1 ng/ml to about 1 mg/ml preferably about 0.1 ng/ml to about 0.1 ng/ml. The NRG3 can of course be added to the culture at a dose determined empirically by those in the art without undue experimentation. The concentration of NRG3 in the culture will depend on various factors, such as the conditions under which the cells and NRG3 are cultured. The specific temperature and duration of incubation, as well as other culture conditions, can be varied depending on such factors as, e.g., the concentration of the NRG3, and the type of cells and medium. Those skilled in the art will be able to determine operative and optimal culture conditions without undue experimentation. Proliferation, differentiation and/or survival of the cells (e.g. neurons) in the cultures can be determined by various assays known in the art such as those described above.

It is contemplated that using NRG3 to enhance cell survival, growth and/or differentiation in vitro will be useful in a variety of ways. For instance, neural cells cultured in vitro in the presence of NRG3 can be infused into a mammal suffering from reduced levels of the cells. Stable in vitro cultures can also be used for isolating cell-specific factors and for expression of endogenous or recombinantly introduced proteins in the cell. NRG3, fragments or variants thereof may also be used to enhance cell survival, proliferation and/or differentiation of cells which support the growth and/or differentiation of other cells in cell culture.

The invention also provides in vivo uses for NRG3. Based on the neuronal cell expression pattern of NRG3, it is believed that this molecule will be particularly useful for treating diseases which involve neural cell growth such as demyelination, or damage or loss of glial cells (e.g. multiple sclerosis).

The invention further provides a method for treating a mammal comprising administering a therapeutically effective amount of NRG3, NRG3 fragment, or NRG3 agonist to the mammal. For example, the mammal may be suffering from a neurological or muscular disorder. Where the disorder is a neurological disorder, NRG3 is believed to be useful in promoting the development, maintenance, and/or regeneration of neurons in vivo, including central (brain and spinal chord), peripheral (sympathetic, parasympathetic, sensory, and enteric neurons), and motoneurons. Accordingly, NRG3 may be utilized in methods for the diagnosis and/or treatment of a variety of neurologic diseases or disorders which affect the nervous system of a mammal, such as a human.

Such diseases or disorders may arise in a patient in whom the nervous system has been damaged by, e.g., trauma, surgery, stroke, ischemia, infection, metabolic disease, nutritional deficiency, malignancy, or toxic agents. The agent is designed to promote the survival or growth of neurons. For example, NRG3 can be used to promote the survival or growth of motoneurons that are damaged by trauma or surgery. Also, NRG3 can be used to treat motoneuron disorders, such as amyotrophic lateral sclerosis (Lou Gehrig's disease), Bell's palsy, and various conditions involving spinal muscular atrophy, or paralysis. NRG3 can be used to treat human "neurodegenerative disorders", such as Alzheimer's disease, Parkinson's disease, epilepsy, multiple sclerosis, Huntington's chorea, Down's Syndrome, nerve deafness, and Meniere's disease.

Further, NRG3 can be used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine.

The invention further provides a method for treating a mammal comprising administering a therapeutically effective amount of a NRG3 antagonist to the mammal. The mammal in this latter case is one which could benefit from a reduction in NRG3 levels/biological activity.

These and other objects, advantages and features of the present invention will become apparent to those persons skilled in the art upon reading the details of the structure, synthesis, and usage as more fully set forth below. Each reference cited herein is herein incorporated by reference in its entirety with particular attention to the description of subject matter associated with the context of the citation.

BRIEF DESCRIPTION OF THE DRAWINGS

FIG. 1 shows the nucleic acid coding sequence of mouse NRG3 cDNA (mNRG3, SEQ ID NO:1) in which the start (ATG) and stop (TGA) codons of the coding sequence are indicated by underlining.

FIG. 2 shows the nucleic acid coding sequence of human NRG3 cDNA (hNRG3B1, SEQ ID NO:5) in which the start (ATG) and stop (TGA) codons of the coding sequence are indicated by underlining.

FIG. 3 shows the nucleic acid coding sequence of an alternatively spliced form of human NRG3 cDNA (hNRG3B2; SEQ ID NO:22) in which the start (ATG) and stop (TGA) codons of the coding sequence are indicated by underlining.

FIGS. 4A–4B. FIG. 4A shows the deduced amino acid sequences from mouse (mNRG3) and human (hNRG3B1) cDNA as shown in FIGS. 1 and 2. Mouse NRG3 deduced amino acid sequence is depicted by SEQ ID NO:2 and human NRG3B1 deduced amino acid sequence is depicted by SEQ ID NO:6. Various putative domains within the amino acid sequences are shown. The EGF-like domain, the N-terminal hydrophobic segment (double underline), the serine/threonine-rich portion, and a predicted transmembrane domain (single underline) are highlighted. FIG. 4B shows the deduced amino acid sequences from hNRG3B1 and hNRG3B2 cDNA as shown in FIGS. 2 and 3. Human NRGB1 deduced amino acid sequence is depicted by SEQ ID NO:6 and human NRG3B2 deduced amino acid sequence is depicted by SEQ ID NO:23. The region of the NRG3 amino acid sequence that differs between the two human sequences is illustrated.

FIG. 5 shows a sequence alignment of the EGF-like domains of human NRG3B1 (hNRG3.egf; SEQ ID NO:4); chicken ARIA (cARIA.egf; SEQ ID NO:9); human amphiregulin (hAR.egf; SEQ ID NO:10); human betacellulin (hBTC.egf; SEQ ID NO:11); human EGF (hEGF.egf; SEQ ID NO:12); human heparin-binding EGF-like growth factor (hHB-EGF.egf; SEQ ID NO:13); human heregulin-α (hHRGα; SEQ ID NO:14); human heregulin-β (hHRGβ.egf; SEQ ID NO:15); human TGF-α (hTGFα.egf; SEQ ID NO:16); and mouse epiregulin (mEPR.egf; SEQ ID NO:17). The sequences were analyzed using Sequence Analysis Programs, Genentech, Inc.

In FIGS. 6A–6D, parental K562 cells (FIG. 6A) or K562 cells expressing either ErbB2 receptor ($K562^{erbB2}$ cells; FIG. 6B), ErbB3 receptor ($K562^{erbB3}$ cells; FIG. 6C) or ErbB4 receptor ($K562^{erbB4}$ cells; FIG. 6D) were examined for the expression of corresponding receptors. Cells were incubated with anti-ErbB2 receptor, anti-ErbB3 receptor or anti-ErbB4 receptor antibodies as indicated before PE-conjugated secondary antibody was added. "LOG PE" represents relative fluorescent intensity and "Counts" represents cell numbers. In FIGS. 6E–6H, $NRG3^{EGF}$.Fc is shown by FACS analysis to bind to ErbB4 receptor expressing cells. Parental K562 cells (FIG. 6E), $K562^{erbB2}$ cells (FIG. 6F), $K562^{erbB3}$ cells (FIG. 6G) and $K562^{erbB4}$ cells (FIG. 6H) were incubated with or without $NRG3^{EGF}$.Fc (containing gD tag) for 1 hour, followed by anti-gD-tag primary antibody and PE-conjugated secondary antibody.

Figure 6A:
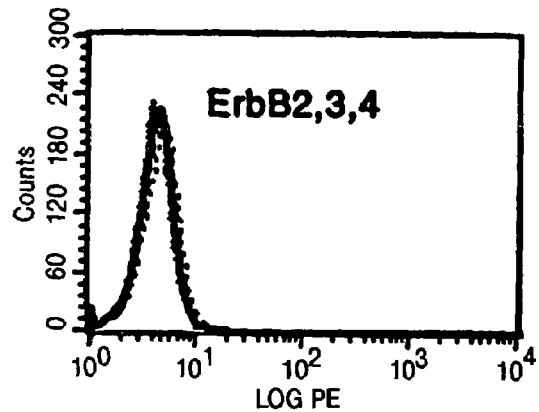
FIGS. 6A–6H are FACS plots demonstrating binding of $NRG3^{EGF}$.Fc to ErbB4 receptor expressed on the surface of cells.

Before the present polypeptides, nucleic acids, vectors, and host cells and processes for making such are described, it is to be understood that this invention is not limited to the particular compositions of matter and processes described, as such compounds and methods may, of course, vary. It is also to be understood that the terminology used herein is for the purpose of describing particular embodiments only, and is not intended to be limiting since the scope of the present invention will be limited only by the appended claims.

DESCRIPTION OF THE EMBODIMENTS

Definitions

The phrases "novel neuregulin related ligand", "novel NRG3", "novel ErbB4 receptor-specific NRG3" are used interchangeably and refer to a new member of the family of neuregulins, which NRG3 is expressed specifically in the brain and nervous system of the embryo and adults, and to functional derivatives of such native polypeptides.

The term "NRG3" or "neuregulin related ligand" is defined herein to be any polypeptide sequence that possesses at least one biological property (as defined below) of native amino acid sequence NRG3 of SEQ ID NO:2 or 6 (mouse or human, respectively) and additionally includes an alternatively spliced form of human NRG3 having the amino acid sequence of SEQ ID NO:23. This definition encompasses not only the polypeptide isolated from a native NRG3 source such as human MDA-MB-175 cells or from another source, such as another animal species or alternatively spliced forms of NRG3, but also the polypeptide prepared by recombinant or synthetic methods. It also includes variant forms including functional derivatives, allelic variants, naturally occurring isoforms and analogues thereof. Sometimes the NRG3 is "native NRG3" which refers to endogenous NRG3 polypeptide which has been isolated from a mammal. The NRG3 can also be "native sequence NRG3" insofar as it has the same amino acid sequence as a native NRG3 (e.g. mouse (SEQ ID NO:2) or human (SEQ ID NO:6 or SEQ ID NO:23) NRG3 shown in FIGS. 4A and 4B). However, "native sequence NRG3" encompasses the polypeptide produced by recombinant or synthetic means. "Mature NRG3" is soluble or secreted NRG3 released from the cell (i.e. lacking an N-terminal hydrophobic sequence). In this context, NRG3 refers to novel NRG3s comprising an EGF-like domain within an extracellular domain, a transmembrane domain and a cytoplasmic domain, with or without a native signal sequence, and naturally occurring soluble forms of such NRG3s, with or without the initiating methionine, whether purified from native source, synthesized, produced by recombinant DNA technology or by any combination of these and/or other methods. The native NRG3s of the present invention specifically include the murine NRG3, the amino acid sequence of which is shown in FIG. 4 (SEQ. ID. NO:2), and the human NRG3s having the amino acid sequences shown in FIG. 4 (SEQ. ID. NO:6 or SEQ ID NO:23), and fragments or mammalian homologues or alternatively spliced forms of these native ligands. The novel native murine and human NRG3s of the present invention are about 713 and 720 amino acids in length, respectively, and comprise an EGF-like domain, the N-terminal hydrophobic segment, the serine/threonine-rich portion, a predicted transmembrane domain, and a predicted intracellular domain. The boundaries of these domain are indicated in FIG. 4 for the novel murine and human NRG3 sequences.

Optionally, the NRG3 is not associated with native glycosylation. "Native glycosylation" refers to the carbohydrate moieties which are covalently attached to native NRG3 when it is produced in the mammalian cell from which the native NRG3 is derived. Accordingly, human NRG3 produced in a non-human could be described as not being associated with native glycosylation, for example it may be glycosylated other than the native glycosylation. Sometimes, the NRG3 is not associated with any glycosylation whatsoever (e.g. as a result of being produced recombinantly in a prokaryote).

The term "EGF-like domain" refers to an extracellular epidermal growth factor (EGF)-like domain of a polypeptide, preferably a NRG3 polypeptide of the invention. The EGF-like domain is sufficient to bind neuregulin receptors and stimulate cellular responses (Holmes, W. E., et al. (1992) Science 256:1205–1210). Preferably, an EGF-like domain of the NRG3 of the invention has the amino acid sequence of the NRG3s shown in SEQ ID NO:4 (mouse or human NRG3 EGF-like domain), where the EGF-like domain is from about amino acid 284 to about amino acid 332 of human NRG3, and from about amino acid 286 to about amino acid 334 of mouse NRG3. The NRG3 of the invention encompasses a polypeptide encoded by an alternatively spliced form the NRG3 encoding gene, which alternatively spliced form comprises the NRG3 EGF-like domain.

The term "ErbB" when used herein refers to any one or more of the mammalian ErbB receptors (i.e. ErbB 1 or epidermal growth factor (EGF) receptor; ErbB2 or HER2 receptor; ErbB3 or HER3 receptor; ErbB4 or HER4 receptor; and any other member(s) of this class I tyrosine kinase family to be identified in the future) and "erbB" refers to the mammalian erbB genes encoding these receptors.

The terms "soluble form", "soluble receptor", "soluble NRG3", "soluble NRG3", and grammatical variants thereof, refer to variants of the native or variant NRG3s of the present invention which are devoid of a functional transmembrane domain. In the soluble receptors the transmembrane domain may be deleted, truncated or otherwise inactivated such that they are not capable of cell membrane anchorage. If desired, such soluble forms of the NRG3s of the present invention might additionally have their cytoplasmic domains fully or partially deleted or otherwise inactivated.

A "functional derivative" of a polypeptide is a compound having a qualitative biological activity in common with the native polypeptide. Thus, a functional derivative of a native novel NRG3 of the present invention is a compound that has a qualitative biological activity in common with such native NRG3. "Functional derivatives" include, but are not limited to, fragments of native polypeptides from any animal species (including humans), derivatives of native (human and non-human) polypeptides and their fragments, and peptide and non-peptide analogs of native polypeptides, provided that they have a biological activity in common with a respective native polypeptide.

As used herein, the term "fragments" refers to regions within the sequence of a mature native polypeptide. Preferably NRG3 fragments will have a consecutive sequence of at least 20, and more preferably at least 50, amino acid residues of the EGF-like domain of NRG3. The preferred fragments have about 30–150 amino acid residues which are identical to a portion of the sequence of NRG3 in SEQ ID NO:2 (from mouse), or in SEQ ID NO:6 or SEQ ID NO:23 (from human). The term "derivative" is used to define amino acid sequence and glycosylation variants, and covalent modifications of a native polypeptide. "Non-peptide analogs" are organic compounds which display substantially the same surface as peptide analogs of the native polypeptides. Thus, the non-peptide analogs of the native novel NRG3s of the present invention are organic compounds which display substantially the same surface as peptide analogs of the native NRG3s. Such compounds interact with other molecules in a similar fashion as the peptide analogs, and mimic a biological activity of a native NRG3 of the present invention. Preferably, amino acid sequence variants of the present invention retain at least one domain of a native NRG3, preferably an EGF-like domain, or have at least about 60% amino acid sequence identity, more preferably at least about 75% amino acid sequence identity, and most preferably at least about 90% amino acid sequence identity with a domain of a native NRG3 of the present invention. The amino acid sequence variants preferably show the highest degree of amino acid sequence homology with the EGF-like domain of native NRG3s of the present invention. These are the domains which show the highest percentage amino acid conservation between the novel NRG3s of the present invention and other members of the NRG3 family (see FIG. 4).

The terms "isolated" or "substantially pure" refer to a polypeptide or nucleic acid which is free of other polypeptides or nucleic acids as well as lipids, carbohydrates or other materials with which it is naturally associated. An exception is made for glycosylation wherein sugar moieties are covalently attached to amino acids of the NRG3 polypeptide of the invention. One of ordinary skill in the art can purify a NRG3 polypeptide or nucleic acid encoding the polypeptide using standard techniques appropriate for each type of molecule.

The term "percent amino acid sequence identity" with respect to the NRG3 sequence is defined herein as the percentage of amino acid residues in the candidate sequence that are identical with the residues in the NRG3 sequence having the deduced amino acid sequence described in FIG. 1, after aligning the sequences and introducing gaps, if necessary, to achieve the maximum percent sequence identity, and not considering any conservative substitutions as part of the sequence identity. N-terminal, C-terminal, or internal extensions, deletions, or insertions into the NRG3 sequence shall be construed as affecting sequence identity or homology.

Another type of NRG3 variant is "chimeric NRG3", which term encompasses a polypeptide comprising full-length NRG3 or a fragment thereof fused or bonded to a heterologous polypeptide. The chimera will normally share at least one biological property with NRG3. Examples of chimeric NRG3s include immunoadhesins and epitope tagged NRG3. In another embodiment, the heterologous polypeptide is thioredoxin, a salvage receptor binding epitope, cytotoxic polypeptide or enzyme (e.g., one which converts a prodrug to an active drug).

The terms "covalent modification" and "covalent derivatives" are used interchangeably and include, but are not limited to, modifications of a native polypeptide or a fragment thereof with an organic proteinaceous or non-proteinaceous derivatizing agent, fusions to heterologous polypeptide sequences, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl, tyrosyl or threonyl residues, methylation of the α-amino groups of lysine, arginine, and histidine side chains (T. E. Creighton (1983) *Proteins: Structure and Molecular Properties*, W.H. Freeman & Co., San Francisco, pp. 79–86). Covalent derivatives/modifications specifically include fusion proteins comprising native NRG3 sequences of the present invention and their amino acid sequence variants, such as immunoadhesins, and N-terminal fusions to heterologous signal sequences.

The term "biological activity" in the context of the present invention is defined as the possession of at least one adhesive, regulatory or effector function qualitatively in common with a native polypeptide. Preferred functional derivatives within the scope of the present invention are unified by retaining an EGF-like domain and ErbB4 receptor-specific binding of a native NRG3 of the present invention.

The phrase "activating an ErbB receptor" refers to the act of causing the intracellular kinase domain of an ErbB receptor to phosphorylate tyrosine residues. Generally, this will involve binding of NRG3 to an ErbB4 receptor or ErbB4 receptor homodimer, which binding activates a kinase domain of one or more of the receptors and thereby results in phosphorylation of tyrosine residues in one or more of the receptors, and/or phosphorylation of tyrosine residues in additional substrate polypeptide(s). ErbB receptor phosphorylation can be quantified using the tyrosine phosphorylation assays described below. It is understood that the NRG3 of the invention may itself be activated by interaction with an ErbB receptor via the intracellular domain of NRG3. Thus, an NRG3-activating ligand that binds to the NRG3 (preferably binding to the extracellular domain, more preferably the EGF-like domain) includes, but is not limited to, a ligand, an antibody, or a receptor. Activation of the NRG3 may be through phosphorylation of the intracellular domain or other like event common to receptor/ligand mediated cell signaling. As a mediator of cell signaling, the NRG3 of the invention is expected to be associated with apoptosis, metabolic signaling, differentiation or cell proliferation.

"Identity" or "homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art. For example, the sequences disclosed herein were analyzed using Sequence Analysis Programs, Genentech, Inc, Inc.

The term "agonist" is used to refer to peptide and non-peptide analogs of the native NRG3s of the present invention and to antibodies specifically binding such native NRG3s provided that they retain at least one biological activity of a native NRG3. Preferably, the agonists of the present invention retain the qualitative EGF-like domain binding recognition properties of the native NRG3 polypeptides.

The term "antagonist" is used to refer to a molecule inhibiting a biological activity of a native NRG3 of the present invention. Preferably, the antagonists herein inhibit the binding of a native NRG3 of the present invention. Preferred antagonists essentially completely block the binding of a native NRG3 to an ErbB4 receptor to which it otherwise binds. A NRG3 "antagonist" is a molecule which prevents, or interferes with, a NRG3 effector function (e.g. a molecule which prevents or interferes with binding and/or activation of an ErbB4 receptor by NRG3). Such molecules can be screened for their ability to competitively inhibit ErbB receptor activation by NRG3 in the tyrosine phosphorylation assay disclosed herein, for example. Preferred antagonists are those which do not substantially interfere with the interaction of other heregulin polypeptides with ErbB receptor(s). Examples of NRG3 antagonists include neutralizing antibodies against NRG3 and antisense polynucleotides against the NRG3 gene.

Ordinarily, the terms "amino acid" and "amino acids" refer to all naturally occurring L-α-amino acids. In some embodiments, however, D-amino acids may be present in the polypeptides or peptides of the present invention in order to facilitate conformational restriction. For example, in order to facilitate disulfide bond formation and stability, a D amino acid cysteine may be provided at one or both termini of a peptide functional derivative or peptide antagonist of the native NRG3s of the present invention. The amino acids are identified by either the single-letter or three-letter designations:

| Asp | D | aspartic acid |
|-----|---|---------------|
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Ile | I | isoleucine |
| Leu | L | leucine |
| Tyr | Y | tyrosine |
| Phe | F | phenylalanine |
| His | H | histidine |
| Lys | K | lysine |
| Arg | R | arginine |
| Trp | W | tryptophan |
| Gln | Q | glutamine |
| Asn | N | asparagine |

The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed.

"Antibodies (Abs)" and "immunoglobulins (Igs)" are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al. (1985) J. Mol. Biol. 186, 651–663; Novotny and Haber (1985) Proc. Natl. Acad. Sci. USA 82:4592–4596).

The light chains of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein (1975) Nature 256:495, or may be made by recombinant DNA methods (see, e.g. U.S. Pat. No. 4,816, 567 (Cabilly et al.) and Mage and Lamoyi (1987) in *Monoclonal Antibody Production Techniques and Applications*, pp. 79–97, Marcel Dekker, Inc., New York). The monoclonal antibodies may also be isolated from phage libraries generated using the techniques described in McCafferty et al. (1990) Nature 348:552–554, for example.

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin. For further details see: Jones et al. (1986) Nature 321:522–525; Reichmann et al. (1988) Nature 332:323–329; EP-B-239 400 published 30 Sep. 1987; Presta (1992) Curr. Op. Struct. Biol. 2:593–596; and EP-B-451 216 published 24 Jan. 1996), which references are herein incorporated by reference in their entirety. The humanized antibody includes a Primatized™ antibody wherein the antigen-binding region of the antibody is derived from an antibody produced by immunizing macaque monkeys with the antigen of interest.

By "neutralizing antibody" is meant an antibody molecule as herein defined which is able to block or significantly reduce an effector function of native sequence NRG3. For example, a neutralizing antibody may inhibit or reduce the ability of NRG3 to activate an ErbB receptor, preferably an ErbB4 receptor, in the tyrosine phosphorylation assay described herein. The neutralizing antibody may also block the mitogenic activity of NRG3 in the cell proliferation assay disclosed herein.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.; Morrison et al. (1984) Proc. Natl. Acad. Sci. USA 81:6851–6855)).

In the context of the present invention the expressions "cell", "cell line", and "cell culture" and "host cell" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included. Methods of stable transfer, meaning that the foreign DNA is continuously maintained in the host, are known in the art.

The terms "replicable expression vector", "expression vector" and "vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

"Oligonucleotides" are short-length, single- or double-stranded polydeoxynucleotides that are chemically synthesized by known methods, such as phosphotriester, phosphite, or phosphoramidite chemistry, using solid phase techniques such as those described in EP 266,032, published 4 May 1988, or via deoxynucleoside H-phosphanate intermediates as described by Froehler et al. (1986) Nucl. Acids Res. 14:5399. They are then purified on polyacrylamide gels.

By "solid phase" is meant a non-aqueous matrix to which a reagent of interest (e.g., NRG3 or an antibody thereto) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149, herein incorporated by reference in its entirety.

The terms "transformation" and "transfection" are used interchangeably herein and refer to the process of introducing DNA into a cell. Following transformation or transfection, the NRG3 DNA may integrate into the host cell genome, or may exist as an extrachromosomal element. If prokaryotic cells or cells that contain substantial cell wall constructions are used as hosts, the preferred methods of transfection of the cells with DNA is the calcium treatment method described by Cohen et al. (1972) Proc. Natl. Acad. Sci. U.S.A., 69:2110–2114 or the polyethylene glycol method of Chung et al. (1988) Nuc. Acids. Res. 16:3580. If yeast are used as the host, transfection is generally accomplished using polyethylene glycol, as taught by Hinnen (1978) Proc. Natl. Acad. Sci. U.S.A. 75:1929–1933. If mammalian cells are used as host cells, transfection generally is carried out by the calcium phosphate precipitation method, Graham et al. (1978) Virology 52:546, Gorman et al. (1990) DNA and Protein Eng. Tech. 2:3–10. However, other known methods for introducing DNA into prokaryotic and eukaryotic cells, such as nuclear injection, electroporation, or protoplast fusion also are suitable for use in this invention.

Particularly useful in this invention are expression vectors that provide for the transient expression in mammalian cells of DNA encoding NRG3. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties.

It is further envisioned that the NRG3 of this invention may be produced by homologous recombination, as provided for in WO 91/06667, published 16 May 1991. Briefly, this method involves transforming a cell containing an endogenous NRG3 gene with a homologous DNA, which homologous DNA comprises (a) an amplifiable gene (e.g. a gene encoding dihydrofolate reductase (DHFR)), and (b) at least one flanking sequence, having a length of at least about 150 base pairs, which is homologous with a nucleotide sequence in the cell genome that is within or in proximity to the gene encoding NRG3. The transformation is carried out under conditions such that the homologous DNA integrates into the cell genome by recombination. Cells having integrated the homologous DNA are then subjected to conditions which select for amplification of the amplifiable gene, whereby the NRG3 gene is amplified concomitantly. The resulting cells are then screened for production of desired amounts of NRG3. Flanking sequences that are in proximity to a gene encoding NRG3 are readily identified, for example, by the method of genomic walking, using as a starting point the nucleotide sequence, or fragment thereof, of mouse NRG3 of FIG. 1 (SEQ ID NO:1), or human NRG3 of FIG. 2 (SEQ ID NO:5) or FIG. 3 (SEQ ID NO:22). DNA encoding the mouse and human NRG3 polypeptides is deposited with the American Type Culture Collection as ATCC 209156 (mouse; pLXSN.mNRG3), ATCC 209157

(human; pRK5.tk.neo.hNRG3B1), or ATCC 209297 (human; pRK5.tk.neo.hNRG3B2).

The expression "enhancing survival of a cell" refers to the act of increasing the period of existence of a cell, relative to an untreated cell which has not been exposed to NRG3, either in vitro or in vivo.

The phrase "enhancing proliferation of a cell" encompasses the step of increasing the extent of growth and/or reproduction of the cell, relative to an untreated cell, either in vitro or in vivo. An increase in cell proliferation in cell culture can be detected by counting the number of cells before and after exposure to NRG3 (see the Example below). The extent of proliferation can be quantified via microscopic examination of the degree of confluency. Cell proliferation can also be quantified by measuring $^3$H uptake by the cells.

By "enhancing differentiation of a cell" is meant the act of increasing the extent of the acquisition or possession of one or more characteristics or functions which differ from that of the original cell (i.e. cell specialization). This can be detected by screening for a change in the phenotype of the cell (e.g. identifying morphological changes in the cell).

"Muscle cells" include skeletal, cardiac or smooth muscle tissue cells. This term encompasses those cells which differentiate to form more specialized muscle cells (e.g. myoblasts).

"Isolated NRG3 nucleic acid" is RNA or DNA free from at least one contaminating source nucleic acid with which it is normally associated in the natural source and preferably substantially free of any other mammalian RNA or DNA. The phrase "free from at least one contaminating source nucleic acid with which it is normally associated" includes the case where the nucleic acid is present in the source or natural cell but is in a different chromosomal location or is otherwise flanked by nucleic acid sequences not normally found in the source cell. An example of isolated NRG3 nucleic acid is RNA or DNA that encodes a biologically active NRG3 sharing at least 75%, more preferably at least 80%, still more preferably at least 85%, even more preferably 90%, and most preferably 95% sequence identity with the mouse NRG3 shown in FIG. 1 (SEQ ID NO:1), or human NRG3 shown in FIG. 2 (SEQ ID NO:4) or FIG. 3 (SEQ ID NO:22).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/ 0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5×SSC (0.75 M NaCl, 0.075 M sodium citrate), 50 mM sodium phosphate (pH 6/8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS. Yet another example is hybridization using a buffer of 10% dextran sulfate, 2×SSC (sodium chloride/sodium citrate) and 50% formamide at 55° C., followed by a high-stringency wash consisting of 0.1×SSC containing EDTA at 55° C.

"Immunoadhesins" or "NRG3—immunoglobulin chimeras" are chimeric antibody-like molecules that combine the functional domain(s) of a binding protein (usually a receptor, a cell-adhesion molecule or a ligand) with the an immunoglobulin sequence. The most common example of this type of fusion protein combines the hinge and Fc regions of an immunoglobulin (Ig) with domains of a cell-surface receptor that recognizes a specific ligand. This type of molecule is called an "immunoadhesin", because it combines "immune" and "adhesion" functions; other frequently used names are "Ig-chimera", "Ig-" or "Fc-fusion protein", or "receptor-globulin."

"Treatment" refers to both therapeutic treatment and prophylactic or preventative measures. those in need of treatment include those already with the disorder as well as those prone to have the disorder of those in which the disorder is to be prevented.

"Mammal" for purposes of treatment refers to any animal classified as a mammal, including humans, domestic and farm animals, and zoo, sports, or pet animals, such as sheep, dogs, horses, cats, cows, and the like. Preferably, the mammal herein is a human.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; saltforming counterions such as sodium; and/or nonionic surfactants such as Tween™, polyethylene glycol (PEG), and Pluronics™.

General Procedures for the Production of an NRG3 by Recombinant DNA Technology

A. Identification and Isolation of Nucleic Acid Encoding Novel Neuregulin Related Ligand, NRG3.

The native NRG3s of the present invention may be isolated from cDNA or genomic libraries. For example, a suitable cDNA library can be constructed by obtaining polyadenylated mRNA from cells known to express the desired NRG3, and using the mRNA as a template to synthesize double stranded cDNA. Suitable sources of the mRNA are embryonic and adult mammalian tissues. mRNA encoding native NRG3s of the present invention is expressed, for example, in adult mammalian, brain, nervous system, heart, muscle, and testis. The gene encoding the novel NRG3s of the present invention can also be obtained from a genomic library, such as a human genomic cosmid library, or a mouse-derived embryonic stem cell (ES) genomic library.

Libraries, either cDNA or genomic, are screened with probes designed to identify the gene of interest or the protein encoded by it. For cDNA expression libraries, suitable probes include monoclonal and polyclonal antibodies that recognize and specifically bind to a NRG3 of the invention. For cDNA libraries, suitable probes include carefully selected oligonucleotide probes (usually of about 20–80 bases in length) that encode known or suspected portions of a NRG3 polypeptide from the same or different species, and/or complementary or homologous cDNAs or fragments thereof that encode the same or a similar gene. Appropriate probes for screening genomic DNA libraries include, without limitation, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al., *Molecular Cloning: A Laboratory Manual*, New York, Cold Spring Harbor Laboratory Press, 1989, herein incorporated by reference in its entirety.

If DNA encoding a NRG3 of the present invention is isolated by using carefully selected oligonucleotide sequences to screen cDNA libraries from various tissues, the oligonucleotide sequences selected as probes should be sufficient in length and sufficiently unambiguous that false positive selections are minimized. The actual nucleotide sequence(s) is/are usually designed based on regions that have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\gamma^{32}P$) and polynucleotide kinase to radiolabel the 5' end of the oligonucleotide. However, other methods may be used to label the oligonucleotide, including, but not limited to, biotinylation or enzyme labeling.

cDNAs encoding the novel NRG3s can also be identified and isolated by other known techniques of recombinant DNA technology, such as by direct expression cloning, or by using the polymerase chain reaction (PCR) as described in U.S. Pat. No. 4,683,195, issued 28 Jul. 1987, in section 14 of Sambrook et al., supra, or in Chapter 15 of Current Protocols in Molecular Biology, Ausubel et al. eds., Greene Publishing Associates and Wiley-Interscience 1991, which references are herein incorporated by reference in their entirety.

Once cDNA encoding a new native ErbB4 receptor-specific NRG3 from one species has been isolated, cDNAs from other species can also be obtained by cross-species hybridization. According to this approach, human or other mammalian cDNA or genomic libraries are probed by labeled oligonucleotide sequences selected from known NRG3 sequences (such as murine or human sequences) in accord with known criteria. Preferably, the probe sequence should be sufficient in length and sufficiently unambiguous that false positives are minimized. Typically, a $^{32}P$-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid. Hybridization is preferably performed under "stringent conditions", as defined herein.

Once the sequence is known, the gene encoding a particular NRG3 can also be obtained by chemical synthesis, following one of the methods described in Engels and Uhlmann, Agnew (1989) Chem. Int. Ed. Engl. 28:716, herein incorporated by reference in its entirety. These methods include triester, phosphite, phosphoramidite and H-phosphonate methods, PCR and other autoprimer methods, and oligonucleotide syntheses on solid supports.

B. Cloning and Expression of Nucleic Acid Encoding the Novel NRG3s.

Once the nucleic acid encoding a novel NRG3 is available, it is generally ligated into a replicable expression vector for further cloning (amplification of the DNA), or for expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence. Construction of suitable vectors containing one or more of the above listed components, the desired coding and control sequences, employs standard ligation techniques. Isolated plasmids or DNA fragments are cleaved, tailored, and religated in the form desired to generate the plasmids required. For analysis to confirm correct sequences in plasmids constructed, the ligation mixtures are commonly used to transform *E. coli* cells, e.g. *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al. (1981) Nucleic Acids Res. 9:309 or by the method of Maxam et al. (1980) Methods in Enzymology 65:499.

The polypeptides of the present invention may be expressed in a variety of prokaryotic and eukaryotic host cells. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), *Pseudomonas* species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* (Beach and Nurse (1981) Nature 290:140), *Kluyveromyces lactis* (Louvencourt et al. (1983) J. Bacteriol. 737); *yarrowia* (EP 402,226); *Pichia pastoris* (EP 183,070), *Trichoderma reesia* (EP 244,234), *Neurospora crassa* (Case et al. (1979) Proc. Natl. Acad. Sci. USA 76:5259–5263); and *Aspergillus* hosts such as *A. nidulans* (Ballance et al. (1983) Biochem. Biophys. Res. Commun. 112:284–289; Tilburn et al. (1983) Gene 26:205–221; Yelton et al. (1984) Proc. Natl. Acad. Sci. USA 81:1470–1474) and *A. niger* (Kelly and Hynes (1985) EMBO J. 4:475–479).

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila* melangaster (fruitfly), and *Bombyx mori* host cells have been identified. See, e.g. Luckow et al. (1988) Bio/Technology 6:47–55; Miller et al., in Genetic Engineering, Setlow, J. K. et al., eds., Vol. 8 (Plenum Publishing, 1986), pp. 277–279; and Maeda et al. (1985) Nature 315: 592–594. A variety of such viral strains are publicly available, e.g. the L-1 variant of *Autographa californica* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the NRG3 DNA. During incubation of the plant cell culture with *A. tumefaciens*, the DNA encoding a NRG3 is transferred to the plant cell host such that it is transfected, and will, under appropriate conditions, express the NRG3 DNA. In addition, regulatory and signal sequences compatible with plant cells are available, such as the nopaline synthase promoter and polyadenylation signal sequences. Depicker et al. (1982) J. Mol. Appl. Gen. 1:561. In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989.

However, interest has been greatest in vertebrate cells, and propagation of vertebrate cells in culture (tissue culture) is per se well known (see for example, Tissue Culture, Academic Press, Kruse and Patterson, editors (1973)). Examples of useful mammalian host cell lines are monkey kidney CV1 line transformed by SV40 (COS-7, ATCC CRL 1651); human embryonic kidney cell line (293 or 293 cells subcloned for growth in suspension culture, Graham et al. (1977) J. Gen. Virol. 36:59); baby hamster kidney cells (BHK, ATCC CCL 10); Chinese hamster ovary cells/-DHFR (CHO, Urlaub and Chasin (1980) Proc. Natl. Acad. Sci. USA 77:4216); mouse sertolli cells (TM4, Mather (1980) Biol. Reprod. 23:243–251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells (Mather et al. (1982) Annals N.Y. Acad. Sci. 383:44068); MRC 5 cells; FS4 cells; and a human hepatoma cell line (Hep G2). Preferred host cells are human embryonic kidney 293 and Chinese hamster ovary cells.

Particularly useful in the practice of this invention are expression vectors that provide for the expression in mammalian cells of DNA encoding a novel NRG3 herein. Where transient expression is preferred, expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of a native NRG3 of the invention.

Other methods, vectors, and host cells suitable for adaptation to the synthesis of the NRG3s in recombinant vertebrate cell culture are described for example, in Getting et al. (1981) Nature 293:620–625; Mantel et al. (1979) Nature 281:40–46; Levinson et al.; EP 117,060 and EP 117,058. Particularly useful plasmids for mammalian cell culture expression of the NRG3 polypeptides are pRK5 (EP 307, 247), or pSVI6B (PCT Publication No. WO 91/08291).

Other cloning and expression vectors suitable for the expression of the NRG3s of the present invention in a variety of host cells are, for example, described in EP 457,758 published 27 Nov. 1991. A large variety of expression vectors is now commercially available. An exemplary commercial yeast expression vector is pPIC.9 (Invitrogen), while an commercially available expression vector suitable for transformation of *E. coli* cells is PET15b (Novagen).

C. Culturing the Host Cells.

Prokaryote cells used to produced the NRG3s of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace (1979) Meth. Enzymol. 58:44; Barnes and Sato (1980) Anal. Biochem. 102:255, U.S. Pat. Nos. 4,767,704; 4,657,866; 4,927,762; or 4,560,655; WO 90/03430; WO 87/00195 or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the NRG3s of this invention may be produced by homologous recombination, or with recombinant production methods utilizing control elements introduced into cells already containing DNA encoding the particular NRG3.

D. Detecting Gene Amplification and/or Expression.

Gene amplification and/or expression may be measured in a sample directly, for example, by conventional Southern blotting, Northern blotting to quantitate the transcription of mRNA (Thomas (1980) Proc. Natl. Acad. Sci. USA 77:5201–5205), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. A particularly sensitive staining technique suitable for use in the present invention is described by Hse et al. (1980) Am. J. Clin. Pharm. 75:734–738.

Antibodies useful for immunohistochemical staining and/or assay of sample fluids may be either monoclonal or polyclonal, and may be prepared in any animal. Conveniently, the antibodies may be prepared against a native NRG3 polypeptide, or against a synthetic peptide based on the DNA sequence disclosed herein.

E. Amino Acid Sequence Variants of a Native NRG3.

Amino acid sequence variants of native NRG3s are prepared by methods known in the art by introducing appropriate nucleotide changes into a native NRG3 DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the native NRG3, the amino acid sequence variants of NRG3s are preferably constructed by mutating the DNA, either to arrive at an allele or an amino acid sequence variant that does not occur in nature.

One group of mutations will be created within the extracellular domain or within the EGF-like domain of a novel native mouse or human NRG3 of the present invention (see FIG. 3 for the delineation of the extracellular domain (SEQ ID NO:3 or SEQ ID NO:7) and EGF-like domain (SEQ ID NO:4) within human or mouse NRG3 amino acid sequences, respectively. Since these domains are believed to be functionally important, alterations such as non-conservative substitutions, insertions and/or deletions in these regions are expected to result in genuine changes in the properties of the native receptor molecules such as in ErbB4 receptor binding and activation. Accordingly, amino acid alterations in this region are also believed to result in variants with properties significantly different from the corresponding native polypeptides. Non-conservative substitutions within these functionally important domains may result in variants which lose the ErbB4 receptor recognition and binding ability of their native counterparts, or have increased ErbB4 receptor recognition properties, enhanced selectivity, or enhanced activation properties as compared to the corresponding native proteins.

Alternatively or in addition, amino acid alterations can be made at sites that differ in novel NRG3s from various species, or in highly conserved regions, depending on the goal to be achieved. Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3. One helpful technique for such modifications is called "alanine scanning" (Cunningham and Wells (1989) Science 244:1081–1085).

In yet another group of the variant NRG3s of the present invention, one or more of the functionally less significant domains may be deleted or inactivated. For example, the deletion or inactivation of the transmembrane domain yields soluble variants of the native proteins. Alternatively, or in addition, the cytoplasmic domain may be deleted, truncated or otherwise altered.

Naturally-occurring amino acids are divided into groups based on common side chain properties:
(1) hydrophobic: norleucine, met, ala, val, leu, ile;
(2) neutral hydrophobic: cys, ser, thr;
(3) acidic: asp, glu;
(4) basic: asn, gin, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another. Substantial changes in function or immunological identity are made by NRG3 substitutions that are less conservative, i.e. differ more significantly in their effect on maintaining (a) the structure of the polypeptide backbone in the area of substitution, for example as a sheet or helical conformation, (b) the charge or hydrophobicity of the molecule at the target site or (c) the bulk of the side chain. The substitutions which in general are expected to produce the greatest changes in the properties of the novel native NRG3s of the present invention will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g. glycine. Such substitutions are expected to have their most significant effect when made within the extracellular domain, such as in the EGF-like domain.

Substitutional variants of the novel NRG3s of the present invention also include variants where functionally homologous (having at least about 40%–50% homology) domains of other proteins are substituted by routine methods for one or more of the above-identified domains within the novel NRG3 structure, such as the extracellular domain or EGF-like domain.

Amino acid sequence deletions generally range from about 1 to 30 residues, more preferably about 1 to 10 residues, and typically are contiguous. Typically, the transmembrane and cytoplasmic domains, or only the transmembrane domains are deleted. However, deletion from the C-terminus to any suitable amino acid N-terminal to the transmembrane region which preserves the biological activity or immunological cross-reactivity of a native NRG3 is suitable. The transmembrane region (TM) of each of the human and mouse NRG3 consensus sequences is shown in FIGS. 4A and 4B to range from about amino acid 362 to about amino acid 384 (human SEQ ID NO:6 and SEQ ID NO:23), and about amino acid 360 to about amino acid 382 (mouse SEQ ID NO:2).

A preferred class of substitutional and/or deletional variants of the present invention are those involving a transmembrane region of a novel NRG3 molecule. Transmembrane regions are highly hydrophobic or lipophilic domains that are the proper size to span the lipid bilayer of the cellular membrane. They are believed to anchor the NRG3 in the cell membrane, and allow for homo- or heteropolymeric complex formation. Inactivation of the transmembrane domain, typically by deletion or substitution of transmembrane domain hydroxylation residues, will facilitate recovery and formulation by reducing its cellular or membrane lipid affinity and improving its aqueous solubility. If the transmembrane and cytoplasmic domains are deleted one avoids the introduction of potentially immunogenic epitopes, whether by exposure of otherwise intracellular polypeptides that might be recognized by the body as foreign or by insertion of heterologous polypeptides that are potentially immunogenic. Inactivation of the membrane insertion function is accomplished by deletion of sufficient residues to produce a substantially hydrophilic hydropathy profile in the transmembrane or by substituting with heterologous residues which accomplish the same result.

A principle advantage of the transmembrane inactivated variants of the NRG3s of the present invention is that they may be secreted into the culture medium of recombinant hosts. These variants are soluble in body fluids such as blood and do not have an appreciable affinity for cell membrane lipids, thus considerably simplifying their recovery from recombinant cell culture. As a general proposition, such soluble variants will retain a functional extracellular domain or fragment thereof, will not have a functional transmembrane domain, and preferably will not have a functional cytoplasmic domain.

For example, the transmembrane domain may be substituted by any amino acid sequence, e.g. a random or predetermined sequences of about 5 to 50 serine, threonine, lysine, arginine, glutamine, aspartic acid and like hydrophilic residues, which altogether exhibit a hydrophilic hydropathy profile. Like the deletional (truncated) soluble variants, these variants are secreted into the culture medium of recombinant hosts.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the novel NRG3 amino acid sequence) may range generally from about 1 to 10 residues, more preferably 1 to 5 residues, more preferably 1 to 3 residues. An example of a terminal insertion includes fusion of a heterologous N-terminal signal sequence to the N-terminus of the NRG3 molecule to facilitate the secretion of the mature NRG3 or a fragment thereof from recombinant host cells. Such signal sequences will generally be obtained from, and thus be homologous to, a signal sequence of the intended host cell species. Suitable sequences include STII or Ipp for *E. coli*, alpha factor for yeast, and viral signals such as herpes gD for mammalian cells.

Other insertional variants of the native NRG3 molecules include the fusion of the N- or C-terminus of the NRG3 molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on 6 Apr. 1989.

Further insertional variants are immunologically active derivatives of the novel NRG3s, which comprise the EGF-like domain and a polypeptide containing an epitope of an immunologically competent extraneous polypeptide, i.e. a polypeptide which is capable of eliciting an immune response in the animal to which the fusion is to be administered or which is capable of being bound by an antibody raised against an extraneous polypeptide. Typical examples of such immunologically competent polypeptides are allergens, autoimmune epitopes, or other potent immunogens or antigens recognized by pre-existing antibodies in the fusion recipient, including bacterial polypeptides such as trpLE, β-glactosidase, viral polypeptides such as herpes gD protein, and the like.

Immunogenic fusions are produced by cross-linking in vitro or by culture of cells transformed with recombinant DNA encoding an immunogenic polypeptide. It is preferable that the immunogenic fusion be one in which the immunogenic sequence is joined to or inserted into a novel NRG3 molecule or fragment thereof by one or more peptide bonds. These products therefore consist of a linear polypeptide chain containing the NRG3 epitope and at least one epitope foreign to the NRG3. It will be understood that it is within the scope of this invention to introduce the epitopes anywhere within a NRG3 molecule of the present invention or a fragment thereof. These immunogenic insertions are particularly useful when formulated into a pharmacologically acceptable carrier and administered to a subject in order to raise antibodies against the NRG3 molecule, which antibodies in turn are useful as diagnostics, in tissue-typing, or in purification of the novel NRG3s by standard immunoaffinity techniques. Alternatively, in the purification of the NRG3s of the present invention, binding partners for the fused extraneous polypeptide, e.g. antibodies, receptors or ligands, are used to adsorb the fusion from impure admixtures, after which the fusion is eluted and, if desired, the novel NRG3 is recovered from the fusion, e.g. by enzymatic cleavage.

Since it is often difficult to predict in advance the characteristics of a variant NRG3, it will be appreciated that some screening will be needed to select the optimum variant. Such screening includes, but is not limited to, arrays of ErbB4 receptor binding.

After identifying the desired mutation(s), the gene encoding a NRG3 variant can, for example, be obtained by chemical synthesis as described herein. More preferably, DNA encoding a NRG3 amino acid sequence variant is prepared by site-directed mutagenesis of DNA that encodes an earlier prepared variant or a nonvariant version of the NRG3. Site-directed (site-specific) mutagenesis allows the production of NRG3 variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al. (1983) DNA 2:183. As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M. (1982) Nucleic Acids Res. 10:6487–6500). Also, plasmid vectors that contain a single-stranded phage origin of replication (Veira et al. (1987) Meth. Enzymol. 153:3) may be employed to obtain single-stranded DNA. Alternatively, nucleotide substitutions are introduced by synthesizing the appropriate DNA fragment in vitro, and amplifying it by PCR procedures known in the art.

The PCR amplification technique may also be used to create amino acid sequence variants of a novel NRG3. In a specific example of PCR mutagenesis, template plasmid DNA (1 µg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp$^R$ kits (obtained from Perkin-Elmer Cetus, Norwalk, Conn. and Emeryville, Calif.), and 25 pmole of each oligonucleotide primer, to a final volume of 50 µl. The reaction mixture is overlayered with 35 µl mineral oil. The reaction is denatured for 5 minutes at 100° C., placed briefly on ice, and then 1 µl Thermus aquaticus (Taq) DNA polymerase (5 units/l), purchased from Perkin-Elmer Cetus, Norwalk, Conn. and Emeryville, Calif.) is added below the mineral oil layer. The reaction mixture is then inserted into a DNA Thermal Cycler (Perkin-Elmer Cetus) programmed as follows: (as an example)

2 min. 55° C.,
30 sec. 72° C., then 19 cycles of the following:
30 sec. 94° C.,
30 sec. 55° C., and
30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Cassette mutagenesis is another method useful for preparing variants and is based on the technique described by Wells et al. (1985) Gene 34:315.

Additionally, the so-called phagemid display method may be useful in making amino acid sequence variants of native or variant NRG3s or their fragments. This method involves 1) constructing a replicable expression vector comprising a first gene encoding a receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; 2) mutating the vector at one or more selected positions within the first gene thereby forming a family of related plasmids; 3) transforming suitable host cells with the plasmids; 4) infecting the transformed host cells with a helper phage having a gene encoding the phage coat protein; 5) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; 6) contacting the phagemid particles with a suitable antigen so that at least a portion of the phagemid particles bind to the antigen; and 7) separating the phagemid particles that bind from those that do not. Steps 4 through 7 can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is E. coli, and protease-deficient strains of E. coli.

Further details of the foregoing and similar mutagenesis techniques are found in general textbooks, such as, for example, Sambrook et al., supra, and Current Protocols in Molecular Biology, Ausubel et al. eds., supra.

F. Glycosylation Variants.

Glycosylation variants are included within the scope of the present invention. They include variants completely lacking in glycosylation (unglycosylated), variants having at least one less glycosylated site than the native form (deglycosylated) as well as variants in which the gycosylation has been changed. Included are deglycosylated and unglycosylated amino acid sequences variants, deglycosylated and unglycosylated native NRG3s or fragments thereof and other glycosylation variants. For example, substitutional or deletional mutagenesis may be employed to eliminate the N- or O-linked glycosylation sites in the a native or variant NRG3 of the present invention, e.g. the asparagine residue may be deleted or substituted for another basic residue such as lysine or histidine. Alternatively, flanking residues making up the glycosylation site may be substituted or deleted, even though the asparagine residues remain unchanged, in order to prevent glycosylation by eliminating the glycosylation recognition site. Where the preferred NRL variant is the EGF-like domain of NRG3, the fragment is preferably unglycosylated.

Additionally, unglycosylated NRG3s which have the glycosylation sites of a native molecule may be produced in recombinant prokaryotic cell culture because prokaryotes are incapable of introducing glycosylation into polypeptides.

Glycosylation variants may be produced by appropriate host cells or by in vitro methods. Yeast and insect cells, for example, introduce glycosylation which varies significantly from that of mammalian systems. Similarly, mammalian cells having a different species (e.g. hamster, murine, porcine, bovine or ovine), or tissue origin (e.g. lung, liver, lymphoid, mesenchymal or epidermal) than the source of the NRG3 are routinely screened for the ability to introduce variant glycosylation as characterized for example by elevated levels of mannose or variant ratios of mannose, fucose, sialic acid, and other sugars typically found in mammalian glycoproteins. In vitro processing of the NRG3 typically is accomplished by enzymatic hydrolysis, e.g. neuraminidate digestion.

G. Covalent Modifications.

Covalent modifications of the novel NRG3s of the present invention are included within the scope of the invention. Such modifications are traditionally introduced by reacting targeted amino acid residues of the NRG3s with an organic derivatizing agent that is capable of reacting with selected amino acid side chains or terminal residues, or by harnessing mechanisms of post- translational modifications that function in selected recombinant host cells. The resultant covalent derivatives are useful in programs directed at identifying residues important for biological activity, for immunoassays of the NRG3, or for the preparation of anti-NRG3 antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Derivatization with bifunctional agents is useful for preparing intramolecular aggregates of the NRG3s with polypeptides as well as for cross-linking the NRG3 polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains (T. E. Creighton (1983) Proteins: Structure and Molecular Properties, W.H. Freeman & Co., San Francisco, pp. 79–86).

Further derivatives of the NRG3s herein are the so called "immunoadhesins", which are chimeric antibody-like molecules combining the functional domain(s) of a binding protein (usually a receptor, a cell-adhesion molecule or a ligand) with the an immunoglobulin sequence. The most common example of this type of fusion protein combines the hinge and Fc regions of an immunoglobulin (Ig) with domains of a cell-surface receptor that recognizes a specific ligand. This type of molecule is called an "immunoadhesin", because it combines "immune" and "adhesion" functions; other frequently used names are "Ig-chimera", "Ig-" or "Fc-fusion protein", or "receptor-globulin."

Immunoadhesins reported in the literature include, for example, fusions of the T cell receptor (Gascoigne et al. (1987) Proc. Natl. Acad. Sci. USA 84:2936–2940); CD4 (Capon et al. (1989) Nature 337:525–531; Traunecker et al. (1989) Nature 339:68–70; Zettmeissl et al. (1990) DNA Cell Biol. USA 9:347–353; Byrn et al. (1990) Nature 344: 667–670); L-seNRG3 (homing receptor) (Watson et al. (1990) J. Cell. Biol. 110:2221–2229); Watson et al. (1991) Nature 349:164–167); E-seNRG3 (Mulligan et al. (1993) J. Immunol. 151:6410–17; Jacob et al.(1995) Biochemistry 34:1210–1217); P-seNRG3 (Mulligan et al., supra; Hollenbaugh et al. (1995) Biochemistry 34:5678–84); ICAM-1 (Stauton et al. (1992) J. Exp. Med. 176:1471–1476; Martin et al. (1993) J. Virol. 67:3561–68; Roep et al. (1994) Lancet 343:1590–93); ICAM-2 (Damle et al. (1992) J. Immunol. 148:665–71); ICAM-3 (Holness et al. (1995) J. Biol. Chem. 270:877–84); LFA-3 (Kanner et al. (1992) J. Immunol. 148:23–29); L1 glycoprotein (Doherty et al. (1995) Neuron 14:57–66); TNF-R1 (Ashkenazi et al., (1991) Proc. Natl. Acad. Sci. USA 88:10535–539); Lesslauer et al. (1991) Eur. J. Immunol. 21:2883–86; Peppel et al. (1991) J. Exp. Med. 174:1483–1489); TNF-R2 (Zack et al. (1993) Proc. Natl. Acad. Sci. USA 90:2335–39; Wooley et al. (1993) J. Immunol. 151:6602–07); CD44 (Aruffo et al. (1990) Cell 61:1303–1313); CD28 and B7 (Linsley et al. (1991) J. Exp. Med. 173:721–730); CTLA-4 (Lisley et al. (1991) J. Exp. Med. 174:561–569); CD22 (Stamenkovic et al. (1991) Cell 66:1133–1144); NP receptors (Bennett et al. (1991) J. Biol. Chem. 266:23060–23067); IgE receptor α (Ridgway and Gorman (1991) J. Cell. Biol. 115:1448 abstr.); IFN-γR α- and β-chain (Marsters et al. (1995) Proc. Natl. Acad. Sci. USA 92:5401–05); trk-A, -B, and -C (Shelton et al. (1995) J. Neurosci. 15:477–91); IL-2 (Landolfi (1991) J. Immunol. 146:915–19); IL-10 (Zheng et al. (1995) J. Immunol. 154: 5590–5600).

The simplest and most straightforward immunoadhesin design combines the binding region(s) of the 'adhesin' protein with the hinge and Fc regions of an immunoglobulin heavy chain. Ordinarily, when preparing the NRG3-immunoglobulin chimeras of the present invention, nucleic acid encoding the desired NRG3 polypeptide will be fused at the C-terminus of the desired sequence to the N-terminus of a nucleic acid sequence encoding an immunoglobulin constant domain sequence, however fusion to the N-terminus of the desired NRG3 sequence is also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the NRG3-immunoglobulin chimeras.

In a preferred embodiment, the sequence of a native, mature NRG3 polypeptide, or a soluble form thereof such as a (transmembrane domain-inactivated or EGF-like domain polypeptide) form thereof, is fused to the N-terminus of the C-terminal portion of an antibody (in particular the Fc domain), containing the effector functions of an immunoglobulin, e.g. IgG-1. It is possible to fuse the entire heavy chain constant region to the NRG3 sequence. However, more preferably, a sequence beginning in the hinge region just upstream of the papain cleavage site (which defines IgG Fc chemically; residue 216, taking the first residue of heavy chain constant region to be 114 (Kobet et al., supra), or analogous sites of other immunoglobulins) is used in the fusion. In a particularly preferred embodiment, the NRG3 sequence (full length or soluble) is fused to the hinge region and CH2 and CH3 or CH1, hinge, CH2 and CH3 domains of an IgG-1, IgG-2, or IgG-3 heavy chain. The precise site at which the fusion is made is not critical, and the optimal site can be determined by routine experimentation.

In some embodiments, the NRG3-immunoglobulin chimeras are assembled as multimers, and particularly as homodimers or -tetramers (WO 91/08298). Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled NRG3-immunoglobulin chimeras within the scope of the invention are schematically diagrammed below:

(a) $AC_L$-$AC_L$;
(b) $AC_H$-[$AC_H$, $AC_L$-$AC_H$, $AC_L$-$V_H C_H$, or $V_L C_L$-$AC_H$];
(c) $AC_L$-$AC_H$-[$AC_L$-$AC_H$, $AC_L$-$V_H C_H$, $V_L C_L$-$AC_H$, or $V_L C_L$-$V_H C_H$];
(d) $AC_L$-$V_H C_H$-[$A_C H$, or $AC_L$-$V_H C_H$, or $V_L C_L$-$AC_H$];
(e) $V_L C_L$-$AC_H$-[$AC_L$-$V_H C_H$, or $V_L C_L$-$AC_H$]; and
(f) $[A\text{-}Y]_n$-$[V_L C_L$-$V_H C_H]_2$, wherein
  each A represents identical or different novel NRG3 polypeptide amino acid sequences;
  $V_L$ is an immunoglobulin light chain variable domain;
  $V_H$ is an immunoglobulin heavy chain variable domain;
  $C_L$ is an immunoglobulin light chain constant domain;
  $C_H$ is an immunoglobulin heavy chain constant domain;
  n is an integer greater than 1;
  Y designates the residue of a covalent cross-linking agent.

In the interest of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Although the presence of an immunoglobulin light chain is not required in the immunoadhesins of the present invention, an immunoglobulin light chain might be present either covalently associated to an NRG3-immunoglobulin heavy chain fusion polypeptide, or directly fused to the NRG3 polypeptide. In the former case, DNA encoding an immunoglobulin light chain is typically coexpressed with the DNA encoding the NRG3-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human IgG-1 and IgG-3 immunoglobulin sequences is preferred. A major advantage of using IgG-1 is that IgG-1 immunoadhesins can be purified efficiently on immobilized protein A. In contrast, purification of IgG-3 requires protein G, a significantly less versatile medium. However, other structural and functional properties of immunoglobulins should be considered when choosing the Ig fusion partner for a particular immunoadhesin construction. For example, the IgG-3 hinge is longer and more flexible, so it can accommodate larger 'adhesin' domains that may not fold or function properly when fused to IgG-1. While IgG immunoadhesins are typically mono- or bivalent, other Ig subtypes like IgA and IgM may give rise to dimeric or pentameric structures, respectively, of the basic Ig homodimer unit. Multimeric immunoadhesins are advantageous in that they can bind their respective targets with greater avidity than their IgG-based counterparts. Reported examples of such structures are CD4-IgM (Traunecker et al., supra); ICAM-IgM (Martin et al. (1993) J. Virol. 67:3561–68); and CD2-IgM (Arulanandam et al. (1993) J. Exp. Med. 177:1439–50).

For NRG3-Ig immunoadhesins, which are designed for in vivo application, the pharmacokinetic properties and the effector functions specified by the Fc region are important as well. Although IgG-1, IgG-2 and IgG-4 all have in vivo half-lives of 21 days, their relative potencies at activating the complement system are different. IgG-4 does not activate complement, and IgG-2 is significantly weaker at complement activation than IgG-1. Moreover, unlike IgG-1, IgG-2 does not bind to Fc receptors on mononuclear cells or neutrophils. While IgG-3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG-1 has only four serologically-defined allotypic sites, two of which (G1m and 2) are located in the Fc region; and one of these sites G1m1, is non-immunogenic. In contrast, there are 12 serologically-defined allotypes in IgG-3, all of which are in the Fc region; only three of these sites (G3 m5, 11 and 21) have one allotype which is nonimmunogenic. Thus, the potential immunogenicity of a γ3 immunoadhesin is greater than that of a γ1 immunoadhesin.

NRG3-Ig immunoadhesins are most conveniently constructed by fusing the cDNA sequence encoding the NRG3 portion in-frame to an Ig cDNA sequence. However, fusion to genomic Ig fragments can also be used (see, e.g. Gascoigne et al. (1987) Proc. Natl. Acad. Sci. USA 84:2936–2940; Aruffo et al. (1990) Cell 61:1303–1313; Stamenkovic et al. (1991) Cell 66:1133–1144). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques.

Other derivatives of the novel NRG3s of the present invention, which possess a longer half-life than the native molecules comprise the NRG3, NRG3 fragment (such as the EGF-like domain) or a NRG3-immunoglobulin chimera, covalently bonded to a nonproteinaceous polymer. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyelkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce cross-linking, or to purify the reaction products through gel filtration or chromatographic sieves to recover substantially homogenous derivatives.

The molecular weight of the polymer may desirably range from about 100 to 500,000, and preferably is from about 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the novel NRG3, NRG3 fragment or to the NRG3-immunoglobulin chimeras through a multifunctional crosslinking agent which reacts with the polymer and one or more amino acid or sugar residues of the NRG3 or NRG3-immunoglobulin chimera to be linked. However, it is within the scope of the invention to directly crosslink the polymer by reacting a derivatized polymer with the hybrid, or vice versa.

The covalent crosslinking site on the NRG3 or NRG3-Ig includes the N-terminal amino group and epsilon amino groups found on lysine residues, as well as other amino, imino, carboxyl, sulfhydryl, hydroxyl or other hydrophilic groups. The polymer may be covalently bonded directly to the hybrid without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylcloroformate or P-nitrophenylcloroformate activated PEG.) Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase, (either of which produces the aldehyde derivative of the carbohydrate), followed by reaction with hydrazide or amino derivatized polymers, in the same fashion as is described by Heitzmann et al. (1974) P.N.A.S. 71:3537–41 or Bayer et al. (1979) Methods in Enzymology 62:310, for the labeling of oligosaccharides with biotin or avidin. Further, other chemical or enzymatic methods which have been used heretofore to link oligosaccharides are particularly advantageous because, in general, there are fewer substitutions than amino acid sites for derivatization, and the oligosaccharide products thus will be more homogenous. The oligosaccharide substituents also are optionally modified by enzyme digestion to remove sugars, e.g. by neuraminidase digestion, prior to polymer derivatization.

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction. "Water soluble" in reference to the polymer conjugate means that the conjugate is soluble in physiological fluids such as blood.

The degree of substitution with such a polymer will vary depending upon the number of reactive sites on the protein, whether all or a fragment of the protein is used, whether the protein is a fusion with a heterologous protein (e.g. a NRG3-immunoglobulin chimera), the molecular weight, hydrophilicity and other characteristics of the polymer, and the particular protein derivatization sites chosen. In general, the conjugate contains about from 1 to 10 polymer molecules, while any heterologous sequence may be substituted with an essentially unlimited number of polymer molecules so long as the desired activity is not significantly adversely affected. The optimal degree of cross-linking is easily determined by an experimental matrix in which the time, temperature and other reaction conditions are varied to change the degree of substitution, after which the ability of the conjugates to function in the desired fashion is determined.

The polymer, e.g. PEG, is cross-linked by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al. (1983) Anal Biochem. 131:25–33) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems in purification, as both gel filtration chromatography and hydrophilic interaction chromatography are adversely affected. In addition, the high concentrations of "activated PEG" may precipitate protein, a problem that per se has been noted previously (Davis, U.S. Pat. No. 4,179, 337). On the other hand, aldehyde chemistry (Royer, U.S. Pat. No. 4,002,531) is more efficient since it requires only a 40-fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al. (1984) J. Polym. Sci. Polym. Chem. Ed. 22:341–52). The use of a Moffatt oxidation, utilizing DMSO and acetic anhydride, obviates this problem. In addition, the sodium borohydride suggested by Royer must be used at high pH and has a significant tendency to reduce disulfide bonds. In contrast, sodium cyanoborohydride, which is effective at neutral pH and has very little tendency to reduce disulfide bonds is preferred.

The long half-life conjugates of this invention are separated from the unreacted starting materials by gel filtration. Heterologous species of the conjugates are purified from one another in the same fashion. The polymer also may be water-insoluble, as a hydrophilic gel.

The novel NRG3s may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in Remington's Pharmaceutical Sciences, 16th Edition, Osol, A., Ed. (1980).

H. Antibody Preparation.

(i) Polyclonal Antibodies

Polyclonal antibodies to a NRG3, or fragment thereof (such as the EGF-like domain) of the present invention generally are raised in animals by multiple subcutaneous (sc) or intraperitoneal (ip) injections of the NRG3 and an adjuvant. It may be useful to conjugate the NRG3 or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the immunogenic conjugates or derivatives by combining 1 mg or 1 μg of conjugate (for rabbits or mice, respectively) with 3 volumes of Freud's complete adjuvant and injecting the solution intradermally at multiple sites. One month later the animals are boosted with ⅕ to ⅒ the original amount of conjugate in Freud's complete adjuvant by subcutaneous injection at multiple sites. 7 to 14 days later the animals are bled and the serum is assayed for anti-NRG3 antibody titer. Animals are boosted until the titer plateaus. Preferably, the animal boosted with the conjugate of the same NRG3, but conjugated to a different protein and/or through a different cross-linking reagent. Conjugates also can be made in recombinant cell culture as protein fusions. Also, aggregating agents such as alum are used to enhance the immune response.

(ii) Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, the anti-NRG3 monoclonal antibodies of the invention may be made using the hybridoma method first described by Kohler and Milstein (1975) Nature 256:495, or may be made by recombinant DNA methods (Cabilly, et al., U.S. Pat. No. 4,816,567).

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al. (1984) Proc. Nat. Acad. Sci. 81:6851, or by covalently joining to the immunoglobulin coding sequence all or part of the coding sequence for a non-immunoglobulin polypeptide. In that manner, "chimeric" or "hybrid" antibodies are prepared that have the binding specificity of a NRG3 monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a NRG3 and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al. (1962) Nature 144:945; David, et al. (1974) Biochemistry 13:1014; Pain, et al. (1981) J. Immunol. Meth. 40:219; and Nygren (1982) J. Histochem. and Cytochem. 30:407.

The antibodies of the present invention may be employed in any known assay method, such as competitive binding assays, direct and indirect sandwich assays, and immunoprecipitation assays. Zola, Monoclonal Antibodies: A Manual of Techniques, pp. 147–158 (CRC Press, Inc., 1987).

(iii) Humanized Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321: 522–525; Riechmann et al. (1988) Nature 332:323–327; Verhoeyen et al. (1988) Science 239:1534–1536), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see PCT/US93/07832, which is a continuation-in-part of PCT/US92/05126, which references are herein incorporated by reference in their entirety.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al. (1993) Proc. Natl. Acad. Sci. USA 90:2551–255; Jakobovits et al. (1993) Nature 362:255–258.

(iv) Bispecific Antibodies

Bispecific antibodies are monoclonal, preferably human or humanized, antibodies that have binding specificities for at least two different antigens. In the present case, one of the binding specificities is for a NRG3 of the present invention the other one is for any other antigen, for example, another member of the NRG3 family. Such constructs can also be referred to as bispecific immunoadhesins.

Traditionally, the recombinant production of bispecific antibodies is based on the coexpression of two immunoglobulin heavy chain-light chain pairs, where the two heavy chains have different specificities (Millstein and Cuello (1983) Nature 305:537–539). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al. (1991) EMBO 10:3655–3659. This problem may be overcome by selecting a common light chain for each arm o the bispecific antibody such that binding specificity of each antibody is maintained, as disclosed in U.S. application Ser. No. 08/850,058, filed May 5, 1997.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT application WO 94/04690 published 3 Mar. 1994.

For further details of generating bispecific antibodies see, for example, Suresh et al. (1986) Methods in Enzymology 121:210.

(v) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

I. Diagnostic Kits and Articles of Manufacture.

Since the invention provides a diagnostic assay (i.e. for detecting neurological disorders and for detecting the presence of NRG3 in a sample using antibodies or DNA markers) as a matter of convenience, the reagents for these assays can be provided in a kit, i.e., a packaged combination of reagents, for combination with the sample to be tested. The components of the kit will normally be provided in predetermined ratios. Thus, a kit may comprise the antibody or NRG3 (DNA or polypeptide or fragment thereof) labeled directly or indirectly with a suitable label. Where the detectable label is an enzyme, the kit will include substrates and cofactors required by the enzyme (e.g. a substrate precursor which provides the detectable chromophore or fluorophore). In addition, other additives may be included such as stabilizers, buffers and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the bioassay.

In another embodiment of the invention, an article of manufacture containing materials useful for the treatment of the neurological disorders described herein is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is NRG3 or an agonist or antagonist thereof. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

J. Peptide and Non-Peptide Analogs.

Peptide analogs of the NRG3s of the present invention are modeled based upon the three-dimensional structure of the native polypeptides. Peptides may be synthesized by well known techniques such as the solid-phase synthetic techniques initially described in Merrifield (1963) J. Am. Chem. Soc. 15:2149–2154. Other peptide synthesis techniques are, for examples, described in Bodanszky et al., Peptide Synthesis, John Wiley & Sons, 2nd Ed., 1976, as well as in other reference books readily available for those skilled in the art. A summary of peptide synthesis techniques may be found in Stuart and Young, Solid Phase Peptide Synthelia, Pierce Chemical Company, Rockford, Ill. (1984). Peptides may also be prepared by recombinant DNA technology, using a DNA sequence encoding the desired peptide.

In addition to peptide analogs, the present invention also contemplates non-peptide (e.g. organic) compounds which display substantially the same surface as the peptide analogs of the present invention, and therefore interact with other molecules in a similar fashion.

K. Uses of the NRG3s.

Amino acid sequence variants of the native NRG3s of the present invention may be employed therapeutically to compete with the normal binding of the native proteins to their receptor, ErbB4. The NRG3 amino acid sequence variants are, therefore, useful as competitive inhibitors of the biological activity of native NRG3s.

Native NRG3s and their amino acid sequence variants are useful in the identification and purification of the native ErbB4 receptor. The purification is preferably performed by immunoadhesins comprising a NRG3 amino acid sequence retaining the qualitative ability of a native NRG3 of the present invention to recognize its native ErbB4 receptor.

The native NRG3s of the present invention are further useful as molecular markers of the tissues in which the ErbB4 receptor is expressed.

Furthermore, the NRG3s, preferably the EGF-like domain of the NRG3 of the present invention, provide valuable sequence motifs which can be inserted or substituted into other native members of the NRG3 family of molecules, such as the heregulins. The alteration of these native proteins by the substitution or insertion of sequences from the novel NRG3s of the present invention can yield variant molecules with altered biological properties, such as receptor binding affinity or receptor specificity. For example, one or more NRG3 domains of another member of the NRG3 family may be entirely or partially replaced by NRG3 domain sequences derived from the NRG3s of the present invention. Similarly, EGF-like domain sequences from the NRG3s herein may be substituted or inserted into the amino acid sequences of other NRG3s.

Nucleic acid encoding the NRG3s of the present invention is also useful in providing hybridization probes for searching cDNA and genomic libraries for the coding sequence of other NRG3s.

Additionally, NRG3s of the invention are useful in kits for the diagnosis of disease related to NRG3 and for methods of detecting the presence or absence of NRG3 in a sample, such as a body fluid, as described herein.

Binding and activation of the ErbB4 receptor by NRG3 is expected to mediate such physiological responses in cells expressing the ErbB4 receptor as cell growth, cell proliferation, and cell differentiation particularly in neural tissue. As a result, mammalian NRG3, or an ErbB4 receptor binding and activating fragment thereof, is useful in the treatment of diseases in which neural cell growth, proliferation and/or differentiation alleviate symptoms of the disease. The NRG3 may be the full length amino acid sequence of the murine NRG3 (SEQ ID NO:2) or the human NRG3s (SEQ ID NO:6 or SEQ ID NO:23); the full length amino acid sequence from another mammalian species having at least approximately 75% homology to the murine and human NRG3 at the amino acid level, preferably about 90% amino acid sequence homology in the EGF-like binding domain; and an amino acid sequence comprising the EGF-like domain of NRG3, which sequence binds to the ErbB4 receptor. Where the NRG3 or ErbB4 receptor binding fragment is agonist, the NRG3 or fragment binds to and activates ErbB4 receptor. Where the NRG3 or fragment is an antagonist, the NRG3 or fragment binds to but does not activate ErbB4 receptor, thereby preventing activation by the naturally occurring NRG3 or agonist.

Diseases treatable by administration of NRG3 or an agonist thereof (such as a polypeptide comprising an NRG3

EGF-like domain) include, but are not limited to, disorders that may arise in a patient in whom the nervous system has been damaged by, e.g., trauma, surgery, stroke, ischemia, infection, metabolic disease, nutritional deficiency, malignancy, or toxic agents; motoneuron disorders, such as amyotrophic lateral sclerosis (Lou Gehrig's disease), Bell's palsy, and various conditions involving spinal muscular atrophy, or paralysis; human "neurodegenerative disorders", such as Alzheimer's disease, Parkinson's disease, epilepsy, multiple sclerosis, Huntington's chorea, Down's Syndrome, nerve deafness, and Meniere's disease; neuropathy, and especially peripheral, referring to a disorder affecting the peripheral nervous system, most often manifested as one or a combination of motor, sensory, sensorimotor, or autonomic neural dysfunction, such as distal sensorimotor neuropathy, or autonomic neuropathies including reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine. Also, NRG3 or biologically active fragments thereof (such as an EGF-like domain of an NRG3) may be used to treat diseases of skeletal muscle of smooth muscle, such as muscular dystrophy or diseases caused by skeletal or smooth muscle wasting.

Semipermeable, implantable membrane devices are useful as means for delivering drugs in certain circumstances. For example, cells that secrete soluble NRG3, or agonist thereof, or chimeras can be encapsulated, and such devices can be implanted into a patient, for example, into the brain of patients suffering from Parkinson's Disease. See, U.S. Pat. No. 4,892,538 of Aebischer et al.; U.S. Pat. No. 5,011, 472 of Aebischer et al.; U.S. Pat. No. 5,106,627 of Aebischer et al.; PCT Application WO 91/10425; PCT Application WO 91/10470; Winn et al. (1991) Exper. Neurology 113:322–329; Aebischer et al. (1991) Exper. Neurology 111:269–275; and Tresco et al. (1992) ASAIO 38:17–23. Accordingly, also included is a method for preventing or treating damage to a nerve or damage to other NRG3-expressing or NRG3-responsive cells, e.g. brain, heart, or kidney cells, as taught herein, which method comprises implanting cells that secrete NRG3, or fragment or agonist thereof, or antagonist as may be required for the particular condition, into the body of patients in need thereof. Finally, the present invention includes an implantation device, for preventing or treating nerve damage or damage to other cells as taught herein, containing a semipermeable membrane and a cell that secretes NRG3, or fragment or agonist thereof, (or antagonist as may be required for the particular condition) encapsulated within the membrane, the membrane being permeable to NRG3, or fragment agonist thereof, and impermeable to factors from the patient detrimental to the cells. The patient's own cells, transformed to produce NRG3 ex vivo, could be implanted directly into the patient, optionally without such encapsulation. The methodology for the membrane encapsulation of living cells is familiar to those of ordinary skill in the art, and the preparation of the encapsulated cells and their implantation in patients may be accomplished readily as is known in the art. The present invention includes, therefore, a method for preventing or treating cell damage, preferably nerve damage, by implanting cells into the body of a patient in need thereof, the cells either selected for their natural ability to generate NRG3, or fragment or agonist thereof, or engineered to secrete NRG3, or fragment or agonist thereof. Preferably, the secreted NRG3 is soluble, human NRG3 when the patient is human. The implants are preferably non-immunogenic and/or prevent immunogenic implanted cells from being recognized by the immune system. For CNS delivery, a preferred location for the implant is the cerebral spinal fluid of the spinal cord.

The administration of the NRG3, fragment or variant thereof, of the present invention can be done in a variety of ways, e.g., those routes known for specific indications, including, but not limited to, orally, subcutaneously, intravenously, intracerebrally, intranasally, transdermally, intraperitoneally, intramuscularly, intrapulmonary, vaginally, rectally, intraarterially, intralesionally, intraventricularly in the brain, or intraocularly. The NRG3 may be administered continuously by infusion into the fluid reservoirs of the CNS, although bolus injection is acceptable, using techniques well known in the art, such as pumps or implantation. Sustained release systems can be used. Where the disorder permits, one may formulate and dose the NRG3 variant for site-specific delivery. Administration can be continuous or periodic. Administration can be accomplished by a constant- or programmable-flow implantable pump or by periodic injections.

Semipermeable, implantable membrane devices are useful as means for delivering drugs in certain circumstances. For example, cells that secrete soluble NGF variant can be encapsulated, and such devices can be implanted into a patient, for example, into the brain or spinal chord (CSF) of a patient suffering from Parkinson's Disease. See, U.S. Pat. No. 4,892,538 of Aebischer et al.; U.S. Pat. No. 5,011,472 of Aebischer et al.; U.S. Pat. No. 5,106,627 of Aebischer et al.; PCT Application WO 91/10425; PCT Application WO 91/10470; Winn et al. (1991) Exper. Neurology 113:322–329; Aebischer et al. (1991) Exper. Neurology 111:269–275; and Tresco et al. (1992) ASAIO 38:17–23. Finally, the present invention includes an implantation device, for preventing or treating nerve damage or damage to other cells as taught herein, containing a semipermeable membrane and a cell that secretes an NRG3, the cell being encapsulated within the membrane, and the membrane being permeable to NRG3, but impermeable to factors from the patient detrimental to the cells. The patient's own cells, transformed to produce NRG3 ex vivo, optionally could be implanted directly into the patient without such encapsulation. The methodology for the membrane encapsulation of living cells is familiar to those of ordinary skill in the art, and the preparation of the encapsulated cells and their implantation in patients may be accomplished readily as is known in the art. Preferably, the secreted NRG3, fragment or variant thereof, is a human NRG3 when the patient is human. The implants are preferably non-immunogenic and/ or prevent immunogenic implanted cells from being recognized by the immune system. For CNS delivery, a preferred location for the implant is the cerebral spinal fluid of the spinal cord.

The pharmaceutical compositions of the present invention comprise a NRG3 in a form suitable for administration to a patient. In the preferred embodiment, the pharmaceutical compositions are in a water soluble form, and may include such physiologically acceptable materials as carriers, excipients, stabilizers, buffers, salts, antioxidants, hydrophilic polymers, amino acids, carbohydrates, ionic or nonionic surfactants, and polyethylene or propylene glycol. The NRG3 may be in a time-release form for implantation, or may be entrapped in microcapsules using techniques well known in the art.

An effective amount of NRG3 or NRG3 agonist or antagonist to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 10 ng/kg to up to 100 mg/kg of patient body weight or more per day, preferably about 1 µg/kg/day to 10 mg/kg/day. Typically, the clinician will administer NRG3 or NRG3 agonist or antagonist until a dosage is reached that achieves the desired effect for treatment of the above mentioned disorders.

L. Transgenic and Knockout Animals

Nucleic acids which encode novel NRG3 from non-human species, such as the murine NRG3, can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, murine cDNA encoding NRG3 or an appropriate sequence thereof can be used to clone genomic DNA encoding NRG3 in accordance with established techniques and the genomic sequences used to generate transgenic animals that contain cells which express DNA encoding NRG3. Methods for generating transgenic animals, particularly animals such as mice, have become conventional in the art and are described, for example, in U.S. Pat. Nos. 4,736,866 and 4,870,009. Typically, particular cells, such as neuronal cells, would be targeted for NRG3 transgene incorporation with tissue-specific enhancers, which could result in altered cell differentiation, cell proliferation, or cellular apoptosis, depending upon the ligand interaction with the expressed polypeptide. Transgenic animals that include a copy of a transgene encoding NRG3 introduced into the germ line of the animal at an embryonic stage can be used to examine the effect of increased expression of DNA encoding NRG3. Such animals can be used as tester animals for reagents thought to confer protection from, for example, diseases associated with abnormal neuronal differentiation and neuronal cell proliferation, for example. In accordance with this facet of the invention, an animal is treated with the reagent and a reduced incidence of the disease, compared to untreated animals bearing the transgene, would indicate a potential therapeutic intervention for the disease.

Alternatively, the non-human homologues of NRG3 can be used to construct a NRG3 "knock out" animal which has a defective or altered gene encoding NRG3 as a result of homologous recombination between the endogenous gene encoding NRG3 and altered genomic DNA encoding NRG3 introduced into an embryonic cell of the animal. For example, murine cDNA encoding NRG3 can be used to clone genomic DNA encoding NRG3 in accordance with established techniques. A portion of the genomic DNA encoding NRG3 can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, Cell 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., Cell 69: 915 (1992)). The selected cells are then injected into a blastocyst of an animal (e.g., a mouse) to form aggregation chimeras (see, e.g., Bradley, in *Teratocarcinomas and Embryonic Stem Cells: A Practical Approach*, E. J. Robertson, ed. (IRL, Oxford, 1987), pp. 113–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be used in the selection of potential therapeutic agents, such as NRG3 agonists, that restore the cellular processes initiated or maintained by native NRG3; or the knockout animals can be used in the study of the effects of nrg3 mutations.

The instant invention is shown and described herein in what is considered to be the most practical, and the preferred embodiments. It is recognized, however, that departures may be made therefrom which are within the scope of the invention, and that obvious modifications will occur to one skilled in the art upon reading this disclosure.

EXAMPLES

The following examples are provided so as to provide those of ordinary skill in the art with a complete disclosure and description of how to make the compounds and compositions of the invention and how to practice the methods of the invention and are not intended to limit the scope of what the inventors regard as their invention. Efforts have been made to insure accuracy with respect to numbers used (e.g. amounts, temperature, etc.), but some experimental errors and deviation should be accounted for. Unless indicated otherwise, parts are parts by weight, temperature is in degrees C., and pressure is at or near atmospheric.

Example 1

Molecular Cloning of a Mouse and Human Novel NRG3

Novel NRG3 cDNAs were identified using an expressed sequence tag shown below: AATTTCTGCCGAAAACT-GATTCCATCTTATCGGATCCAACAGACCACTTGGGG ATTGAATTCATGGAGAGTGAAGAAGTTTATCAAAG GCAGGTGCTGTCAATTTCATGTATCATCTTTGGAAT TGTCATCGTGGGCATGTTCTGTGCAGCATTCTACTT CAAAAGCAAGAAACAAGCTAAACAAATCCAAGAG CAGCTGAAAGTGCCACAAAATGGTAAAAGCTACA GTCTCAAAGCATCCAGCACAATGGCAAAGTCAGA GAACTTGGTGAAGAGCCATGTCCAGCTGCAAAAT AAAATGTCAGGCTTCTGAGCCCAAGCTAAGCCAT CATATCCCCTGTNGACCTGCACGTGCACATCCNGA TGGCCCGTTTCCTGCCTTTTNTGATGACATTTNCAC CACAAATGNAGTGAAAATGGGNCTTTTCNTGCCTT AACTGGTTGACNTTTTTNC CCCAAAAGGAG (EST; SEQ ID NO:21; Genbank entry H23651) from the National Center for Biotechnology Information (NCBI) database of ESTs. This EST from a human brain cDNA library, encodes an amino acid sequence having approximately 62% identity to amino acids 232–316 of heregulin-β1 (also designated neuregulin-β1, or NRG1).

To obtain a partial human cDNA clone, a 50-base single stranded oligonucleotide probe (5'-TGGTAAAAGCTA-CAGTCTCAAAGCATCCAGCACAATGGCAAAGTCA GAGA-3'; SEQ ID NO:18) was synthesized based on the EST sequence. The probe was used to screen 1.5×10⁶ plaques from a λgt10 cDNA library prepared from human fetal brain RNA (HL3003a, Clontech) as described by Godowski et al. (Godowski, P. J. et al. (1989) PNAS USA 86:8083–8087, herein incorporated by reference in its entirety). Nine positive plaques were obtained and the sequences of both strands of the largest inserts were determined by standard sequencing techniques. From these cloned overlapping sequences, a partial cDNA sequence of the human NRG3 was obtained.

Additional 5' human NRG3 sequence was obtained by anchored PCR of human hippocampus RNA (Clontech). The complete human open reading frame nucleic acid sequence deduced from direct sequencing of hNRG3B1 cDNA is shown in FIG. 2 (SEQ ID NO:5). ATCC 209157 is nucleic acid comprising an expression vector and the nucleotide sequence of the human NRG3B1 open reading frame. An alternatively spliced form of human NRG3 was cloned as pRK5.tk.neo.hNRG3B2 (SEQ ID NO:22) encoding the deduced amino acid sequence of SEQ ID NO:23, which amino acid sequence lacks amino acids 529 to 552 of SEQ ID NO:6 (see FIG. 4B). Since this alternatively spliced form of human NRG3 comprises the EGF-like domain of the other NRG3s as well as high amino acid sequence homology, it is expected to exhibit the biological properties of the NRG3s disclosed herein.

To clone murine NRG3 cDNA sequences, two degenerate primers were designed based on regions proximal to the transmembrane domain of the partial human cDNA, encoding the amino acid sequences NDGECFVI (SEQ ID NO:19) and EFMESEEVY (SEQ ID NO:20). A mouse brain cDNA library (Clontech, ML1042a) was screened, and a clone (C5a) containing a partial murine NRG3 cDNA was obtained by standard techniques. Using a probe derived from the C5a sequence, two additional mouse brain cDNA libraries (ML1034h, Clontech; and 936309, Stratagene) were screened. Both strands of two overlapping murine partial NRG3 clones, SWAJ-3 and ZAP-1 were sequenced and, together were found to encode an entire open reading frame (ORF) of 2139 bp having the DNA sequence SEQ ID NO:1 and the deduced amino acid sequence SEQ ID NO:2 shown in FIG. 4A. Nucleic acid comprising the murine NRG3 open reading frame cloned into an expression vector is designated pLXSN.mNRG3 (ATCC 209156).

The chromosomal localization of human NRG3 was mapped to 10q22 by PCR analysis of somatic cell hybrid DNA, whereas the NRG1 gene is located at 8p11-22 (Lee, J. and Wood, W. I. (1993) Genomics 16:790–791; and Orr-Urtreger, A. et al. (1993) Proc. Natl. Acad. Sci. USA 90:1867–1871). Thus, NRG3 is a novel member of the EGF-like family of protein ligands.

Example 2

Characterization of the Mouse and Human NRG3 Deduced Amino Acid Sequences

The cDNAs of human and murine NRG3 contained open reading frames encoding proteins of 720 and 713 amino acids respectively, with predicted MW of 77,901 Da for human NRG3 and 77,370 Da for murine NRG3 (FIG. 4). The two species of NRG3 are 93% identical in amino acid sequence.

Figure 5:
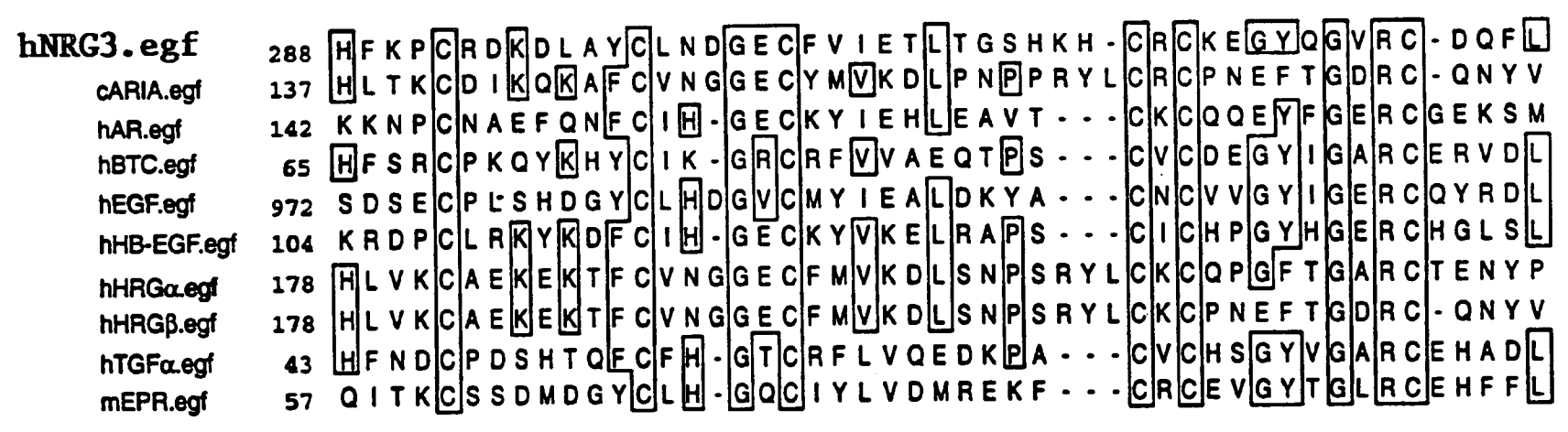

Analysis of the amino acid sequence of human NRG3 revealed that it contained homology to NRG1 family members (i.e. 23% and 19% sequence identity to SMDF (Ho, W. H. et al. (1995) J. Biol. Chem. 270:14523–32) and heregulin-β1 (Holmes, W. E. et al. (1992) Science 256:1205–10) respectively). A hydropathy analysis indicated two hydrophobic segments: $W^{66}$-$V^{91}$ and $L^{362}$-$F^{383}$ (amino acid numbers according to human NRG3). Similar to NRG1, the C-terminal hydrophobic segment may serve as the transmembrane domain and the N-terminal region may act as internal signal sequence (Wickner, W. T. and Lodish, H. F. (1985) Science 230:400–7; Sabatini, D. D. et al. (1982) J. Cell Biol. 92:1–22; and Blobel, G. (1980) Proc. Natl. Acad. Sci. USA 77:1496–500). In contrast to many neuregulin family members, the extracellular domain of NRG3 is devoid of Ig-like or kringle domains. Instead, NRG3 contains a unique Ala/Gly rich segment at the N-terminus, a mucin-like Ser/Thr rich region containing abundant sites for O-linked glycosylation, and an EGF motif. There are no predicted sites for N-linked glycosylation. The EGF-like domain of NRG3 is distinct from those encoded by the NRG1 (31% identity compared with neuregulin-β1 EGF-like domain) and NRG2 (39% identity with neuregulin-β1 EGF-like domain), suggesting that NRG3 is not an alternatively spliced NRG1 isoform. A diagrammatic comparison of EGF-like domains of EGF family members is shown in FIG. 5. The putative intracellular domain of NRG3 contains only approximately 13% sequence identity to the intracellular domain of NRG1. The EGF-like domains of the EGF family members were obtained from the following sources, each reference herein incorporated by reference in its entirety. The sequences compared in FIG. 5 include the EGF-like domain of human NRG3 (hNRG3.egf; SEQ ID NO:4; disclosed herein); chicken ARIA (cARIA.egf; SEQ ID NO:9) (Falls, D. L. et al. (1993) Cell 72:801–815), human amphiregulin (hAR.egf; SEQ ID NO:10) (Plowman, G. D. et al. (1990) Mol. Cell. Biol. 10:1969–81.); human betacellulin (hBTC.egf; SEQ ID NO:11) (Sasada, R. et al. (1993) Biochem. Biophy. Res. Com. 190:1173–9); human EGF (hEGF.egf; SEQ ID NO:12)(Nagai, M. et al. (1985) Gene 36:183–8.); human heparin-binding EGF-like growth factor (hHB-EGF.egf; SEQ ID NO:13) (Higashiyama, S. et al. (1991) Science 251:936–9.); human heregulin-α (hHRGα; SEQ ID NO:14); human heregulin-β (hHRGβ.egf; SEQ ID NO:15)(Holmes, W. E. et al. (1992) Science 256:1205–1210); human TGF-α (hTGFα.egf; SEQ ID NO:16) (Derynck, R. et al. (1984) Cell 38:287–97.); and mouse epiregulin (mEPR.egf; SEQ ID NO:17) (Toyoda, H. et al. (1995) FEBS Lett. 377:403–7.).

Example 3

Expression of Murine and Human NRG3

A. Northern Blot Analysis of Human tissue. The tissue expression profile of the human NRG3 was examined by Northern blot analysis. A multi-tissue RNA blot containing 2 μg each of poly(A)⁺ RNA from human tissues were purchased from Clontech. The region of the human NRG3 nucleic acid sequence encoding amino acids 394 to 536 was used to generate DNA hybridization probes by PCR amplification. The DNA probes were labeled with $\alpha$-$^{32}$P-dCTP by random priming (Promega). The RNA blot was hybridized with 50% formamide, 5×SSC, 50 mM potassium phosphate (pH 7.0), 5× Denhardt's, 10% dextran sulfate at 42° C. for 20 hr. The blot was washed with 0.1×SSC, 0.1% SDS at 50° C. for 30 min and exposed in PhosphoImager™. Expression of NRG3 is mixtures of tissues was used as a guide to determine expression in specific tissues by in situ hybridization.

B. In situ Hybridization Analysis of Mouse Tissues. Formalin-fixed, paraffin-embedded mouse embryos (embryonic days 13, 14, 16), and glutaraldehyde-fixed, paraffin-embedded or paraformaldehyde-fixed, frozen adult mouse brain, ovary, jejunum, kidney, adrenal, lung, stomach, spleen, skeletal muscle, liver and colon were sectioned and processed for in situ hybridization by the method of Lu and Gillett (Lu, L. H. and Gillett, N. A. (1994) Cell Vision 1:169–176) with modifications. Briefly, the in situ hybridization probe was generated by in vitro transcription directly from a PCR fragment, rather than from a plasmid DNA as described. $^{32}$P-UTP-labeled sense and antisense riboprobes were generated by labeling PCR products of a cDNA fragment encoding amino acids $C^{292}$ to $N^{482}$ of murine NRG3.

C. Northern Blot And In Situ Hybridization Analyses Reveal a Neural Expression Pattern of NRG3. A 4.4 kb mRNA transcript that hybridized to the probe derived from amino acids 394 to 536 of human NRG3 was highly expressed in brain. In a Northern blot of various brain tissues, NRG3 expression was detected at high levels in most regions of the brain with the exception of corpus callosum. A lower level expression of a 1.9-kb transcript was detected in testis. The 4.4-kb transcript, but not the 1.9-kb transcript, is of sufficient size to encode NRG3, suggesting that the smaller transcript may encode an alternatively spliced form of NRG3. A similar pattern of expression of NRG3 was observed in RNA blots from murine tissues using a probe derived from the region of murine NRG3 that overlaps the EGF-like domain.

The tissue distribution of NRG3 expression was characterized by in situ hybridization using tissues of embryonic and adult mice. At embryonic day 13 (E13) (the earliest time point examined), NRG3 mRNA was confined to the nervous system. A strong signal for NRG3 mRNA in the brain, spinal cord, trigeminal, vestibular-cochlear and spinal ganglia of embryonic day 16 (E16) mice was also demonstrated. Regions of the telencephalon containing differentiating cells (e.g., the cortical plate) displayed an intense NRG3 signal, whereas the underlying regions containing proliferating or migrating cells (ventricular and subventricular zones), showed little expression. Thus, NRG3 appeared to be expressed mainly in the nervous system of embryonic mice. In adult animals NRG3 antisense probes hybridized to mRNA in spinal cord and numerous brain regions including deep cerebellar nuclei, vestibular nuclei, cerebral cortex, piriform cortex, anterior olfactory nucleus, medial habenula, hippocampus, hypothalamus and thalamus.

Example 4

Characterization of the Binding Characteristics of NRG3 Fragments

A. Expression and Purification of NRG3$^{EGF}$ Fusion Protein in Mammalian Cells To examine the binding characteristics of the NRG3 EGF-like domain as well as to demonstrate the functionality of an NRG3 fragment of the invention, a soluble fusion protein was prepared comprising a sequence of EGF-like domain, which domain has the same amino acid sequence in mouse and human NRG3.

A secreted, epitope tagged polypeptide comprising the EGF-like domain of murine NRG3$_{284-344}$ was constructed by linking in the expressed N-terminal to C-terminal direction 1) the coding sequence for the gD signal sequence and epitope tag (Mark, M. R. et al. (1994) J. Biol. Chem. 269, 10720–10728); 2) the sequences encoding amino acids 284–344 of murine NRG3 (identical to human NRG3 amino acids 282 to 342); and 3) the coding sequences of the Fc portion of human IgG$_1$ in pSAR.SD5 vector (psar.SD5, from A. Shen, Genentech, Inc.). The plasmid encoding these sequences was designated NRG3$^{EGF}$.Fc. The NRG3$^{EGF}$.Fc expression plasmid was transfected using LipofectAMINE (GIBCO/BRL, Bethesda, Md.) into DHFR$^-$ Chinese hamster ovary cells (CHO/DP12; ATCC designation CCL 9096). Clones were selected in glycine/hypoxanthine/thymidine minus medium see, for example, (Sambrook, J. et al., *Molecular Cloning: A Laboratory Manual*, Cold Spring Harbor Laboratory (1989)), pooled, and expanded. The encoded fusion protein was expressed in cultures of the selected clones. Conditioned media from these cells were collected and the recombinant protein purified by a HiTrap protein A affinity column (Pharmacia).

A monomeric fusion protein designated NRG3$^{EGF}$.H6 fusion protein was produced in the same system as the Fc-fusion protein and purified through a cobalt affinity column. NRG3$^{EGF}$.H6 comprises the N-terminal gD tag, murine NRG3$_{284-344}$, and a coding sequence for six histidine residues. Purification was based on the affinity of the histidine side chains for immobilized cobalt using a cobalt affinity column (Cobalt affinity column, R. Vandlen, Genentech, Inc.). Protein concentration was determined by BioRad Protein Assay (BioRad, Richmond, Calif.).

B. Generation of K562$^{erbB}$ Cell Lines. Stable cell lines that expressed human ErbB2, ErbB3 or ErbB4 receptors were derived from K562 cells (K562 cells have ATCC designation CCL 243). cDNAs of human erbB2, erbB3 and erbB4 were from L. Bald and G. Scoffer, Genentech (Sliwkowski, M. et al. (1994), J. Biol. Chem. 269:14661–14665). These cDNAs were subcloned into CMV-based expression vectors and introduced into the K562 human myeloid leukemia cell line by electroporation (1180 mF, 350 V). The transfectants were cultured in RPMI 1640 supplemented with 10% fetal bovine serum, 2 mM glutamine, 100 U/ml penicillin, 100 mg/ml streptomycin, and 10 mM HEPES containing 0.8 mg/ml G418. Resistant clones were obtained by limiting dilution, and receptor expression was confirmed by western blot and NRG binding assays. Receptor expression was confirmed by western blot analysis using antibodies for each of the ErbB receptors (antibodies prepared at Genentech, Inc.) Phorbol ester stimulation was found to significantly enhance receptor expression in both the ErbB3 and ErbB4 transfectants, and the stably transfected K562 cell lines were cultured in medium containing 10 ng/ml Phorbol, 12-Myristate, 12-Acetate-(PMA) overnight prior to use.

C. FACS Analysis. For each binding reaction, 5×10$^5$ stably transfected K562 cells were suspended in PBS/2% BSA at 4° C. for 30 min followed by incubation with 5 µg of isolated, purified NRG3$^{EGF}$.Fc (MW 90 kDa) in a volume of 0.25 ml on ice for 60 min. 1 µg of primary antibody (anti-gD or anti-ErbB receptor) and secondary PE-conjugated (CALTAG, Calif., goat anti-mouse, 1:100 dilution) antibodies were added sequentially with 30–60 min incubation time and extensive washes before each addition. FACS analyses were performed on a Becton & Dickson FACS instrument. Anti-gD (5B6), anti-ErbB2 receptor (4D5), anti-ErbB3 receptor (2F9) and anti-ErbB4 receptor (3B9) monoclonal antibodies were prepared using standard techniques by the Monoclonal Antibody Group, Genentech, Inc.

Figure 6B:
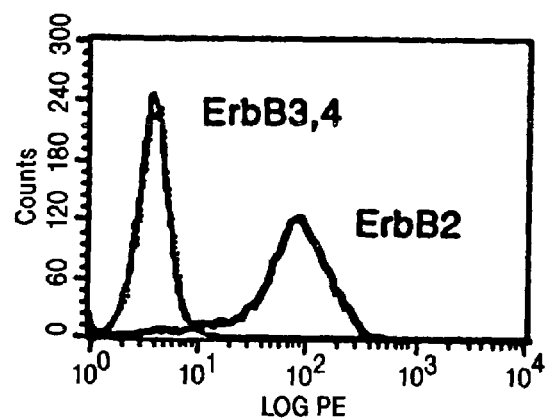
Figure 6C:
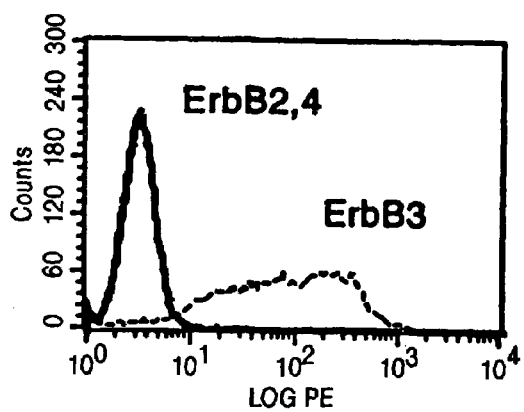
Figure 6D:
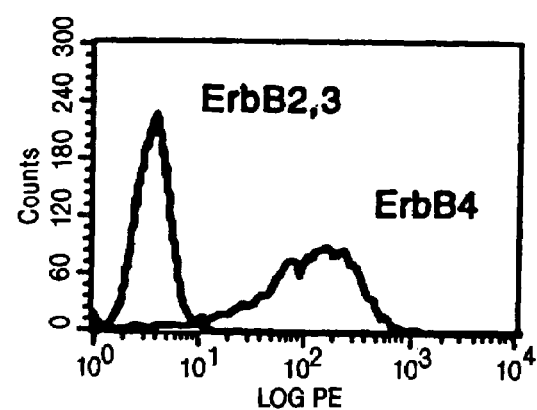

D. The EGF-Like domain of NRG3 Binds Specifically to the ErbB4 Receptor Tyrosine Kinase. To identify the receptor(s) for NRG3, the ability of NRG3 to bind to any of the known neuregulin receptors was investigated. Stable cell lines were generated which expressed receptors ErbB2, ErbB3, or ErbB4. The parental cell line K562 does not express detectable levels of ErbB receptors (FIG. 6A). $K562^{erb2}$, $K562^{erb3}$ and $K562^{erb4}$ cells expressed only the corresponding receptors (FIGS. 6B–6D).

Figure 6E:
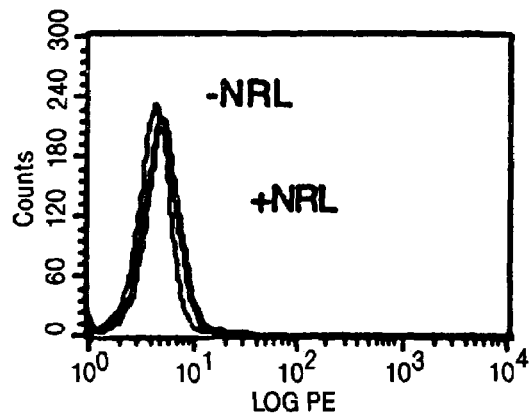
Figure 6F:
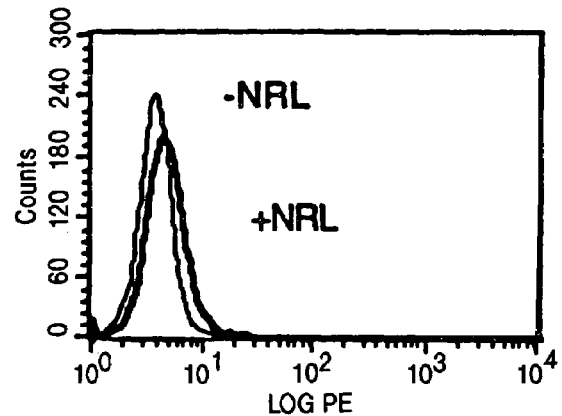
Figure 6G:
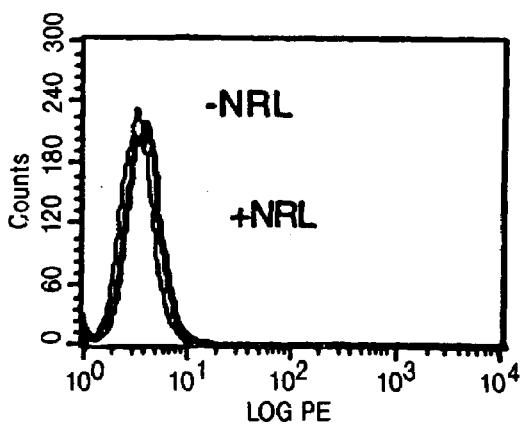
Figure 6H:
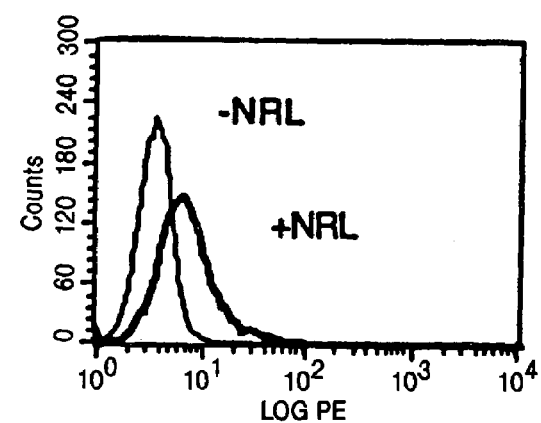

Since the EGF-like domain determines the binding specificity of NRG1 to their receptors, a protein containing an epitope tagged version of the EGF-like domain of NRG3 fused to the Fc portion of human IgG was expressed and purified. Using a FACS assay, it was observed that $NRG3^{EGF}$.Fc bound to cells expressing ErbB4 receptor (FIG. 6H). Binding was specific in that $NRG3^{EGF}$.Fc did not bind to either the parental K562 cells, or cells expressing either ErbB2 or ErbB3 (FIGS. 6E–6G). A control fusion protein, RSE.Fc, did not bind to any of these cell lines. This binding of $NRG3^{EGF}$.Fc to $K562^{erb4}$ cells was competed in a dose-dependent fashion by the EGF-like domain of heregulin-β1 ($NRG1^{EGF}$), but not by RSE.Fc, suggesting that $NRG3^{EGF}$.Fc interacts directly with ErbB4 receptors on the cell surface.

A soluble form of the ErbB4 receptor was co-immunoprecipitated by $NRG3^{EGF}$.Fc in vitro, further demonstrating the binding of $NRG3^{EGF}$.Fc to ErbB4 receptor.

The binding of $NRG3^{EGF}$.Fc to ErbB4 receptor was further analyzed by direct competitive binding assays using $^{125}$I-labeled $NRG3^{EGF}$.Fc. Purified $NRG3^{EGF}$.Fc was radioiodinated using the lactoperoxidase method as described by Sliwkowski et al. (Sliwkowski, M. X. et al. (1994) *J. Biol. Chem.* 269, 14661–5). The average specific activity of the radiolabeled protein was 300 µCi/µg. Binding of $^{125}$I-$NRG3^{EGF}$.Fc to immobilized ErbB4.Fc was competed by either $NRG3^{EGF}$.Fc or EGF domain of $NRG1^{EGF}$ (rHRGβ1$_{177-244}$) in a concentration dependent manner.

The displacement binding assays were performed in Maxisorp C 96-wells (Nunc, Naperville, Ill.). Goat anti-human antibody (Boehringer Mannheim, Germany) was coated on the plate at a concentration of 0.2 µg/well in 100 µl of 50 mM sodium carbonate buffer (pH 9.6) at 4° C., overnight. The plate was blocked by 1% BSA in TBST buffer (25 mM Tris, pH 7.5, 150 mM NaCl, 0.02% Tween 20) for 30 min at room temperature (RT). A soluble form of ErbB4 receptor was added at 15 ng/well in 1% BSA/TBST and incubated for 1.5 hr at RT. To prevent radiolabeled protein from interacting with residual goat anti-human antibodies, 1 µM of a humanized monoclonal antibody (rhuMAB HER2; Carter, P. et al. (1992) *Proc. Natl. Acad. Sci. USA* 89:4285–9) was added to the plate for 20 min and was included in the subsequent binding reaction.

The competitive binding assay was then initiated by the addition of 80 pM (200,000 cpm) of $^{125}$I-$NRG3^{EGF}$.Fc along with various concentrations of unlabeled $NRG3^{EGF}$.Fc or $NRG1^{EGF}$ (*E. coli*-expressed, without Fc). $NRG1^{EGF}$ is the EGF domain of NRG1, corresponding to amino acids 177–244 of the neuregulin-β1 isoform (Holmes, W. E. et al. (1992) *Science* 256:1205–10) and obtained from J. A. Lofgren, Genentech, Inc. The final incubation volume was 100 µl in binding buffer (F-12/DMEM medium, 50 mM HEPES, pH7.5, 2% BSA) and the reaction was allowed to proceed at RT for 1.5 hr. The unbound material was washed by TBST extensively, and the bound radioactivity was counted on a Beckman IsoData gamma-counter (Smith-Kline Beckman, Pa.). Data was analyzed using a nonlinear regression computer program.

Figure 7:
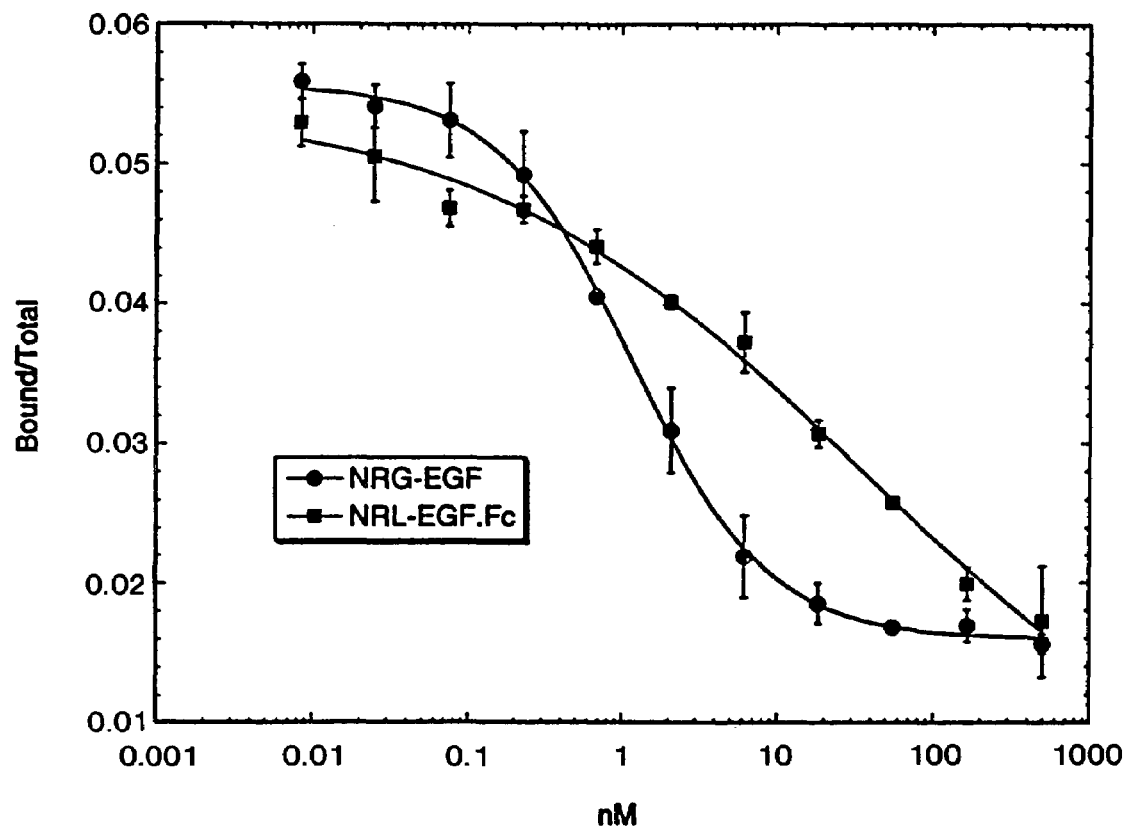
FIG. 7 is a graphical analysis showing competitive inhibition of $^{125}$I-$NRG3^{EGF}$.Fc binding to immobilized soluble ErbB4 receptor by $NRG3^{EGF}$.Fc or $NRG^{EGF}$. Soluble ErbB4 receptor was immobilized on 96-well plates, and was incubated with various concentrations of unlabeled $NRG3^{EGF}$.Fc or $NRG^{EGF}$ and constant amount of $^{125}$I-labeled $NRG3^{EGF}$.Fc for 1.5 hour at room temperature. The fraction of radioactivity bound over total $^{125}$I-$NRG3^{EGF}$.Fc input is plotted against the concentration of competitor. Data of a representative experiment from four independent assays is shown. Error bars indicate standard deviation of quadruplicate samples.

Based on the results of the binding experiments as shown in FIGS. 6A–6H, the estimated affinity ($K_i$) for $NRG3^{EGF}$.Fc for binding to ErbB4.Fc was determined to be 9±4 nM (n=4), and the apparent $K_i$ of $NRG1^{EGF}$ was approximately 1 nM. The shallowness of the displacement curve of $NRG3^{EGF}$.Fc may be due to the fact that the $NRG3^{EGF}$.Fc is expressed as a bivalent Fc fusion protein (FIG. 7). The results of the control experiments showed that $^{125}$I-$NRG3^{EGF}$.Fc did not bind control receptor RSE.Fc in the same experiment, and RSE.Fc did not compete $^{125}$I-$NRG3^{EGF}$.Fc bound to ErbB4.Fc.

E. Tyrosine Phosphorylation Assay. NRG1 binds and activates ErbB2, ErbB3 and ErbB4 receptor resulting in tyrosine phosphorylation and downstream signaling events (Sliwkowski, M. X., et al. (1994), supra; Plowman, G. D. et al. (1993) supra; and Carraway, K. L. and Cantley, L. C. (1994), surpa). As demonstrated in the preceding example, NRG3 binds ErbB4 receptor, but not ErbB2 or ErbB3 receptors at a detectable level. The ability of the EGF-like domain of NRG3 ($NRG3^{EGF}$) to activate ErbB4 receptor, $K562^{erbB4}$ cells was examined.

$K562^{erbB4}$ cells or MDA-MB-453 cells (negative control; ATCC designation HB 131) were cultured in medium lacking serum for 12 hours and then stimulated with $NRG3^{EGF}$.Fc, $NRG^{EGF}$.H6 or $NRG1^{EGF}$. $K562^{erbB4}$ cells were treated with 2.5 nM or 25 nM of $NRG3^{EGF}$.Fc for 3 min or 8 min. As a positive control, the cells were similarly treated with $NRG1^{EGF}$.

ErbB4 receptor tyrosine phosphorylation was detected by immunoprecipitation and Western blot according to the following procedure. Cells were lysed with lysis buffer (20 mM Tris, pH 7.5, 100 mM NaCl, 30 mM NaF, 2 mM EDTA, 2 mM EGTA, 0.1% SDS, 1% Triton X-100, 2 mM sodium vanadate, 2 mM sodium molybdate, 2 mM of PMSF). After removing cell debris by centrifugaton, 1 µg of anti-ErbB4 receptor monoclonal antibody (C-18, Santa Cruz Biotechnology, Santa Cruz, Calif.) was added together with 20 µl of protein A-agarose slurry (Sigma, St. Louis, Mo.). Immunoprecipitation was performed at 4° C. overnight, complexes were collected by centrifugation and washed three times with 1 ml lysis buffer. Proteins were separated by reducing SDS-polyacrylamide gel electrophoresis (SDS-PAGE) on Novex 4%–12% minigels and transferred to nitrocellulose. The blots were probed with peroxidase conjugated anti-phosphotyrosine antibody (Transduction Laboratory). The blot was stripped and reprobed with anti-ErbB4 receptor antibody followed by peroxidase conjugated goat anti-rabbit IgG antibody (Sigma) to visualize ErbB4 receptor proteins.

Based on these experiments, it was demonstrated that $NRG3^{EGF}$.Fc stimulated ErbB4 receptor tyrosine phosphorylation at both time points and in a dose dependent manner.

To confirm the ability of $NRG3^{EGF}$ to activate the ErbB4 receptor tyrosine phosphorylation, receptor activation in the human breast cancer cell line MDA-MB-453 was examined. This cell line expresses high level of ErbB2 and ErbB3 receptors, and low levels of ErbB4 receptor. Treatment of MDA-MB-453 cells with $NRG3^{EGF}$.Fc or with a monomeric form of the EGF domain ($NRG3^{EGF}$.H6) resulted in substantial increase of tyrosine phosphorylation of ErbB4 receptor.

NRG family members and other members in the EGF family display a complex pattern of receptor binding. In most cases, one ligand is able to bind several combinations of receptor homo- and heterodimers (Karunagaran, D. et al. (1996) *EMBO J.* 15:254–264,Beerli, R. R. and Hynes, N. E. (1996) *J. Biol. Chem.* 271:6071–6076). For example, NRGs bind ErbB2/ErbB3 receptor heterodimers and ErbB4/ErbB4 receptor homodimers with high affinity but ErbB3/ErbB3 receptor homodimers with low affinity (Sliwkowski, M. X. et al. (1994) *J. Biol. Chem.* 269, 14661–5, Carraway, K. L. and Cantley, L. C. (1994) *Cell* 78, 5–8, Tzahar, E. et al. (1994) *J. Biol. Chem.* 269, 25226–33, Carraway, K. L. r. et al. (1994) *J. Biol. Chem.* 269, 14303–6, and Kita, Y. A. et al. (1994) *FEBS Lett.* 349, 139–43). Betacellulin binds both EGFR and ErbB4 homodimers (Riese, D. J. et al. (1995) Mol. Cell. Biol. 15:5770–6). The EGF-like domains of EGF and NRG1 family members determine the specificity of receptor activation (Barbacci, E. G. et al. (1995) J. Biol. Chem. 270:9585–9589). The limited amino acid sequence homology in the EGF-like domains of NRG3 and NRG1 suggests that NRG3 may have a different spectrum of receptor interactions relative to members of the NRG family, but with potentially overlapping binding sites, since binding of the EGF-like domain of NRG3 to ErbB4 can be competed by the EGF-like domain of NRG1.

NRG3$^{EGF}$.Fc did not bind to K562 cells that express either ErbB2 or ErbB3 (FIGS. 6E–6G), or to MDA-MB-486 cells which express high levels of the EGFR. An increase in phosphorylation of either the EGFR, ErbB2 or ErbB3 in MDA-MB-453 cells treated with NRG3 also was not observed.

Most variants of NRGs, with the exception of the neural specific form of SMDF, are widely expressed in numerous tissues including brain, heart, skeletal muscle, breast, liver, lung, among others. Betacellulin, a ligand for both EGFR and ErbB4, also displays broad tissue expression patterns (Shing, Y. et al. (1993) *Science* 259, 1604–7; Sasada, R. et al. (1993) *Biochem. Biophy. Res. Com.* 190, 1173–9). In contrast, the expression of NRG3 is strikingly restricted to neural tissues as disclosed herein by Northern analysis and in situ hybridization. Developmentally, NRG3 mRNA can be detected as early as E11 (but not E4) in mouse as judged by Northern blot and E13 by in situ hybridization (the earliest age examined). ErbB4 is predominantly expressed in brain, heart and skeletal muscle (Plowman, G. D. et al. (1993) *Proc. Natl. Acad. Sci. USA* 90, 1746–50). ErbB4 was also shown to be broadly distributed in the brains of chick embryos (E14, E17, predominantly in neurons) (Francoeur, J. R. et al. (1995) *J. Neur. Res.* 41, 836–45), in rat retina cultures (Bermingham-McDonogh, O. et al. (1996) *Development* 122, 1427–38.), at neuromuscular synapses (Zhu, X. et al. (1995) *EMBO J.* 14, 5842–8.), but not in cultured human and rat Schwann cells (Grinspan, J. B. et al. (1996) *J. Neuroscience* 16, 6107–6118,Levi, A. D. et al. (1995) *J. Neuroscience* 15, 1329–40.). Recently, ErbB4 was found to co-localize with GABA$^+$ cells (Weber, J. et al. (1996) *Soc Neurosci Abstr* 22, 1579.). Thus, the same receptor may mediate distinct biological functions in different tissues or cell types when interacted with corresponding tissue-specific ligands. For example, NRG1 may serve as a ligand for ErbB4 during heart development, betacellulin may act as a mitogenic ligand for ErbB4 in variety of cell types, while neural specific ligand(s) (such as NRG3) may function as trophic or guidance molecules on ErbB4 receptor expressing cells in the central or peripheral nervous systems.

Example 5

Binding and ErbB4 Receptor Tyrosine Kinase Activation by Full Length Mouse and Human NRG3s A full length murine NRG3 or human NRG3 was synthesized based on the murine and human consensus nucleic acid sequences SEQ ID NO:1 and SEQ ID NO:5, respectively and the NRG3s were expressed as amino acid sequences. Based on the experiments described herein for the characterization of NRG3-EGF binding and ErbB4 receptor activation, analogous experiments are performed for the full length consensus NRG3 from mouse and human sources. Adjustments to the reaction conditions are made to optimize pH, solutes and their concentrations, and other relevant parameters to allow ErbB4 receptor-binding of the full length consensus NRG3 and ErbB4 receptor activation.

Alternatively, a murine or human NRG3 polypeptide fragment comprising the EGF-like domain but lacking the transmembrane domain is synthesized and tested for ErbB4 receptor binding and activation as described herein. Such a NRG3 fragment may, for example, include the extracellular domain of a NRG3, which extracellular domain contains the EGF-like domain.

A NRG3 extracellular domain may optionally be fused to an immunoglobulin constant region, as shown herein for the NRG3-EGF-Fc fusion proteins. As an Fc fusion protein, the NRG3 extracellular domain-Fc protein is expected to form a dimer. The immunoglobulin constant region is preferably from IgG, but may also be taken from IgM, IgA and IgE and remain within the scope of the invention.

Where a monomeric fusion protein is desired that retains binding activity or binding and activation ability, the extracellular domain is fused to, for example, a series of histidine residues as disclosed herein for the NRG3-EGF-H6 immunoadhesion.

Adjustments to the binding reaction conditions are made to optimize pH, solutes and their concentrations and other relevant parameters to allow ErbB4 receptor-binding of the NRG3 fragment and ErbB4 receptor activation.

Example 6

Enhancement of Cellular Proliferation

Enhancement of cellular proliferation is exemplified by the following assay in which cells expressing ErbB4 receptor on their surface are treated with NRG3. It is understood that according to the invention, the cells may be treated with a NRG3 fragment (such as the NRG3 EGF-like domain) or a NRG3 variant.

As an example, rat retina cells which naturally express ErbB4 receptor (Bermingham-McDonogh, O. et al. (1996) Development 122, 1427–38) are cultured by standard techniques. The cultured cells are contacted with NRG3 in a dose dependent manner and an increase in cell number (e.g. a 30% percent increase at 48 hours) and EC50 is determined.

NRG3 treatment may also alter the morphology of these cells; untreated cells were multipolar with numerous branched processes whereas NRG3-treated cells may become spindle-shaped smooth processes and/or align themselves in a parallel array.

NRG3 is believed to stimulate neuronal cell growth in a dose dependent manner. NRG3 alone is expected to produce a significant increase in neuronal cell number compared to control medium. A synergistic effect may be observed between other neuronal proliferation enhancers such as gas6 (growth arrest-specific gene; see, for example, Schneider et al., Cell 54:787–793 (1988); and Manfioletti et al. in Molec. Cell Biol. 13(8):4976–4985 (1993)) and/or heregulin. NRG3 is expected to increase both cell number and thymidine incorporation as measures of cell proliferation.

NRG3 is expected to have an effect on cell morphology as determined by viewing phase contrast micrographs of ErbB4 receptor-expressing neuronal cells grown in various media containing NRG3 alone or NRG3 plus other cell proliferation enhancing compounds such as heregulin, gas6, fetal bovine serum, and the like. Photomicrographs are taken after 96 hours of culture. The cells grown in the presence of NRG3 are expected to have processes which are not observed in cells grown in the absence of NRG3.

Cells are stained by immunofluorescence for markers specific for the cultured neuronal cells. Briefly, passaged ErbB4 receptor-expressing neuronal cells are contacted with NRG3 and cultured for 24 hours on laminin coated Chamber slides and fixed in 10% formalin in PBS. Fixed cells are blocked with 10% goat serum and incubated with rabbit derived anti-marker antibody at dilutions recommended by the distributor. Specific binding of the primary antibody is observed by staining with goat anti-rabbit IgG $(Fab')_2$-FITC conjugates. Cells are counter-stained with DNA dye propidium iodide. Negative controls are run on WI-38 cells which stain negative. Cells grown under these conditions are expected to show 100% immunofluorescent staining for the cell markers.

The ability of NRG3 to stimulate proliferation in ErbB4 receptor-expressing neuronal cells through the ErbB4 tyrosine kinase receptors may be investigated as follows. Cells are stimulated with various amounts of NRG3 (for example, 0 to 200 nM) for 15 min in a 37° C. incubator. Cell lysates are prepared and immunoprecipitated with an anti-ErbB4 receptor antibody. Tyrosine phosphorylation of ErbB4 receptor is detected with 4G10 anti-phosphorylation antibody. Approximately $10^6$ cells are grown to near confluence in defined media. Cells are treated with NRG3 for 15 min in a 37° C. incubator and lysed on ice with 1 ml of lysis buffer (20 mM HEPES, pH7.4, 135 mM NaCl, 50 mM NaF, 1 mM sodium vanadate and 1 mM sodium molybdate, 2 mM EDTA and 2 mM EGTA, 10% glycerol, 1% NP40, 1 $\mu$M okadaic acid, 1 mM PMSF and 1 mM AEBSF). Cell lysates are clarified by centrifuging at 14000×g at 4° C. for 10 min. Immunoprecipitations are performed using approximately 1 $\mu$g of rabbit anti-ErbB4 receptor antibody or 2 $\mu$l of rabbit anti-ErbB4 receptor antiserum. Immunocomplexes are collected with 10 $\mu$l of Protein A Sepharose CL-4B beads. Proteins are separated on Novex 4–12% gradient gel and transferred onto nitrocellulose membrane. Anti-phosphotyrosine immunoblots are performed using 4G10 mouse anti-phosphotyrosine antibody (UBI), goat anti-mouse horseradish peroxidase conjugate and ECL developing kit (Amersham). Addition of NRG3 to ErbB4 receptor-expressing neuronal cells is expected to cause autophosphoralation of ErbB4 receptor tyrosine residue(s).

It is beneficial to have populations of mammalian neuronal cells (preferably human cells) for use as cellular prostheses for transplantation into areas of damaged spinal cord in an effort to influence regeneration of interrupted central axons, for assisting in the repair of peripheral nerve injuries and as alternatives to multiple autografts. See Levi et al., *J. Neuroscience* 14(3):1309–1319 (1994). The use of cell culture techniques to obtain an abundant source of autologous graft material from a small biopsy has already met with clinical success in providing human epidermal cells to cover extensive burns (Gallico et al., N. Eng J. Med. 311:338–451 (1984)). Accordingly, it is expected that the above approach will meet with success in mammals, including humans.

All documents cited throughout the specification as well as the references cited therein are hereby expressly incorporated by reference in their entirety. While the present invention is illustrated with reference to specific embodiments, the invention is not so limited. It will be understood that further modifications and variations are possible without diverting from the overall concept of the invention. All such modifications are intended to be within the scope of the present invention.

Deposit of Material

The following materials have been deposited with the American Type Culture Collection, 10801 University Boulevard, Manassas, Va. 20440-2209(ATCC):

| Material | ATCC Dep. No. | Deposit Date |
| --- | --- | --- |
| mouse NRG3 pLXSN.mNRG3 | 209156 | Jul. 22, 1997 |
| human NRG3B1 pRK5.tk.neo.hNRG3B1 | 209157 | Jul. 22, 1997 |
| human NRG3B2 pRK5.tk.neo.hNRG3B2 | 209297 | Sep. 23, 1997 |

These deposits are made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An immunoadhesin comprising a polypeptide and an immunoglobulin amino acid sequence, the polypeptide comprising an amino acid sequence of the EGF-like domain of SEQ ID NO:4, wherein the polypeptide binds to ErbB4 receptor and activates receptor tyrosine phosphorylation of the ErbB4 receptor.

2. The immunoadhesin of claim 1, wherein the polypeptide is devoid of a cytoplasmic domain, or devoid of a transmembrane domain that can anchor the polypeptide in a cell membrane, or both.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 2538 base pairs
      (B) TYPE: Nucleic Acid
      (C) STRANDEDNESS: Single
      (D) TOPOLOGY: Linear (ix) FEATURE:
      (A) NAME/KEY: mouse NRG3 nucleic acid
      (B) LOCATION: 1-2538
      (C) IDENTIFICATION METHOD:
      (D) OTHER INFORMATION:

(xi) SEQUENCE DESCRIPTION: SEQ ID NO:1:

```
CCTGACCGGC CGGCGGCGCC CGGGCCGGTC TCGCCCCTCT ACCGAGCGCC         50

TCGCCGCCCC CTCCCCGGCC CGCGTCCCCT CCCCCGTCCT CTCCTCCCCG        100

CCCGCCGCCC GCCTCTCGGG GGGAGGGGCG TGGGGCAGG GAGCCGATTT         150

GCATGCGGCC GCCGCGGCCG CTGCCTGAGC CGGAGCCCGC CGCCGCCGGA        200

GCCCGCGCCC GCGCCCGCGC CCGGCCCGCG CGGCCCCATG CCTCTGGCGC        250

GGCCCTCGGG GGGGCGAAGG TGAAGATCGG CTCCTAGGAT GAGTGAAGGG        300

GCGGCCGGTG CCTCGCCACC TGGTGCCGCT TCGGCAGCCG CCGCCTCAGC        350

CGAGGAGGGC ACCGCGGCGG CTGCGGCGGC GGCGGCGGCG GGCGGGGGCC        400

CGGACGGCGG CGGAGAAGGG GCGGCCGAAC CCCCCGGGA GTTACGCTGT         450

AGCGACTGCA TCGTGTGGAA CCGGCAGCAG ACGTGGTTGT GCGTGGTGCC        500

TCTGTTCATC GGCTTCATCG GCCTGGGGCT CAGCCTCATG CTGCTTAAAT        550

GGATCGTGGT AGGCTCCGTC AAGGAGTACG TGCCCACGGA CCTGGTGGAC        600

TCCAAGGGAA TGGGCCAGGA CCCCTTCTTC CTCTCCAAGC CCAGCTCTTT        650

CCCCAAGGCT ATGGAAACCA CCACAACAAC CACTTCTACC ACGTCCCCCG        700

CCACCCCCTC TGCCGGCGGC GCCGCTTCTT CCAGGACGCC TAACCGGATT        750

AGCACCCGCT TGACCACCAT CACACGGGCA CCCACCCGCT TCCCTGGGCA        800

CCGGGTTCCC ATCCGGGCTA GCCCGCGCTC TACCACAGCA CGGAACACTG        850

CTGCCCCTCC GACGGTCCTG TCCACCACGG CCCCTTTCTT CAGTAGCAGC        900

ACGCCCGGCT CCCGACCCCC GATGCCAGGA GCCCCAGTA CGCAGGCGAT         950

GCCTTCCTGG CCCACTGCGG CGTATGCTAC CTCCTCCTAC CTCCACGATT       1000

CCACTCCCTC CTGGACCCTG TCACCCTTTC AGGATGCTGC TGCCGCCTCT       1050

TCCTCCTCAC CCTCTTCCAC CTCCTCCACT ACCACCACCC CAGAAACTAG       1100

CACCAGCCCC AAATTTCATA CTACAACATA CTCCACTGAA CGATCTGAGC       1150

ACTTCAAACC CTGTCGAGAC AAGGACCTGG CGTATTGTCT CAATGATGGT       1200

GAATGCTTTG TGATTGAGAC CCTGACAGGA TCCCATAAGC ACTGTCGGTG       1250

CAAGGAAGGC TACCAAGGAG TCCGTTGTGA TCAATTTCTG CCGAAAACAG       1300

ACTCCATCTT ATCGGATCCA ACAGACCACT GGGGATTGA ATTCATGGAG        1350

AGTGAAGACG TTTATCAAAG GCAGGTGCTG TCAATTTCAT GTATCATCTT       1400
```

-continued

| | |
|---|---|
| TGGAATTGTC ATCGTGGGCA TGTTCTGTGC AGCATTCTAC TTCAAAAGCA | 1450 |
| AGAAACAAGC TAAACAAATT CAGGAGCACC TGAAAGAGTC ACAGAATGGG | 1500 |
| AAGAACTACA GCCTCAAGGC ATCCAGCACA AAGTCTGAGA GCTTGATGAA | 1550 |
| GAGCCATGTC CATCTACAAA ATTATTCAAA GGCGGATAGG CATCCTGTGA | 1600 |
| CTGCGCTGGA GAAAATAATG GAGTCAAGTT TTTCAGCTCC CCAGTCGTTC | 1650 |
| CCAGAAGTCA CTTCTCCTGA CCGAGGAAGC CAGCCTATCA AGCACCACAG | 1700 |
| CCCAGGACAA AGGAGTGGGA TGTTGCATAG GAATACTTTC AGAAGGGCAC | 1750 |
| CACCCTCACC CCGAAGTCGA CTGGGTGGTA TTGTAGGACC AGCATATCAA | 1800 |
| CAACTTGAAG AATCAAGAAT TCCAGACCAG GATACGATAC CTTGCCAAGG | 1850 |
| GATAGAGGTC AGGAAGACTA TATCCCACCT GCCTATACAG CTGTGGTGTG | 1900 |
| TTGAAAGACC CCTGGACTTA AAGTATGTGT CCAATGGCTT AAGAACCCAA | 1950 |
| CAAAATGCAT CAATAAATAT GCAACTGCCT TCAAGAGAGA CAAACCCCTA | 2000 |
| TTTTAATAGC TTGGATCAAA AGGACCTGGT GGGTTATTTA TCCCCAAGGG | 2050 |
| CCAATTCTGT GCCCATCATC CCGTCGATGG GTCTAGAAGA AACCTGCATG | 2100 |
| CAAATGCCAG GGATTTCTGA CGTCAAAAGC ATTAAATGGT GCAAAAACTC | 2150 |
| CTACTCCGCT GACATTGTCA ACGCGAGTAT GCCAGTCAGT GATTGTCTTC | 2200 |
| TAGAAGAACA ACAGGAAGTG AAAATATTAC TAGAGACTGT GCAGGAACAG | 2250 |
| ATCCGGATTC TGACTGATGC CAGACGGTCA GAAGACTTCG AACTGGCCAG | 2300 |
| CATGGAAACT GAGGACAGTC CGAGCGAAAA CACAGCCTTT CTCCCCCTGA | 2350 |
| GTCCCACGGC CAAATCAGAA CGAGAGGCAC AATTTGTCTT AAGAAATGAA | 2400 |
| ATACAAAGAG ACTCTGTGCT AACCAAGTGA CTGGAAATGT AGGAATCTGT | 2450 |
| GCATTATATG CTTTGCTAAA CAGGAAGGAG AGGAAATTAA ATACAAATTA | 2500 |
| TTTATATGCA TTAATTTAAG AGCATCTACT TAGAAGCC | 2538 |

(2) INFORMATION FOR SEQ ID NO:2:

(i) SEQUENCE CHARACTERISTICS:
        (A) LENGTH: 713 amino acids
        (B) TYPE: Amino Acid
        (D) TOPOLOGY: Linear (ix) FEATURE:
        (A) NAME/KEY: Mouse NRG3 (mNRG3)/amino acid seq.
        (B) LOCATION: 1-713
        (C) IDENTIFICATION METHOD:
        (D) OTHER INFORMATION:

(xi) SEQUENCE DESCRIPTION: SEQ ID NO:2:

```
Met Ser Glu Gly Ala Ala Gly Ala Ser Pro Pro Gly Ala Ala Ser
 1               5                  10                  15

Ala Ala Ala Ser Ala Glu Glu Gly Thr Ala Ala Ala Ala
            20                  25                  30

Ala Ala Ala Gly Gly Gly Pro Asp Gly Gly Glu Gly Ala
            35                  40                  45

Ala Glu Pro Pro Arg Glu Leu Arg Cys Ser Asp Cys Ile Val Trp
            50                  55                  60

Asn Arg Gln Gln Thr Trp Leu Cys Val Val Pro Leu Phe Ile Gly
            65                  70                  75

Phe Ile Gly Leu Gly Leu Ser Leu Met Leu Leu Lys Trp Ile Val
```

-continued

```
                   80                  85                  90
Val Gly Ser Val Lys Glu Tyr Val Pro Thr Asp Leu Val Asp Ser
                   95                 100                 105
Lys Gly Met Gly Gln Asp Pro Phe Phe Leu Ser Lys Pro Ser Ser
                  110                 115                 120
Phe Pro Lys Ala Met Glu Thr Thr Thr Thr Thr Ser Thr Thr
                  125                 130                 135
Ser Pro Ala Thr Pro Ser Ala Gly Gly Ala Ala Ser Ser Arg Thr
                  140                 145                 150
Pro Asn Arg Ile Ser Thr Arg Leu Thr Thr Ile Thr Arg Ala Pro
                  155                 160                 165
Thr Arg Phe Pro Gly His Arg Val Pro Ile Arg Ala Ser Pro Arg
                  170                 175                 180
Ser Thr Thr Ala Arg Asn Thr Ala Ala Pro Pro Thr Val Leu Ser
                  185                 190                 195
Thr Thr Ala Pro Phe Phe Ser Ser Thr Pro Gly Ser Arg Pro
                  200                 205                 210
Pro Met Pro Gly Ala Pro Ser Thr Gln Ala Met Pro Ser Trp Pro
                  215                 220                 225
Thr Ala Ala Tyr Ala Thr Ser Ser Tyr Leu His Asp Ser Thr Pro
                  230                 235                 240
Ser Trp Thr Leu Ser Pro Phe Gln Asp Ala Ala Ala Ser Ser
                  245                 250                 255
Ser Ser Pro Ser Ser Thr Ser Ser Thr Thr Thr Pro Glu Thr
                  260                 265                 270
Ser Thr Ser Pro Lys Phe His Thr Thr Tyr Ser Thr Glu Arg
                  275                 280                 285
Ser Glu His Phe Lys Pro Cys Arg Asp Lys Asp Leu Ala Tyr Cys
                  290                 295                 300
Leu Asn Asp Gly Glu Cys Phe Val Ile Glu Thr Leu Thr Gly Ser
                  305                 310                 315
His Lys His Cys Arg Cys Lys Glu Gly Tyr Gln Gly Val Arg Cys
                  320                 325                 330
Asp Gln Phe Leu Pro Lys Thr Asp Ser Ile Leu Ser Asp Pro Thr
                  335                 340                 345
Asp His Leu Gly Ile Glu Phe Met Glu Ser Glu Asp Val Tyr Gln
                  350                 355                 360
Arg Gln Val Leu Ser Ile Ser Cys Ile Ile Phe Gly Ile Val Ile
                  365                 370                 375
Val Gly Met Phe Cys Ala Ala Phe Tyr Phe Lys Ser Lys Lys Gln
                  380                 385                 390
Ala Lys Gln Ile Gln Glu His Leu Lys Glu Ser Gln Asn Gly Lys
                  395                 400                 405
Asn Tyr Ser Leu Lys Ala Ser Ser Thr Lys Ser Glu Ser Leu Met
                  410                 415                 420
Lys Ser His Val His Leu Gln Asn Tyr Ser Lys Ala Asp Arg His
                  425                 430                 435
Pro Val Thr Ala Leu Glu Lys Ile Met Glu Ser Ser Phe Ser Ala
                  440                 445                 450
Pro Gln Ser Phe Pro Glu Val Thr Ser Pro Asp Arg Gly Ser Gln
                  455                 460                 465
Pro Ile Lys His His Ser Pro Gly Gln Arg Ser Gly Met Leu His
                  470                 475                 480
```

```
Arg Asn Thr Phe Arg Arg Ala Pro Pro Ser Pro Arg Ser Arg Leu
                485                 490                 495

Gly Gly Ile Val Gly Pro Ala Tyr Gln Gln Leu Glu Glu Ser Arg
                500                 505                 510

Ile Pro Asp Gln Asp Thr Ile Pro Cys Gln Gly Ile Glu Val Arg
                515                 520                 525

Lys Thr Ile Ser His Leu Pro Ile Gln Leu Trp Cys Val Glu Arg
                530                 535                 540

Pro Leu Asp Leu Lys Tyr Val Ser Asn Gly Leu Arg Thr Gln Gln
                545                 550                 555

Asn Ala Ser Ile Asn Met Gln Leu Pro Ser Arg Glu Thr Asn Pro
                560                 565                 570

Tyr Phe Asn Ser Leu Asp Gln Lys Asp Leu Val Gly Tyr Leu Ser
                575                 580                 585

Pro Arg Ala Asn Ser Val Pro Ile Ile Pro Ser Met Gly Leu Glu
                590                 595                 600

Glu Thr Cys Met Gln Met Pro Gly Ile Ser Asp Val Lys Ser Ile
                605                 610                 615

Lys Trp Cys Lys Asn Ser Tyr Ser Ala Asp Ile Val Asn Ala Ser
                620                 625                 630

Met Pro Val Ser Asp Cys Leu Leu Glu Glu Gln Gln Glu Val Lys
                635                 640                 645

Ile Leu Leu Glu Thr Val Gln Glu Gln Ile Arg Ile Leu Thr Asp
                650                 655                 660

Ala Arg Arg Ser Glu Asp Phe Glu Leu Ala Ser Met Glu Thr Glu
                665                 670                 675

Asp Ser Ala Ser Glu Asn Thr Ala Phe Leu Pro Leu Ser Pro Thr
                680                 685                 690

Ala Lys Ser Glu Arg Glu Ala Gln Phe Val Leu Arg Asn Glu Ile
                695                 700                 705

Gln Arg Asp Ser Val Leu Thr Lys
                710             713

(2) INFORMATION FOR SEQ ID NO:3:

(i) SEQUENCE CHARACTERISTICS:
        (A) LENGTH: 362 amino acids
        (B) TYPE: Amino Acid
        (D) TOPOLOGY: Linear (ix) FEATURE:
        (A) NAME/KEY: mNRG3 extracellular domainAmino acid seq
        (B) LOCATION: 1-362
        (C) IDENTIFICATION METHOD:
        (D) OTHER INFORMATION:

(xi) SEQUENCE DESCRIPTION: SEQ ID NO:3:

Met Ser Glu Gly Ala Ala Gly Ala Ser Pro Gly Ala Ala Ser
  1               5                  10                  15

Ala Ala Ala Ala Ser Ala Glu Glu Gly Thr Ala Ala Ala Ala
                 20                  25                  30

Ala Ala Ala Ala Gly Gly Gly Pro Asp Gly Gly Glu Gly Ala
                 35                  40                  45

Ala Glu Pro Pro Arg Glu Leu Arg Cys Ser Asp Cys Ile Val Trp
                 50                  55                  60

Asn Arg Gln Gln Thr Trp Leu Cys Val Val Pro Leu Phe Ile Gly
                 65                  70                  75
```

```
Phe Ile Gly Leu Gly Leu Ser Leu Met Leu Leu Lys Trp Ile Val
                80                  85                  90
Val Gly Ser Val Lys Glu Tyr Val Pro Thr Asp Leu Val Asp Ser
             95                 100                 105
Lys Gly Met Gly Gln Asp Pro Phe Phe Leu Ser Lys Pro Ser Ser
            110                 115                 120
Phe Pro Lys Ala Met Glu Thr Thr Thr Thr Thr Ser Thr Thr
        125                 130                 135
Ser Pro Ala Thr Pro Ser Ala Gly Gly Ala Ala Ser Ser Arg Thr
            140                 145                 150
Pro Asn Arg Ile Ser Thr Arg Leu Thr Thr Ile Thr Arg Ala Pro
            155                 160                 165
Thr Arg Phe Pro Gly His Arg Val Pro Ile Arg Ala Ser Pro Arg
            170                 175                 180
Ser Thr Thr Ala Arg Asn Thr Ala Ala Pro Pro Thr Val Leu Ser
            185                 190                 195
Thr Thr Ala Pro Phe Phe Ser Ser Ser Thr Pro Gly Ser Arg Pro
            200                 205                 210
Pro Met Pro Gly Ala Pro Ser Thr Gln Ala Met Pro Ser Trp Pro
            215                 220                 225
Thr Ala Ala Tyr Ala Thr Ser Ser Tyr Leu His Asp Ser Thr Pro
            230                 235                 240
Ser Trp Thr Leu Ser Pro Phe Gln Asp Ala Ala Ala Ser Ser
            245                 250                 255
Ser Ser Pro Ser Ser Thr Ser Ser Thr Thr Thr Thr Pro Glu Thr
            260                 265                 270
Ser Thr Ser Pro Lys Phe His Thr Thr Thr Tyr Ser Thr Glu Arg
            275                 280                 285
Ser Glu His Phe Lys Pro Cys Arg Asp Lys Asp Leu Ala Tyr Cys
            290                 295                 300
Leu Asn Asp Gly Glu Cys Phe Val Ile Glu Thr Leu Thr Gly Ser
            305                 310                 315
His Lys His Cys Arg Cys Lys Glu Gly Tyr Gln Gly Val Arg Cys
            320                 325                 330
Asp Gln Phe Leu Pro Lys Thr Asp Ser Ile Leu Ser Asp Pro Thr
            335                 340                 345
Asp His Leu Gly Ile Glu Phe Met Glu Ser Glu Asp Val Tyr Gln
            350                 355                 360
Arg Gln
    362

(2) INFORMATION FOR SEQ ID NO:4:

(i) SEQUENCE CHARACTERISTICS:
        (A) LENGTH: 47 amino acids
        (B) TYPE: Amino Acid
        (D) TOPOLOGY: Linear (ix) FEATURE:
        (A) NAME/KEY: NRG3 EGF-like domain/amino acid seq.
        (B) LOCATION: 1-47
        (C) IDENTIFICATION METHOD:
        (D) OTHER INFORMATION:

(xi) SEQUENCE DESCRIPTION: SEQ ID NO:4:

His Phe Lys Pro Cys Arg Asp Lys Asp Leu Ala Tyr Cys Leu Asn
 1               5                  10                  15
```

-continued

```
Asp Gly Glu Cys Phe Val Ile Glu Thr Leu Thr Gly Ser His Lys
             20                  25                  30

His Cys Arg Cys Lys Glu Gly Tyr Gln Gly Val Arg Cys Asp Gln
             35                  40                  45

Phe Leu
    47
```

(2) INFORMATION FOR SEQ ID NO:5:

(i) SEQUENCE CHARACTERISTICS:
        (A) LENGTH: 2502 base pairs
        (B) TYPE: Nucleic Acid
        (C) STRANDEDNESS: Single
        (D) TOPOLOGY: Linear (ix) FEATURE:
        (A) NAME/KEY: Human NRG3B1(hNRG3B1)/nucleic acid seq.
        (B) LOCATION: 1-2502
        (C) IDENTIFICATION METHOD:
        (D) OTHER INFORMATION:

(xi) SEQUENCE DESCRIPTION: SEQ ID NO:5:

```
TCACCGACCT AGTGGACTCC ACTAGGTCGG TGGGCACGTA CTCCTTGACG        50

GAGCCCACCA CGATCCATTT GAGAAGCATG AGGCGCGGCC CCATGCCTCT       100

GCCGCGGCCC TCGGGGGGGC GAAGGTGAAN ACCGGCTCCT AGGATGAGTG       150

AAGGGGCGGC CGCTGCCTCG CCACCTGGTG CCGCTTCGGC AGCCGCCGCC       200

TCGGCCGAGG AGGGCACCGC GGCGGCTGCG GCGGCGGCAG CGGCGGGCGG       250

GGGCCCGGAC GGCGGCGGCG AAGGGGCGGC CGAGCCCCCC CGGGAGTTAC       300

GCTGTAGCGA CTGCATCGTG TGGAACCGGC AGCAGACGTG GCTGTGCGTG       350

GTACCTCTGT TCATCGGCTT CATCGGCCTG GGGCTCAGCC TCATGCTTCT       400

CAAATGGATC GTGGTGGGCT CCGTCAAGGA GTACGTGCCC ACCGACCTAG       450

TGGACTCCAA GGGGATGGGC CAGGACCCCT TCTTCCTCTC CAAGCCCAGC       500

TCTTTCCCCA AGGCCATGGA GACCACCACC ACTACCACTT CCACCACGTC       550

CCCCGCCACC CCCTCCGCCG GGGGTGCCGC CTCCTCCAGG ACGCCCAACC       600

GGATTAGCAC TCGCCTGACC ACCATCACGC GGGCGCCCAC TCGCTTCCCC       650

GGGCACCGGG TGCCCATCCG GGCCAGCCCG CGCTCCACCA CAGCACGGAA       700

CACTGCGGCC CCTGCGACGG TCCCGTCCAC CACGGCCCCG TTCTTCAGTA       750

GCAGCACGCT GGGCTCCCGA CCCCCGGTGC CAGGAACTCC AAGTACCCAG       800

GCAATGCCCT CCTGGCCTAC TGCGGCATAC GCTACCTCCT CCTACCTTCA       850

CGATTCTACT CCCTCCTGGA CCCTGTCTCC CTTTCAGGAT GCTGCCTCCT       900

CTTCTTCCTC TTCTTCCTCC TCCGCTACCA CCACCACACC AGAAACTAGC       950

ACCAGCCCCA AATTTCATAC GACGACATAT TCCACAGAGC GATCCGAGCA      1000

CTTCAAACCC TGCCGAGACA AGGACCTTGC ATACTGTCTC AATGATGGCG      1050

AGTGCTTTGT GATCGAAACC CTGACCGGAT CCCATAAACA CTGTCGGTGC      1100

AAAGAAGGCT ACCAAGGAGT CCGTTGTGAT CAATTTCTGC CGAAAACTGA      1150

TTCCATCTTA TCGGATCCAA CAGACCACTT GGGGATTGAA TTCATGGAGA      1200

GTGAAGAAGT TTATCAAAGG CAGGTGCTGT CAATTTCATG TATCATCTTT      1250

GGAATTGTCA TCGTGGGCAT GTTCTGTGCA GCATTCTACT TCAAAAGCAA      1300
```

```
GAAACAAGCT AAACAAATCC AAGAGCAGCT GAAAGTGCCA CAAAATGGTA          1350

AAAGCTACAG TCTCAAAGCA TCCAGCACAA TGGCAAAGTC AGAGAACTTG          1400

GTGAAGAGCC ATGTCCAGCT GCAAAATTAT TCAAAGGTGG AAAGGCATCC          1450

TGTGACTGCA TTGGAGAAAA TGATGGAGTC AAGTTTTGTC GGCCCCCAGT          1500

CATTCCCTGA GGTCCCTTCT CCTGACAGAG GAAGCCAGTC TGTCAAACAC          1550

CACAGGAGTC TATCCTCTTG CTGCAGCCCA GGGCAAAGAA GTGGCATGCT          1600

CCATAGGAAT GCCTTCAGAA GGACACCCCC GTCACCCCGA AGTAGGCTAG          1650

GTGGAATTGT GGGACCAGCA TATCAGCAAC TCGAAGAATC AAGGATCCCA          1700

GACCAGGATA CGATACCTTG CCAAGGGATA GAGGTCAGGA AGACTATATC          1750

CCACCTGCCT ATACAGCTGT GGTGTGTTGA AGACCCCTG GACTTAAAGT           1800

ATTCATCCAG TGGTTTAAAA ACCCAACGAA ATACATCAAT AAATATGCAA          1850

CTGCCTTCAA GAGAGACAAA CCCCTATTTT AATAGCTTGG AGCAAAAGGA          1900

CCTGGTGGGC TATTCATCCA CAAGGGCCAG TTCTGTGCCC ATCATCCCTT          1950

CAGTGGGTTT AGAGGAAACC TGCCTGCAAA TGCCAGGGAT TTCTGAAGTC          2000

AAAAGCATCA AATGGTGCAA AAACTCCTAT TCAGCTGACG TTGTCAATGT          2050

GAGTATTCCA GTCAGCGATT GTCTTATAGC AGAACAACAA GAAGTGAAAA          2100

TATTGCTAGA AACTGTCCAG GAGCAGATCC GAATTCTGAC TGATGCCAGA          2150

CGGTCAGAAG ACTACGAACT GGCCAGCGTA GAAACCGAGG ACAGTGCAAG          2200

CGAAAACACA GCCTTTCTCC CCCTGAGTCC CACAGCCAAA TCAGAACGAG          2250

AGGCGCAATT TGTCTTAAGA AATGAAATAC AAAGAGACTC TGCATTGACC          2300

AAGTGACTTG AGATGTAGGA ATCTGTGCAT TCTATGCTTT GCTCAACAGG          2350

AAAGAGAGGA AATCAAATAC AAATTATTTA TATGCATTAA TTTAAGAGCA          2400

TCTACTTAGA AGAAACCAAA TAGTCTATCG CCCTCATATC ATAGTGTTTT          2450

TTAACAAAAT ATTTTTTTAA GGGAAAGAAA TGTTTCAGGA GGGATAAAGC          2500

TT                                                             2502

(2) INFORMATION FOR SEQ ID NO:6:

(i) SEQUENCE CHARACTERISTICS:
        (A) LENGTH: 720 amino acids
        (B) TYPE: Amino Acid
        (D) TOPOLOGY: Linear (ix) FEATURE:
        (A) NAME/KEY: hNRG3B1 amino acid sequence
        (B) LOCATION: 1-720
        (C) IDENTIFICATION METHOD:
        (D) OTHER INFORMATION:

(xi) SEQUENCE DESCRIPTION: SEQ ID NO:6:

Met Ser Glu Gly Ala Ala Ala Ala Ser Pro Pro Gly Ala Ala Ser
 1               5                  10                  15

Ala Ala Ala Ala Ser Ala Glu Glu Gly Thr Ala Ala Ala Ala Ala
                20                  25                  30

Ala Ala Ala Ala Gly Gly Gly Pro Asp Gly Gly Glu Gly Ala
                35                  40                  45

Ala Glu Pro Pro Arg Glu Leu Arg Cys Ser Asp Cys Ile Val Trp
                50                  55                  60

Asn Arg Gln Gln Thr Trp Leu Cys Val Val Pro Leu Phe Ile Gly
```

-continued

```
                65                  70                  75
Phe Ile Gly Leu Gly Leu Ser Leu Met Leu Leu Lys Trp Ile Val
                80                  85                  90
Val Gly Ser Val Lys Glu Tyr Val Pro Thr Asp Leu Val Asp Ser
                95                 100                 105
Lys Gly Met Gly Gln Asp Pro Phe Leu Ser Lys Pro Ser Ser
               110                 115                 120
Phe Pro Lys Ala Met Glu Thr Thr Thr Thr Thr Ser Thr Thr
               125                 130                 135
Ser Pro Ala Thr Pro Ser Ala Gly Ala Ala Ser Ser Arg Thr
               140                 145                 150
Pro Asn Arg Ile Ser Thr Arg Leu Thr Thr Ile Thr Arg Ala Pro
               155                 160                 165
Thr Arg Phe Pro Gly His Arg Val Pro Ile Arg Ala Ser Pro Arg
               170                 175                 180
Ser Thr Thr Ala Arg Asn Thr Ala Ala Pro Ala Thr Val Pro Ser
               185                 190                 195
Thr Thr Ala Pro Phe Phe Ser Ser Ser Thr Leu Gly Ser Arg Pro
               200                 205                 210
Pro Val Pro Gly Thr Pro Ser Thr Gln Ala Met Pro Ser Trp Pro
               215                 220                 225
Thr Ala Ala Tyr Ala Thr Ser Ser Tyr Leu His Asp Ser Thr Pro
               230                 235                 240
Ser Trp Thr Leu Ser Pro Phe Gln Asp Ala Ala Ser Ser Ser Ser
               245                 250                 255
Ser Ser Ser Ser Ser Ala Thr Thr Thr Thr Pro Glu Thr Ser Thr
               260                 265                 270
Ser Pro Lys Phe His Thr Thr Thr Tyr Ser Thr Glu Arg Ser Glu
               275                 280                 285
His Phe Lys Pro Cys Arg Asp Lys Asp Leu Ala Tyr Cys Leu Asn
               290                 295                 300
Asp Gly Glu Cys Phe Val Ile Glu Thr Leu Thr Gly Ser His Lys
               305                 310                 315
His Cys Arg Cys Lys Glu Gly Tyr Gln Gly Val Arg Cys Asp Gln
               320                 325                 330
Phe Leu Pro Lys Thr Asp Ser Ile Leu Ser Asp Pro Thr Asp His
               335                 340                 345
Leu Gly Ile Glu Phe Met Glu Ser Glu Val Tyr Gln Arg Gln
               350                 355                 360
Val Leu Ser Ile Ser Cys Ile Ile Phe Gly Ile Val Ile Val Gly
               365                 370                 375
Met Phe Cys Ala Ala Phe Tyr Phe Lys Ser Lys Gln Ala Lys
               380                 385                 390
Gln Ile Gln Glu Gln Leu Lys Val Pro Gln Asn Gly Lys Ser Tyr
               395                 400                 405
Ser Leu Lys Ala Ser Ser Thr Met Ala Lys Ser Glu Asn Leu Val
               410                 415                 420
Lys Ser His Val Gln Leu Gln Asn Tyr Ser Lys Val Glu Arg His
               425                 430                 435
Pro Val Thr Ala Leu Glu Lys Met Met Glu Ser Ser Phe Val Gly
               440                 445                 450
Pro Gln Ser Phe Pro Glu Val Pro Ser Pro Asp Arg Gly Ser Gln
               455                 460                 465
```

```
Ser Val Lys His His Arg Ser Leu Ser Ser Cys Cys Ser Pro Gly
            470                 475                 480

Gln Arg Ser Gly Met Leu His Arg Asn Ala Phe Arg Arg Thr Pro
                485                 490                 495

Pro Ser Pro Arg Ser Arg Leu Gly Gly Ile Val Gly Pro Ala Tyr
                500                 505                 510

Gln Gln Leu Glu Glu Ser Arg Ile Pro Asp Gln Asp Thr Ile Pro
                515                 520                 525

Cys Gln Gly Ile Glu Val Arg Lys Thr Ile Ser His Leu Pro Ile
                530                 535                 540

Gln Leu Trp Cys Val Glu Arg Pro Leu Asp Leu Lys Tyr Ser Ser
                545                 550                 555

Ser Gly Leu Lys Thr Gln Arg Asn Thr Ser Ile Asn Met Gln Leu
                560                 565                 570

Pro Ser Arg Glu Thr Asn Pro Tyr Phe Asn Ser Leu Glu Gln Lys
                575                 580                 585

Asp Leu Val Gly Tyr Ser Ser Thr Arg Ala Ser Ser Val Pro Ile
                590                 595                 600

Ile Pro Ser Val Gly Leu Glu Glu Thr Cys Leu Gln Met Pro Gly
                605                 610                 615

Ile Ser Glu Val Lys Ser Ile Lys Trp Cys Lys Asn Ser Tyr Ser
                620                 625                 630

Ala Asp Val Val Asn Val Ser Ile Pro Val Ser Asp Cys Leu Ile
                635                 640                 645

Ala Glu Gln Gln Glu Val Lys Ile Leu Leu Glu Thr Val Gln Glu
                650                 655                 660

Gln Ile Arg Ile Leu Thr Asp Ala Arg Arg Ser Glu Asp Tyr Glu
                665                 670                 675

Leu Ala Ser Val Glu Thr Glu Asp Ser Ala Ser Glu Asn Thr Ala
                680                 685                 690

Phe Leu Pro Leu Ser Pro Thr Ala Lys Ser Glu Arg Glu Ala Gln
                695                 700                 705

Phe Val Leu Arg Asn Glu Ile Gln Arg Asp Ser Ala Leu Thr Lys
                710                 715                 720

(2) INFORMATION FOR SEQ ID NO:7:

(i) SEQUENCE CHARACTERISTICS:
        (A) LENGTH: 360 amino acids
        (B) TYPE: Amino Acid
        (D) TOPOLOGY: Linear (ix) FEATURE:
        (A) NAME/KEY: hNRG3 extracellular domain/Amino AcidSeq
        (B) LOCATION: 1-360
        (C) IDENTIFICATION METHOD:
        (D) OTHER INFORMATION:

(xi) SEQUENCE DESCRIPTION: SEQ ID NO:7:

Met Ser Glu Gly Ala Ala Ala Ala Ser Pro Pro Gly Ala Ala Ser
 1               5                  10                  15

Ala Ala Ala Ala Ser Ala Glu Glu Gly Thr Ala Ala Ala Ala Ala
                20                  25                  30

Ala Ala Ala Ala Gly Gly Gly Pro Asp Gly Gly Gly Glu Gly Ala
                35                  40                  45

Ala Glu Pro Pro Arg Glu Leu Arg Cys Ser Asp Cys Ile Val Trp
                50                  55                  60
```

```
Asn Arg Gln Gln Thr Trp Leu Cys Val Pro Leu Phe Ile Gly
                65                  70                  75

Phe Ile Gly Leu Gly Leu Ser Leu Met Leu Leu Lys Trp Ile Val
                80                  85                  90

Val Gly Ser Val Lys Glu Tyr Val Pro Thr Asp Leu Val Asp Ser
                95                 100                 105

Lys Gly Met Gly Gln Asp Pro Phe Phe Leu Ser Lys Pro Ser Ser
                110                 115                 120

Phe Pro Lys Ala Met Glu Thr Thr Thr Thr Thr Ser Thr Thr
                125                 130                 135

Ser Pro Ala Thr Pro Ser Ala Gly Gly Ala Ala Ser Ser Arg Thr
                140                 145                 150

Pro Asn Arg Ile Ser Thr Arg Leu Thr Thr Ile Thr Arg Ala Pro
                155                 160                 165

Thr Arg Phe Pro Gly His Arg Val Pro Ile Arg Ala Ser Pro Arg
                170                 175                 180

Ser Thr Thr Ala Arg Asn Thr Ala Ala Pro Ala Thr Val Pro Ser
                185                 190                 195

Thr Thr Ala Pro Phe Phe Ser Ser Ser Thr Leu Gly Ser Arg Pro
                200                 205                 210

Pro Val Pro Gly Thr Pro Ser Thr Gln Ala Met Pro Ser Trp Pro
                215                 220                 225

Thr Ala Ala Tyr Ala Thr Ser Ser Tyr Leu His Asp Ser Thr Pro
                230                 235                 240

Ser Trp Thr Leu Ser Pro Phe Gln Asp Ala Ala Ser Ser Ser Ser
                245                 250                 255

Ser Ser Ser Ser Ser Ala Thr Thr Thr Pro Glu Ser Thr
                260                 265                 270

Ser Pro Lys Phe His Thr Thr Thr Tyr Ser Thr Glu Arg Ser Glu
                275                 280                 285

His Phe Lys Pro Cys Arg Asp Lys Asp Leu Ala Tyr Cys Leu Asn
                290                 295                 300

Asp Gly Glu Cys Phe Val Ile Glu Thr Leu Thr Gly Ser His Lys
                305                 310                 315

His Cys Arg Cys Lys Glu Gly Tyr Gln Gly Val Arg Cys Asp Gln
                320                 325                 330

Phe Leu Pro Lys Thr Asp Ser Ile Leu Ser Asp Pro Thr Asp His
                335                 340                 345

Leu Gly Ile Glu Phe Met Glu Ser Glu Glu Val Tyr Gln Arg Gln
                350                 355                 360

(2) INFORMATION FOR SEQ ID NO:8:

(i) SEQUENCE CHARACTERISTICS:
        (A) LENGTH: 47 amino acids
        (B) TYPE: Amino Acid
        (D) TOPOLOGY: Linear (ix) FEATURE:
        (A) NAME/KEY: NRG3 EGF-like domain/amino acid seq.
        (B) LOCATION: 1-47
        (C) IDENTIFICATION METHOD:
        (D) OTHER INFORMATION:

(xi) SEQUENCE DESCRIPTION: SEQ ID NO:8:

His Phe Lys Pro Cys Arg Asp Lys Asp Leu Ala Tyr Cys Leu Asn
 1               5                  10                  15
```

```
Asp Gly Glu Cys Phe Val Ile Glu Thr Leu Thr Gly Ser His Lys
            20                  25                  30

His Cys Arg Cys Lys Glu Gly Tyr Gln Gly Val Arg Cys Asp Gln
            35                  40                  45

Phe Leu
    47
```

(2) INFORMATION FOR SEQ ID NO:9:

(i) SEQUENCE CHARACTERISTICS:
        (A) LENGTH: 48 amino acids
        (B) TYPE: Amino Acid
        (D) TOPOLOGY: Linear (ix) FEATURE:
        (A) NAME/KEY: cARIA.egf
        (B) LOCATION: 1-48
        (C) IDENTIFICATION METHOD:
        (D) OTHER INFORMATION:

(xi) SEQUENCE DESCRIPTION: SEQ ID NO:9:

```
His Leu Thr Lys Cys Asp Ile Lys Gln Lys Ala Phe Cys Val Asn
 1               5                  10                  15

Gly Gly Glu Cys Tyr Met Val Lys Asp Leu Pro Asn Pro Pro Arg
            20                  25                  30

Tyr Leu Cys Arg Cys Pro Asn Glu Phe Thr Gly Asp Arg Cys Gln
            35                  40                  45

Asn Tyr Val
        48
```

(2) INFORMATION FOR SEQ ID NO:10:

(i) SEQUENCE CHARACTERISTICS:
        (A) LENGTH: 45 amino acids
        (B) TYPE: Amino Acid
        (D) TOPOLOGY: Linear (ix) FEATURE:
        (A) NAME/KEY: hAR.egf
        (B) LOCATION: 1-45
        (C) IDENTIFICATION METHOD:
        (D) OTHER INFORMATION:

(xi) SEQUENCE DESCRIPTION: SEQ ID NO:10:

```
Lys Lys Asn Pro Cys Asn Ala Glu Phe Gln Asn Phe Cys Ile His
 1               5                  10                  15

Gly Glu Cys Lys Tyr Ile Glu His Leu Glu Ala Val Thr Cys Lys
            20                  25                  30

Cys Gln Gln Gly Tyr Phe Gly Glu Arg Cys Gly Glu Lys Ser Met
            35                  40                  45
```

(2) INFORMATION FOR SEQ ID NO:11:

(i) SEQUENCE CHARACTERISTICS:
        (A) LENGTH: 45 amino acids
        (B) TYPE: Amino Acid
        (D) TOPOLOGY: Linear (ix) FEATURE:
        (A) NAME/KEY: hBTC.efg
        (B) LOCATION: 1-45
        (C) IDENTIFICATION METHOD:
        (D) OTHER INFORMATION:

(xi) SEQUENCE DESCRIPTION: SEQ ID NO:11:

```
His Phe Ser Arg Cys Pro Lys Gln Tyr Lys His Tyr Cys Ile Lys
 1               5                  10                  15

Gly Arg Cys Arg Phe Val Val Ala Glu Gln Thr Pro Ser Cys Val
                20                  25                  30

Cys Asp Glu Gly Tyr Ile Gly Ala Arg Cys Glu Arg Val Asp Leu
                35                  40                  45
```

(2) INFORMATION FOR SEQ ID NO:12:

(i) SEQUENCE CHARACTERISTICS:
        (A) LENGTH: 46 amino acids
        (B) TYPE: Amino Acid
        (D) TOPOLOGY: Linear (ix) FEATURE:
        (A) NAME/KEY: hEGF.egf
        (B) LOCATION: 1-46
        (C) IDENTIFICATION METHOD:
        (D) OTHER INFORMATION:

(xi) SEQUENCE DESCRIPTION: SEQ ID NO:12:

```
Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys
                20                  25                  30

Asn Cys Val Val Gly Tyr Ile Gly Glu Arg Cys Gln Tyr Arg Asp
                35                  40                  45

Leu
 46
```

(2) INFORMATION FOR SEQ ID NO:13:

(i) SEQUENCE CHARACTERISTICS:
        (A) LENGTH: 45 amino acids
        (B) TYPE: Amino Acid
        (D) TOPOLOGY: Linear (ix) FEATURE:
        (A) NAME/KEY: hHB-EGF.egf
        (B) LOCATION: 1-45
        (C) IDENTIFICATION METHOD:
        (D) OTHER INFORMATION:

(xi) SEQUENCE DESCRIPTION: SEQ ID NO:13:

```
Lys Arg Asp Pro Cys Leu Arg Lys Tyr Lys Asp Phe Cys Ile His
 1               5                  10                  15

Gly Glu Cys Lys Tyr Val Lys Glu Leu Arg Ala Pro Ser Cys Ile
                20                  25                  30

Cys His Pro Gly Tyr His Gly Glu Arg Cys His Gly Leu Ser Leu
                35                  40                  45
```

(2) INFORMATION FOR SEQ ID NO:14:

(i) SEQUENCE CHARACTERISTICS:
        (A) LENGTH: 49 amino acids
        (B) TYPE: Amino Acid
        (D) TOPOLOGY: Linear (ix) FEATURE:
        (A) NAME/KEY: hHRGalpha.egf
        (B) LOCATION: 1-49
        (C) IDENTIFICATION METHOD:
        (D) OTHER INFORMATION:

(xi) SEQUENCE DESCRIPTION: SEQ ID NO:14:

```
His Leu Val Lys Cys Ala Glu Lys Glu Lys Thr Phe Cys Val Asn
```

-continued

```
                1               5              10              15
Gly Gly Glu Cys Phe Met Val Lys Asp Leu Ser Asn Pro Ser Arg
                               20                  25                  30

Tyr Leu Cys Lys Cys Gln Pro Gly Phe Thr Gly Ala Arg Cys Thr
                               35                  40                  45

Glu Asn Tyr Pro
                49
```

(2) INFORMATION FOR SEQ ID NO:15:

(i) SEQUENCE CHARACTERISTICS:
        (A) LENGTH: 48 amino acids
        (B) TYPE: Amino Acid
        (D) TOPOLOGY: Linear (ix) FEATURE:
        (A) NAME/KEY: hHRGbeta.egf
        (B) LOCATION: 1-48
        (C) IDENTIFICATION METHOD:
        (D) OTHER INFORMATION:

(xi) SEQUENCE DESCRIPTION: SEQ ID NO:15:

```
                1               5              10              15
His Leu Val Lys Cys Ala Glu Lys Glu Lys Thr Phe Cys Val Asn 20                  25                  30
Gly Gly Glu Cys Phe Met Val Lys Asp Leu Ser Asn Pro Ser Arg 35                  40                  45
Tyr Leu Cys Lys Cys Pro Asn Glu Phe Thr Gly Asp Arg Cys Gln

Asn Tyr Val
        48
```

(2) INFORMATION FOR SEQ ID NO:16:

(i) SEQUENCE CHARACTERISTICS:
        (A) LENGTH: 45 amino acids
        (B) TYPE: Amino Acid
        (D) TOPOLOGY: Linear (ix) FEATURE:
        (A) NAME/KEY: hTGFalpha.egf
        (B) LOCATION: 1-45
        (C) IDENTIFICATION METHOD:
        (D) OTHER INFORMATION:

(xi) SEQUENCE DESCRIPTION: SEQ ID NO:16:

```
                1               5              10              15
His Phe Asn Asp Cys Pro Asp Ser His Thr Gln Phe Cys Phe His 20                  25                  30
Gly Thr Cys Arg Phe Leu Val Gln Glu Asp Lys Pro Ala Cys Val 35                  40                  45
Cys His Ser Gly Tyr Val Gly Ala Arg Cys Glu His Ala Asp Leu
```

(2) INFORMATION FOR SEQ ID NO:17:

(i) SEQUENCE CHARACTERISTICS:
        (A) LENGTH: 45 amino acids
        (B) TYPE: Amino Acid
        (D) TOPOLOGY: Linear (ix) FEATURE:
        (A) NAME/KEY: mEPR.egf
        (B) LOCATION: 1-45
        (C) IDENTIFICATION METHOD:
        (D) OTHER INFORMATION:

(xi) SEQUENCE DESCRIPTION: SEQ ID NO:17:

```
Gln Ile Thr Lys Cys Ser Ser Asp Met Asp Gly Tyr Cys Leu His
  1               5                  10                  15

Gly Gln Cys Ile Tyr Leu Val Asp Met Arg Glu Lys Phe Cys Arg
                 20                  25                  30

Cys Glu Val Gly Tyr Thr Gly Leu Arg Cys Glu His Phe Phe Leu
                 35                  40                  45

(2) INFORMATION FOR SEQ ID NO:18:

(i) SEQUENCE CHARACTERISTICS:
        (A) LENGTH: 50 amino acids
        (B) TYPE: Amino Acid
        (D) TOPOLOGY: Linear (ix) FEATURE:
        (A) NAME/KEY: Oligonucleotide probe
        (B) LOCATION: 1-50
        (C) IDENTIFICATION METHOD:
        (D) OTHER INFORMATION:

(xi) SEQUENCE DESCRIPTION: SEQ ID NO:18:

Thr Gly Gly Thr Ala Ala Ala Ala Gly Cys Thr Ala Cys Ala Gly
  1               5                  10                  15

Thr Cys Thr Cys Ala Ala Ala Gly Cys Ala Thr Cys Cys Ala Gly
                 20                  25                  30

Cys Ala Cys Ala Ala Thr Gly Gly Cys Ala Ala Ala Gly Thr Cys
                 35                  40                  45

Ala Gly Ala Gly Ala
                 50

(2) INFORMATION FOR SEQ ID NO:19:

(i) SEQUENCE CHARACTERISTICS:
        (A) LENGTH: 8 amino acids
        (B) TYPE: Amino Acid
        (D) TOPOLOGY: Linear (ix) FEATURE:
        (A) NAME/KEY: hNRG3B1 transmembrane proximal 1
        (B) LOCATION: 1-8
        (C) IDENTIFICATION METHOD:
        (D) OTHER INFORMATION:

(xi) SEQUENCE DESCRIPTION: SEQ ID NO:19:

Asn Asp Gly Glu Cys Phe Val Ile
  1               5           8

(2) INFORMATION FOR SEQ ID NO:20:

(i) SEQUENCE CHARACTERISTICS:
        (A) LENGTH: 9 amino acids
        (B) TYPE: Amino Acid
        (D) TOPOLOGY: Linear (ix) FEATURE:
        (A) NAME/KEY: hNRG3B1 transmembrane proximal 2
        (B) LOCATION: 1-9
        (C) IDENTIFICATION METHOD:
        (D) OTHER INFORMATION:

(xi) SEQUENCE DESCRIPTION: SEQ ID NO:20:

Glu Phe Met Glu Ser Glu Glu Val Tyr
  1               5               9

(2) INFORMATION FOR SEQ ID NO:21:
```

```
     (i) SEQUENCE CHARACTERISTICS:
         (A) LENGTH: 466 base pairs
         (B) TYPE: Nucleic Acid
         (C) STRANDEDNESS: Single
         (D) TOPOLOGY: Linear (ix) FEATURE:
         (A) NAME/KEY: EST Genbank entry H23651
         (B) LOCATION: 1-466
         (C) IDENTIFICATION METHOD:
         (D) OTHER INFORMATION:

(xi) SEQUENCE DESCRIPTION: SEQ ID NO:21:

AATTTCTGCC GAAAACTGAT TCCATCTTAT CGGATCCAAC AGACCACTTG            50

GGGATTGAAT TCATGGAGAG TGAAGAAGTT TATCAAAGGC AGGTGCTGTC           100

AATTTCATGT ATCATCTTTG GAATTGTCAT CGTGGGCATG TTCTGTGCAG           150

CATTCTACTT CAAAAGCAAG AAACAAGCTA ACAAATCCA AGAGCAGCTG            200

AAAGTGCCAC AAAATGGTAA AAGCTACAGT CTCAAAGCAT CCAGCACAAT           250

GGCAAAGTCA GAGAACTTGG TGAAGAGCCA TGTCCAGCTG CAAAATAAAA           300

TGTCAGGCTT CTGAGCCCAA GCTAAGCCAT CATATCCCCT GTNGACCTGC           350

ACGTGCACAT CCNGATGGCC CGTTTCCTGC CTTTTNTGAT GACATTTNCA           400

CCACAAATGN AGTGAAAATG GGNCTTTTCN TGCCTTAACT GGTTGACNTT           450

TTTNCCCCAA AAGGAG                                                466

(2) INFORMATION FOR SEQ ID NO:22:

(i) SEQUENCE CHARACTERISTICS:
         (A) LENGTH: 2091 base pairs
         (B) TYPE: Nucleic Acid
         (C) STRANDEDNESS: Single
         (D) TOPOLOGY: Linear (ix) FEATURE:
         (A) NAME/KEY: Human NRG3B2 (hNRGB2)
         (B) LOCATION: 1-2091
         (C) IDENTIFICATION METHOD:
         (D) OTHER INFORMATION:

(xi) SEQUENCE DESCRIPTION: SEQ ID NO:22:

ATGAGTGAAG GGGCGGCCGC TGCCTCGCCA CCTGGTGCCG CTTCGGCAGC            50

CGCCGCCTCG GCCGAGGAGG GCACCGCGGC GGCTGCGGCG GCGGCAGCGG           100

CGGGCGGGGG CCCGGACGGC GGCGGCGAAG GGGCGGCCGA GCCCCCCCGG           150

GAGTTACGCT GTAGCGACTG CATCGTGTGG AACCGGCAGC AGACGTGGCT           200

GTGCGTGGTA CCTCTGTTCA TCGGCTTCAT CGGCCTGGGG CTCAGCCTCA           250

TGCTTCTCAA ATGGATCGTG GTGGGCTCCG TCAAGGAGTA CGTGCCCACC           300

GACCTAGTGG ACTCCAAGGG GATGGGCCAG GACCCCTTCT TCCTCTCCAA           350

GCCCAGCTCT TTCCCCAAGG CCATGGAGAC CACCACCACT ACCACTTCCA           400

CCACGTCCCC CGCCACCCCC TCCGCCGGGG GTGCCGCCTC CTCCAGGACG           450

CCCAACCGGA TTAGCACTCG CCTGACCACC ATCACGCGGG CGCCCACTCG           500

CTTCCCCGGG CACCGGGTGC CCATCCGGGC CAGCCCGCGC TCCACCACAG           550

CACGGAACAC TGCGGCCCCT GCGACGGTCC CGTCCACCAC GGCCCCGTTC           600

TTCAGTAGCA GCACGCTGGG CTCCCGACCC CCGGTGCCAG GAACTCCAAG           650

TACCCAGGCA ATGCCCTCCT GGCCTACTGC GGCATACGCT ACCTCCTCCT           700
```

-continued

```
ACCTTCACGA TTCTACTCCC TCCTGGACCC TGTCTCCCTT TCAGGATGCT        750

GCCTCCTCTT CTTCCTCTTC TTCCTCCTCC GCTACCACCA CCACACCAGA        800

AACTAGCACC AGCCCCAAAT TCATACGAC  GACATATTCC ACAGAGCGAT        850

CCGAGCACTT CAAACCCTGC CGAGACAAGG ACCTTGCATA CTGTCTCAAT        900

GATGGCGAGT GCTTTGTGAT CGAAACCCTG ACCGGATCCC ATAAACACTG        950

TCGGTGCAAA GAAGGCTACC AAGGAGTCCG TTGTGATCAA TTTCTGCCGA       1000

AAACTGATTC CATCTTATCG GATCCAACAG ACCACTTGGG GATTGAATTC       1050

ATGGAGAGTG AAGAAGTTTA TCAAAGGCAG GTGCTGTCAA TTTCATGTAT       1100

CATCTTTGGA ATTGTCATCG TGGGCATGTT CTGTGCAGCA TTCTACTTCA       1150

AAAGCAAGAA ACAAGCTAAA CAAATCCAAG AGCAGCTGAA AGTGCCACAA       1200

AATGGTAAAA GCTACAGTCT CAAAGCATCC AGCACAATGG CAAAGTCAGA       1250

GAACTTGGTG AAGAGCCATG TCCAGCTGCA AAATTATTCA AAGGTGGAAA       1300

GGCATCCTGT GACTGCATTG GAGAAAATGA TGGAGTCAAG TTTTGTCGGC       1350

CCCCAGTCAT TCCCTGAGGT CCCTTCTCCT GACAGAGGAA GCCAGTCTGT       1400

CAAACACCAC AGGAGTCTAT CCTCTTGCTG CAGCCCAGGG CAAAGAAGTG       1450

GCATGCTCCA TAGGAATGCC TTCAGAAGGA CACCCCCGTC ACCCCGAAGT       1500

AGGCTAGGTG GAATTGTGGG ACCAGCATAT CAGCAACTCG AAGAATCAAG       1550

GATCCCAGAC CAGGATACGA TACCTTGCCA AGGGTATTCA TCCAGTGGTT       1600

TAAAAACCCA ACGAAATACA TCAATAAATA TGCAACTGCC TTCAAGAGAG       1650

ACAAACCCCT ATTTAATAG  CTTGGAGCAA AAGGACCTGG TGGGCTATTC       1700

ATCCACAAGG GCCAGTTCTG TGCCCATCAT CCCTTCAGTG GGTTTAGAGG       1750

AAACCTGCCT GCAAATGCCA GGGATTTCTG AAGTCAAAAG CATCAAATGG       1800

TGCAAAAACT CCTATTCAGC TGACGTTGTC AATGTGAGTA TTCCAGTCAG       1850

CGATTGTCTT ATAGCAGAAC AACAAGAAGT GAAATATTG  CTAGAAACTG       1900

TCCAGGAGCA GATCCGAATT CTGACTGATG CCAGACGGTC AGAAGACTAC       1950

GAACTGGCCA GCGTAGAAAC CGAGGACAGT GCAAGTGAAA ACACAGCCTT       2000

TCTCCCCCTG AGTCCCACAG CCAAATCAGA ACGAGAGGCG CAATTTGTCT       2050

TAAGAAATGA AATACAAAGA GACTCTGCAT TGACCAAGTG A                2091
```

(2) INFORMATION FOR SEQ ID NO:23:

(i) SEQUENCE CHARACTERISTICS:
        (A) LENGTH: 696 amino acids
        (B) TYPE: Amino Acid
        (D) TOPOLOGY: Linear (ix) FEATURE:
        (A) NAME/KEY: Human NRG3B2
        (B) LOCATION: 1-696
        (C) IDENTIFICATION METHOD:
        (D) OTHER INFORMATION:

(xi) SEQUENCE DESCRIPTION: SEQ ID NO:23:

```
Met Ser Glu Gly Ala Ala Ala Ala Ser Pro Pro Gly Ala Ala Ser
 1               5                  10                  15

Ala Ala Ala Ser Ala Glu Glu Gly Thr Ala Ala Ala Ala
                20                  25                  30

Ala Ala Ala Ala Gly Gly Gly Pro Asp Gly Gly Gly Glu Gly Ala
```

-continued

```
                35                  40                  45
Ala Glu Pro Pro Arg Glu Leu Arg Cys Ser Asp Cys Ile Val Trp
             50                  55                  60

Asn Arg Gln Gln Thr Trp Leu Cys Val Val Pro Leu Phe Ile Gly
             65                  70                  75

Phe Ile Gly Leu Gly Leu Ser Leu Met Leu Leu Lys Trp Ile Val
             80                  85                  90

Val Gly Ser Val Lys Glu Tyr Val Pro Thr Asp Leu Val Asp Ser
             95                 100                 105

Lys Gly Met Gly Gln Asp Pro Phe Phe Leu Ser Lys Pro Ser Ser
            110                 115                 120

Phe Pro Lys Ala Met Glu Thr Thr Thr Thr Thr Ser Thr Thr
            125                 130                 135

Ser Pro Ala Thr Pro Ser Ala Gly Gly Ala Ala Ser Ser Arg Thr
            140                 145                 150

Pro Asn Arg Ile Ser Thr Arg Leu Thr Ile Thr Arg Ala Pro
            155                 160                 165

Thr Arg Phe Pro Gly His Arg Val Pro Ile Arg Ala Ser Pro Arg
            170                 175                 180

Ser Thr Thr Ala Arg Asn Thr Ala Ala Pro Ala Thr Val Pro Ser
            185                 190                 195

Thr Thr Ala Pro Phe Phe Ser Ser Ser Thr Leu Gly Ser Arg Pro
            200                 205                 210

Pro Val Pro Gly Thr Pro Ser Thr Gln Ala Met Pro Ser Trp Pro
            215                 220                 225

Thr Ala Ala Tyr Ala Thr Ser Ser Tyr Leu His Asp Ser Thr Pro
            230                 235                 240

Ser Trp Thr Leu Ser Pro Phe Gln Asp Ala Ala Ser Ser Ser Ser
            245                 250                 255

Ser Ser Ser Ser Ser Ala Thr Thr Thr Thr Pro Glu Thr Ser Thr
            260                 265                 270

Ser Pro Lys Phe His Thr Thr Thr Tyr Ser Thr Glu Arg Ser Glu
            275                 280                 285

His Phe Lys Pro Cys Arg Asp Lys Asp Leu Ala Tyr Cys Leu Asn
            290                 295                 300

Asp Gly Glu Cys Phe Val Ile Glu Thr Leu Thr Gly Ser His Lys
            305                 310                 315

His Cys Arg Cys Lys Glu Gly Tyr Gln Gly Val Arg Cys Asp Gln
            320                 325                 330

Phe Leu Pro Lys Thr Asp Ser Ile Leu Ser Asp Pro Thr Asp His
            335                 340                 345

Leu Gly Ile Glu Phe Met Glu Ser Glu Val Tyr Gln Arg Gln
            350                 355                 360

Val Leu Ser Ile Ser Cys Ile Ile Phe Gly Ile Val Ile Val Gly
            365                 370                 375

Met Phe Cys Ala Ala Phe Tyr Phe Lys Ser Lys Lys Gln Ala Lys
            380                 385                 390

Gln Ile Gln Glu Gln Leu Lys Val Pro Gln Asn Gly Lys Ser Tyr
            395                 400                 405

Ser Leu Lys Ala Ser Ser Thr Met Ala Lys Ser Glu Asn Leu Val
            410                 415                 420

Lys Ser His Val Gln Leu Gln Asn Tyr Ser Lys Val Glu Arg His
            425                 430                 435
```

```
Pro Val Thr Ala Leu Glu Lys Met Met Glu Ser Ser Phe Val Gly
            440                 445                 450

Pro Gln Ser Phe Pro Glu Val Pro Ser Pro Asp Arg Gly Ser Gln
            455                 460                 465

Ser Val Lys His His Arg Ser Leu Ser Ser Cys Cys Ser Pro Gly
            470                 475                 480

Gln Arg Ser Gly Met Leu His Arg Asn Ala Phe Arg Arg Thr Pro
            485                 490                 495

Pro Ser Pro Arg Ser Arg Leu Gly Gly Ile Val Gly Pro Ala Tyr
            500                 505                 510

Gln Gln Leu Glu Glu Ser Arg Ile Pro Asp Gln Asp Thr Ile Pro
            515                 520                 525

Cys Gln Gly Tyr Ser Ser Ser Gly Leu Lys Thr Gln Arg Asn Thr
            530                 535                 540

Ser Ile Asn Met Gln Leu Pro Ser Arg Glu Thr Asn Pro Tyr Phe
            545                 550                 555

Asn Ser Leu Glu Gln Lys Asp Leu Val Gly Tyr Ser Ser Thr Arg
            560                 565                 570

Ala Ser Ser Val Pro Ile Ile Pro Ser Val Gly Leu Glu Glu Thr
            575                 580                 585

Cys Leu Gln Met Pro Gly Ile Ser Glu Val Lys Ser Ile Lys Trp
            590                 595                 600

Cys Lys Asn Ser Tyr Ser Ala Asp Val Val Asn Val Ser Ile Pro
            605                 610                 615

Val Ser Asp Cys Leu Ile Ala Glu Gln Gln Glu Val Lys Ile Leu
            620                 625                 630

Leu Glu Thr Val Gln Glu Gln Ile Arg Ile Leu Thr Asp Ala Arg
            635                 640                 645

Arg Ser Glu Asp Tyr Glu Leu Ala Ser Val Glu Thr Glu Asp Ser
            650                 655                 660

Ala Ser Glu Asn Thr Ala Phe Leu Pro Leu Ser Pro Thr Ala Lys
            665                 670                 675

Ser Glu Arg Glu Ala Gln Phe Val Leu Arg Asn Glu Ile Gln Arg
            680                 685                 690

Asp Ser Ala Leu Thr Lys
            695 696
```